US008791237B2

(12) United States Patent
Paterson et al.

(10) Patent No.: US 8,791,237 B2
(45) Date of Patent: Jul. 29, 2014

(54) COMPOSITIONS AND METHODS FOR TREATMENT OF NON-HODGKINS LYMPHOMA

(75) Inventors: Yvonne Paterson, Philadephia, PA (US); Paul Neeson, Havertown, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 697 days.

(21) Appl. No.: 11/415,271

(22) Filed: May 2, 2006

(65) Prior Publication Data
US 2006/0269561 A1 Nov. 30, 2006

(51) Int. Cl.
C07K 1/00 (2006.01)

(52) U.S. Cl.
USPC .......................................... 530/350

(58) Field of Classification Search
None
See application file for complete search history.

(56) References Cited

U.S. PATENT DOCUMENTS

| | | | |
|---|---|---|---|
| 4,521,382 A | 6/1985 | Kessick et al. | |
| 4,567,041 A | 1/1986 | Likhite | |
| 4,777,239 A | 10/1988 | Schoolnik et al. | |
| 4,816,253 A | 3/1989 | Likhite | |
| 4,879,213 A | 11/1989 | Fox et al. | |
| 5,262,177 A | 11/1993 | Brown et al. | |
| 5,342,774 A | 8/1994 | Boon et al. | |
| 5,369,008 A | 11/1994 | Arlinghaus et al. | |
| 5,643,599 A | 7/1997 | Lee et al. | |
| 5,679,356 A * | 10/1997 | Bonnem et al. | 424/278.1 |
| 5,681,570 A | 10/1997 | Yang et al. | |
| 5,719,054 A | 2/1998 | Boursnell et al. | |
| 5,728,399 A | 3/1998 | Wu et al. | |
| 5,824,538 A | 10/1998 | Branstrom et al. | |
| 5,830,702 A * | 11/1998 | Portnoy et al. | 435/69.3 |
| 5,858,682 A | 1/1999 | Gruenwald et al. | |
| 5,876,735 A | 3/1999 | Reed | |
| 5,877,159 A | 3/1999 | Powell et al. | |
| 6,015,567 A | 1/2000 | Hudziak et al. | |
| 6,051,237 A | 4/2000 | Paterson | |
| 6,306,404 B1 | 10/2001 | LaPosta et al. | |
| 6,333,169 B1 | 12/2001 | Hudziak et al. | |
| 6,479,258 B1 | 11/2002 | Short | |
| 6,521,449 B1 | 2/2003 | Polack et al. | |
| 6,562,347 B1 * | 5/2003 | Kwak et al. | 424/192.1 |
| 6,565,852 B1 | 5/2003 | Paterson | |
| 6,767,542 B2 | 7/2004 | Paterson et al. | |
| 6,855,320 B2 | 2/2005 | Paterson | |
| 7,135,188 B2 | 11/2006 | Paterson | |
| 7,198,792 B2 | 4/2007 | Regts et al. | |
| 7,217,419 B2 | 5/2007 | Wettendorff | |
| 7,488,490 B2 | 2/2009 | Davis et al. | |
| 2003/0028206 A1 | 2/2003 | Shiber | |
| 2003/0202985 A1 | 10/2003 | Paterson | |
| 2003/0220239 A1 | 11/2003 | Simard et al. | |
| 2004/0013690 A1 | 1/2004 | Portnoy et al. | |
| 2004/0197343 A1 | 10/2004 | Dubensky, Jr. et al. | |
| 2004/0228877 A1 | 11/2004 | Dubensky, Jr. et al. | |
| 2005/0118184 A1 | 6/2005 | Paterson et al. | |
| 2005/0129715 A1 | 6/2005 | Paterson et al. | |
| 2006/0051380 A1 | 3/2006 | Schulick et al. | |
| 2006/0093582 A1 | 5/2006 | Paterson et al. | |
| 2006/0104991 A1 | 5/2006 | Paterson et al. | |
| 2006/0121053 A1 | 6/2006 | Sweeney et al. | |
| 2006/0205067 A1 | 9/2006 | Paterson et al. | |
| 2006/0210540 A1 | 9/2006 | Paterson et al. | |
| 2006/0233835 A1 | 10/2006 | Paterson et al. | |
| 2006/0269561 A1 | 11/2006 | Paterson et al. | |
| 2008/0124354 A1 | 5/2008 | Paterson et al. | |

FOREIGN PATENT DOCUMENTS

| | | |
|---|---|---|
| EP | 0 902 086 | 3/1999 |
| JP | 63-173594 | 7/1988 |
| WO | WO 90/12594 | 11/1990 |
| WO | WO 92/20356 | 11/1992 |
| WO | WO 93/15212 | 8/1993 |
| WO | WO 94/17192 | 8/1994 |
| WO | WO 95/34631 | 11/1995 |
| WO | WO 96/14087 | 5/1996 |
| WO | WO 98/48026 | 10/1998 |
| WO | WO 99/06544 | 2/1999 |
| WO | WO 99/07861 | 2/1999 |
| WO | WO 99/10496 | 3/1999 |
| WO | WO 99/25376 | 5/1999 |
| WO | WO 01/27295 | 4/2001 |
| WO | WO 01/72329 | 10/2001 |
| WO | WO 03/015716 | 2/2003 |
| WO | WO 03/092600 | 11/2003 |
| WO | WO 2004/006837 | 1/2004 |
| WO | WO 2006/036550 | 4/2006 |
| WO | WO 2007/061848 | 5/2007 |
| WO | WO 2007/106476 | 9/2007 |
| WO | WO 2007/130455 | 11/2007 |

OTHER PUBLICATIONS

Ikonomidis et al., J. Exp. Med. vol. 180, p. 2209-18, 1994.*
Kwak et al., Pro. Nalt. Acad. Sci. vol. 93, p. 10972-10977, 1996.*
Meneguzzi et al, Virology, vol. 181 p. 62-9, 1991, abstract.*
Meneguzzi et al (Virology, 1991, 181: 62-69).*
Adams at el. (1992) "Cre-*lox* recombination in *Escharichla coli* cells. Mechanistic differences from the in vitro reaction." *J. Mol. Biol.* 226:681-673.
Allison at J. (1997) "Cloning and charactertralion of a *Prevotella melaninogenica* hemolysin." *Infect Immun.* 65(7).2765-71.
An et al. (1996) "A recombinant minigene vaccine containing a nonameric cytoxic-T-Lymphocyte spitope confers limited protection against *Listena monocytogenes* infection" *Infect. Immun* 64,(5):1685-1693.

(Continued)

*Primary Examiner* — Sean Aeder

(74) *Attorney, Agent, or Firm* — Mark S. Cohen; Pearl Cohen Zedek Latzer Baratz LLP

(57) ABSTRACT

The present invention provides recombinant peptides comprising a B cell receptor (BCR) or a fragment thereof, nucleotide molecules encoding same, and vaccines and vectors comprising same; and methods of treating, inducing an immune response against, inducing a regression of, and suppressing a formation of a lymphoma, comprising administering same. The present invention also provides methods of inducing a humoral immune response in an animal against an antigen, comprising administering to the animal a fusion peptide comprising an LLO protein or fragment thereof fused to the antigen.

12 Claims, 35 Drawing Sheets

(56) References Cited

OTHER PUBLICATIONS

Anderson (1996) "Human gene therapy." *Nature.* Apr. 30;392(6679 Suppl):25-30.

Angelakopoulos at al. (2602) "Safety and shedding of an attenuated strain of *Listerla monocytogenes* with a deletion of actA/plcB in adult volunteers: a dose escalation study of oral inoculation." *Infect Immun.* 70(7):3592-801.

Attwood et al. (2000) "The Babel of Bioinformatics" *Science* 290(5491):471-473.

Awwad (1989) "Cyclophosphamide-induced immunologically mediated regression of a cyclophosphamide-resistant murine tumor: a consequence of eliminating precursor L3T4+ suppressor T-cells." *Cancer Res.* 49(7): 1649-1654.

Barry at al. (1992) "Pathogenicity and immunogenicity of *Listeria monocytogenes* small-plaque mutants defective for intracellular growth and cell-to-cell spread," *Infection and Immunity* 60 (4): 1625-32.

Bast at al. (1975) "Antitumor activity of bacterial infection, II. effect of *Listeria monocytogenes* can growth of a guinea pig hepatoma." *J. Natl. Cancer Inst.*, 54(3): 757-761.

Bear (1986) "Tumor-specific suppressor T-cells which inhibit the in vitro generation of cytolytic T-cells from immune and early tumor bearing host spleens." *Cancer Res.* Apr;46(4 Pt 1):1805-12.

Beatly, Dissertation Abstracts International, 2000,61/10B:5224 Abstract Only.

Bernkard et al, (2002) "Vaccination against the HER-2/neu oncogenic protein." *Endocrine-Related Cancer*, 9:33-44.

Bielecki at at (1990) "*Bacillus subtilis* expressing a haemolysin gene from *Listeria monocytogenes* can grow in mammalian cells" *Nature* 354:175-176.

Billington at al. (1997) "The Arcancbacterium (Actinomyces) pyogenes hemolysin, pyolysin, is a novel member of the thiol-activated cytolysin family." *J. Bacteriol.* Oct;179(19):6100-6.

Bodmer et al. (1988) "Enhanced recognition of a modified peptide antigen by cytotoxic T cells specific for influenza nucleoprotein," *Cell* 52: 253-258.

Boon et al. (2006) "Human T cell responses against melanoma" *Annu Rev Immunol.* 24:175-206.

Bourquin et al (2000) "Myelin oligodendrocyte glycoprotein-DNA vaccination Induce antibody-mediated autoaggression in experimental autoimmune encephalomyelitis" *Eur J Immunol* 30:3663-3671.

Boyer et el. (2005) "DNA prime *Listeria* boost induces a cellular immune response to SIV antigens in the rhesus macaque model that is capable of limited suppression of SIV239 viral replication." *Virology.* Mar 1:333(1):88-101.

Brasseur et al. (1992) "Human gene MAGE-1, which codes for a tumor-rejection antigen, is expressed by some breast tumors." *Int. J Cancer* 52(5)839-841.

Brockstedt et al. (2004) "*Listeria*-based cancer vaccines that segregate immunogenicity from toxicity." *Proc Natl Acad Sci USA.* 101(38):13832-7.

Bron et al. (2004) "Identification of *Lactobacillus plantarum* genes that are induced in the astrointestinal tract of mice." *J Bacteriol.* Sep:186(17):5721-9.

Brown et al. (1988) "Site-specific integration in *Saccharopolyspora erythraea* and multisite integration in *Steptomyces lividans* of actinomycete plasmid pSE101." *J. Bacteriology* 170: 2287-2295.

Bruhn et al. (2005) "Characterization of anti-self CD8 T-cell responses stimulated by recombinant *Listeria monocytogenes* expressing the melanoma antigen TRP-2." *Vaccine.* Jul. 21:23(33):4263-72.

Brundage et al. (1993) "Expression and phosphorylation of the *Listeria monocytogenes* AcIA protein in mammalian cells." *Proc. Natl. Acad. Sci. USA* 90: 11890-11894.

Bubert et al. (1997) "The *Listeria monocytogenes* lap gene as an indicator gene for the study of PrfA-dependent regulation." *Mol. Gen Genet.* Sep:256(1):54-62.

Burnham (2003) "Bad bugs: good for cancer therapy?" *Drug Discovery Today* 8(2):54-56.

Calendar et al. Poster presented at the ISOPOL Meeting 2001, http://54.233.169.104/search?q=cache:mA__uJpQsCrcJ:www.ma.uni-heidelberg.de/inst/imh/download/isopol.doc+Portnoy+Isopol+2001&hl=en&ct=cink&cd=3&gl=us.

Camilli et al. (1993) "Dual roles of plcA in *Listeria monocytogenes* pathogenesis." *Mol. Microbiol.* 8:143-157.

Carbone (1989) "Induction of ovalbumin-specifio cytotoxic T cells by in vivo peptide Immunization!" *J Exp Med* 169:603-812.

Carbone (1990) "Class I-restricted processing and presentation of exogenous cell-associated antigen in vivo." *J Exp Med* 171:377-387.

Chamberlain et al. (2000) "Innovations and strategies for the development of anticancer vaccines." *Expert Opinion on Pharmacotherapy* 1(4):603-614.

Courvalin et al. (1995) "Gene transfer from bacteria to mammalian cells." *C R Acad Sci III.* Dec;318(12):1207-12.

Cunto-Amesty et al. (2003) "Strategies in canter vaccines development." *Int J Parasitol.* 33(5-6):597-613.

Dakappagari at at (2000) "Prevention of mammary tumors svittl a chimeric HER-2 B-cell epitope peptide vaccine." *Cancer Res.* Jul 15;60(14)3782-9.

Darji et al. (2003) "Induction of immune responses by attenuated isogenic mutant strains of *Listeria monocytogenes*." *Vaccine* 1;21 Suppl 2:S102-9.

Darji et al. (1997) "Oral somatic transgene vaccination using attenuated *S. typhimunum*" *Cell* 91 :765-775.

Darji et al. (1995) "Hyperexpression of listenolysin in the nonpathogenic species *Listeria innocua* and high yield purifcation." *J Biotechnol.* Dec 15;43(3):206-12.

Darji et al. (1995) "Listeriolysin generates a route for the presentation of exogenous antigens by major histocompatibility complex class I." *Eur J Immunol.* Oct;25(10)2987-71.

Darji et al. (1997) "TAP-dependent major histocompatibility complex class I presentation of soluble proteins using listeriolysin." *Eur J Immunol.* Jun;27(8):1353-9.

Decatur et al. (2000) "A PEST-like sequence in Listeriolysin O essential for *Listeria monocytogenes* pathogenicity" *Science* 290(5493):992-995.

Dermime et al. (2004) "Vaccine and antibody-directed T cell tumour immunotherapy."*Biochim Biophys Acta.* 1704(1):11-35.

Deshpande et al. (1997) "Isolation of a contact-dependent haemolysin from Mycobacterium tuberculosis." *J Med Microbiol.* Mar:46(3).233-8.

Dietrich et al. (1998) "Delivery of antigen-encoding plasmid DNA into the cytosol of macrophages by attenuated suicide *Listeria monocytogenes*" *Nature Biotechnology* 15:181-186.

Dietrich at al. (2001) "From evil to good: a cylotysin in vaccine development." *Trends Microbiol.* Jan:9(1)23-8.

Dramsi et al. (1995) "Entry of *Listeria monocytogenes* into hepatocytes requires expression of inlB, a surface protein of the intemalin multigene family." *Mol Microbiol.* 16(2):251-61.

Dunn et at. (1991) "Selective radiation resistance of immunologically induced T cells as the basis for irradiation-induced T-cell-mediated regression of immunogenic tumor," *J Leukoc Biol.* 49(4): 388-396.

Ebert et al. (1990) "Selective immunosuppressive action of a factor produced by colon cancer cells."*Cancer Res.* 50(19): 6158-6161.

Ezzel (1995) "Cancer Vaccines: An Idea Whose Time Has Come?" J. NIH Res. 7:76-49.

Falk et al. (1991) "Identification of naturally processed viral nonapeptides allows their quantification in Infected cells and suggests an allele-specific T cell epitope forecast." *J Exp Med.* 174(2):425-434.

Finn at al. (2003) "Cancer vaccines: between the idea and the reality," *Nature Reviews Immunology* 3:930-641.

Frankel et al. (1995) "Induction of cell-mediated immune responses to human immunodeficiency virus type 1 Gag protein by using *Listeria monocytogenes* as a five vaccine vector." *J. Immunol.* 155:4776-4782.

Frey (1993) "Rat adenocarcinoma 13762 expresses tumor rejection antigens but tumor-bearing animals exhibit tumor-specific immunosuppression." *Clin Immunol Immunopathol.* 69(2):223-233.

(56) References Cited

OTHER PUBLICATIONS

Friedman at al. (2000) "Induction of human immunodeficiency virus (HIV)-specific CD8 T-cell responses by *Listeria monocytogenes* and a hyperattenuated *Listeria* strain engineered to express HIV antigens," *J. Virology* 74 9987-9993.
Fu et al. (1990) "Expansion of immunoregulatory macrophages by granulocyte-macrophage colony-stimulating factor derived from a murine mammary tumor," *Cancer Res.* 50(2):227-234.
Fujii (1987) "Signifigance of suppressor macrophages for immunosurveillance of tumor-bearing mice." *J Natl Cancer Inst.* 78(3):609-517.
Furukawa (1993) "Nude mouse metastatic models of human stomach cancer constructed using orthotopic implantation of histologically intact tissue." *Cancer Res.* 53(5):1204-1208.
Galen et al (2001) "Can a 'flawless' live vector vaccine strain be engineered?" *Trends Microbiol.* 9(8):372-6.
Gentschev et al. (1995) "*Samonella* strain secreting active Listeriolysin changes its intracellular localization" *Infect. Immun.* 63:4202-4205.
Gentschev et al. (1996) "Development of antigen-delivery systems, based on the *Escherichia coli* hemolysin secreatiohn pathway." *Gene* 179:133-140.
Gilmore et el. (1989) "A *Bacillus cereus* cytolytic determinant, careolysin AB, which comprises the phospholipase C and sphingotnyelinase genes: nucieolde sequence and genetic linkage." *J Bacteriol.* Feb:171(2):744-53.
Glomski et al. (2002) "The *Listeria monocytogenes* hemolysin has an acidic pH optimum to compartmentalize activity and prevent damage to infected host cells." *J Cell Biol.* Mar 18;156(6)1029-38.
Goebel et al. (1993) "*Listeria monocytogenes*—a model system for studying the pathomechanisms of an intracellular microorganism." *Zbl. Bakt*:278:334-347.
Goossens et al. (1992) "Induction of protective CD8+ T lymphocytes by an attenuated *Listeria monocytogenes* actA mutant." *Int Immunol.* Dec:4(12).1413-8.
Goossens et al. (1995) "Attenuated Listeda monocytogenes as a five vector for induction of CD8+ T cells in vivo: a study with the nucleoprotein of the lymphocytic choriomeningitis virus." *Int Immunol.* May;7(5)197-806.
Gregory et al. (1697) "Internalin B promotes the replication of *Listeria monocytogenes* in mouse hepatocytes". *Infect Immun.* 65(12):5137-41.
Gunn (2001) "Two *Listeria monocytogenes* vaccine vectors that express different molecuiar forms of human papilloma virus-16 (HPV-16) E7 induce qualitatively different T cell immunity that correlates with their ability to induce regression of established tumors immortalized by HPV-16," *J Immunol.* 167(11)6471-8479.
Gunn et al. (2002) "Recombinant Infra-cellular Bacteria as Carriers for Tumor Antigens." In *Vaccine Delivery Strategies*, Chapter 14, Eds, Guido Dietrich and Werner Goebel, Horizon Scientific Press, UK.
Gunn, Dissertation Abstracts International, 2001, 62/5B:2244 Abstract Only.
Gunn et al. (2001) "Listeriolysin—a useful cytolysin." *Trends Microbiol.*9(4):161-162.
Guzman et al, (1998) "Attenuated *Listeria monocytogenes* carrier strains can deliver are H1V-1 gp120 T helper epitope to MHC class 8-restricted human CD4+ T cells" *European Journal of Immunology* 28:1807-1814.
Harty et at (1996) "Primary and Secondary Immune responses to *Listeria monocytogenes*." *Curr Opin Immunol.* 8:526-530.
Hassan et al. (2004) "Mesothelin: a new target for immunotherapy." *Clin Cancer Res.* 10(12 Pt 1):3937-42.
Hauf et al. (1997) "*Listeria monocytogenes* infection of P388D1 macrophages results in a biphasic NF-kappa3 (RelA/p50) activation induced by lipoteichoic acid and bacterial phospholipases and mediated by IkappaBalpha end IkappaBbeta degradation" *Proc. Natl Acad Sci U S A.* Aug. 19;94(17):9394-9.

Hess et al. (1995) "*Listeria monocytogenes* p80 supports host cell invasion by and in vivo survival of attenuated *Salmonella typhimurium.*" *Infect Immun.* May:63(6)2047-53.
Hess at al. (1996) "*Salmonella typhimurium* ar0A- infection in gene-targeted immunodeficient mice: major role of CD4+ TCR-alpha beta cells and IFN-gamma in bacterial clearance independent of intracellular location." *J Immunol.* May 1;156(9):3321-6.
Hess et al. (1996) "Superior efficacy of secreted over somatic antigen display in recombinant *Salmonella* vaccine induced protection against listeriosis" *Proc. Nat. Acad. Sci.* 93:1458-1463.
Hess at al. (1997) "Protection against murine listertosis by an attenuated recombinant *Salmonella typhimurium* vaccine strain that secretes the naturally somatic antigen superoxide dismutase." *Infect Immun.* Apr:65(4):1286-92.
Hess et al. (1998) "*Mycobacterium bovis* bacilli Calmette-Guerin strains secreting listeriolysin of *Listeria monocytogenes*" *Proc. Natl. Acad. Sci.* 95:5299-5304.
Higgins et al. (1998) "Bacterial delivery of DNA evolves." *Nat Biotechnol.* Feb:16(2):138-9.
Hodgson (2000) "Generalized transduction of serotype 1/2 and serotype 4b strains of *Listeria monocytogenes*." *Mol Micobiol.* 35(2):312-23.
Hu et al. (2004) "*Escherichia coli* reasing recombinant antigen and listeriolysin O stimulate class I-restriCted CD8+ T cells following uptake by human APC." *J. Immunology* 172:1595-1601.
Huang at al. (1994) "Role of bone marrow-derived cells in presenting MHC class I-restricted tumor antigens." *Science* 264961-965.
Hussain et al. (2004) "CD4+CD25+ regulatory T cells that secrete TGFbeta and IL-10 are preferentially induced by a vaccine vector," *J. Immunother.* Sep-Oct;27(5):.339-46.
Ikonomidis et al. (1994) Abstract E-90, Abstracts, 94th General Meeting of the American Society for Microbiology, May 23-27.
Ikonomidis et al. (1994) "Delivery of a viral antigen to the class I processing and presentation oathway by *Listeria monocytogenes*" *Journal of Experimental Medicine* 190(6):2209-2218.
Jensen (1997) "Recombinant *Listeria monocytogenes* vaccination eliminates papillornavirus-induced tumors and prevents papilloma formation from viral DNA." *J Viol.* 71(11):8487-9474.
Jensen at al. (1997) "Recombinant *Listeria monocytogenes* as a live vaccine vehicle an probe for studying cell-mediated Immunity" *Immunological Review* 158.147-157.
Jones at al. (1994) "Characterization of *Listeria monocytogenes* pathogenesis in a strain expressing perfringolysin O in place of listerlolysin O." *Infect. Immun.* 62:5606-5613.
Kaufman et al. (1999) "Impact of intracellular location of and antigen display by intracellular bacteria: implications for vaccine development" *J. Immunol. Lett*, 65(1-2):81-84.
Kerksiek (1999) "T cell responses to bacterial infection" *Curr. Opin. Immunol.* 1(4):400-405.
Kocks et al. (1992) "*L. monocytogenes*-induced actin assembly requires the ActA gene product" *Cell* 68(3):521-531.
Kovacsovics-Bankowski et al. (1993) "Efficient major histocompatibility complex class I presentation of exogenous antigen upon phagocytosis by macrophages." *Proc. Natl. Acad. Sci. USA* 90:4942-4946.
Lamikanra et al. (2001) "Regression of established human papillomavirus type 16 (HPV-16) immortalized tumors in vivo by vaccinia viruses expressing different forms of HPV-16 E7 correlates with enhanced CD8(+) T-cell responses that home to the tumor site." *J. Virology* 75(20):9654-9664.
Lampson et at. (1993) "Exploting the lacZ reporter gene for quantitative analysis of disseminated tumor growth within the brain: use of the lacZ gene product as a tumor antigen, for evaluation of antigenic modulation and to facillitate image analysis of tumor growth in situ." *Cancer Research* 53:176-182.
Lara-Tejero et al. (2004) "T cell responses to *Listeria monocytogenes*." *Curr Opin Microbiol.* 7(1):45-50.
Lasa et al. (1997) "Identification of two regions in the N-terminal domain of ActA involved in the actin comet tail formation by *Listeria monocytogenes*" *EMBO* 16(7):1531-40.
Lauer et al. (2002) "Construction, characterization, and use of two *Listeria monocytogenes* site-specific phage integration vectors." *J. Bacteriology* 184: 4177-4186.

(56) References Cited

OTHER PUBLICATIONS

Lauer et al. ASM Meeting, Absract 1999.
Lebrun et al. (1996) "Internelin must be on the bacterial surface to mediate entry of *Listeria monocytogenes* into epithelial cells" *Molecular Microbiology* 21(3):579-592.
Leão et al. (1995) "A species-specific nucleotide sequence of *Mycobacterium tuberculosis* encodes a protein that exhibits hemolytic activity when expressed in *Escherichia coli*." *Infect Immun.* Nov;63(11):4301-6.
Lee et al. (1991) "Construction of single-copy integration vectots for *Staphylococcus aureus*." *Gene* 103:101-5.
Lehner et al. (1996) "Processing and delivery of peptides presented by MHC class, I molecules." *Curr Opin Immunol.* 8(1)59-67.
Lejeune (1994) "Nitric oxide involvement in tumor-induced immunosuppression." *J. Immunol.* 152(10):5077-5083.
Liau et al. (2002) "Tumor immunity within the central nervous system stimulated by recombinant *Listeria monocytogenes* vaccination." *Cancer Res.* 62(8)2287-93.
Lin et al. (1996) Treatment of established tumors with a novel vaccine that enhances Major Histocompatibility Class II presentation of tumor antigen *Cancer Res.* 56:21-26.
Lin at al. (2002) "Oral venation with recombinant *Listeria monocytogenes* expressing human papillornavirus type 16 E7 can cause tumor growth in mice to regress." *Int J Cancer.* Dec. 20; 102 S :629-37.
Lingnau et al. (1995) "Expression of the *Listeria monocytogenes* EGD inlA and inllB genes, whose products mediate bacterial entry into tissue culture cell lines, by PrfA-dependent and—independent mechanisms." *Infect Immun.* Oct;63(10):3896-903.
Loeffler at al, (2006) "Comparison of different live vaccine straties in vivo for delivery of protein antigen or antigen-encoding DNA and mRNA by virulence-attenuated *Listeria monocytogenes*." *Infect Immon.* Jul;74(7).3946-57.
Loessner et al. (1996) "Heterogeneous endotysins in *Listeria monocytogenes* bacteriophages: a new class of enzymes and evidence for conserved holin genes within the siphoviral lysis cassettes," *Mol Mictiobiol.* Jun;16(6):1231-41.
Loessner at al. (2000) "Complete nucleotide sequence, molecular analysis and genome structure of bacterlopisage A118 of *Listeria monocytogenes*: implications for phage evolution," *Molecular Microbiology* 35(2):324-40.
Makela et al. (1997) Hand Book of Experimental Immunology, vol. 1, chapter 3, pp. 3.1-3.13.
Mandal et al. (2002) "Listeriolysin O-liposome-mediated cytosolic delivery of macromolecule antigen in vivo; enhancement of antigen-specific cytotoxic T lymphocyte frequency, activity, and tumor protection." *BBA* 1563 7-17.
Manjili et al. (2003) "HSP110-HER2/neu chaperone complex vaccine induces protective immunity against spontaneous mammary tumors in HER-2/neu transgenic mice," *J Immunol.* Oct. 15,171(8):4054-81.
Marquis et al. (1997) "Proteolytic pathways of activation and degradation of a bactertat phuspnolipase C during intracellular infection by *Listeria monocytogenes*." *J. Cell Biol.* 137:1381-1392.
Mart irkt at at (1986) "Nucleotide sequence of the tetM tetracycline ressstance determinant of the streptococcal conjugative shuttle transposon Tn1545." *Nucleic Acid Res.* 14:7047-7058.
Marx et al. (2002) "Broad-host-range cre-lox system for antibiotic marker recycling in gram-negative bacteria." *Biotechniques.* Nov;33(5):1082-7.
McLaughlan et at (1998) "Molecular characterization of an autolytic ernidese of *Listeria monocytogenes* EGD." *Microbiology.* May,144(Pt 5):1359-67.
Mengaud at al. (1986) "Expression in *Escherichia coli* and sequence analysis of the Listeriolysin O determinant of *Listeria monocytogenes*" *Infection and Immunity* 56(4):765-772.
Mikayama et al. (1993) "Molecular cloning and functional expression of a CDNA encoding gycosylation-inhibiting factor" *Proc. Natl. Acad. Sci. USA* 90:10056-10060.

Mlynarova et al, (2002) "The promiscuity of heterospecific lox sites increases dramatically inthe presence of patindromic DNA." *Gene.* Aug. 21;296(1-2)129-37.
Mollet et al. (1993) "Directed genomic integration, gene replacement, and integrative gene expression in *Streptococcus thermophilus*," *J. Bacteriology* 175:4315-4324.
Moriishi et al. (1998) "Sequence analysts of tne actA gene of *Listeria monocytogenes* isolated from human" *Microbiol. Immunol.* 42(2):129-132.
Ngo et al. (1994) The Protein Folding Problem and Tertiary Strucaure Prediction. 492-495.
Ochsensein et el. (1999) "A comparison of T cell memory against the same antigen induced by virus versus intracellular bacteria," *Proc Natl Acad Sci USA.* Aug. 3:96(16);9293-8.
Oscarsson et al. (1996) "Induction of haemolytic activity in *Escherichia coli* by the siyA gene product." *Mol Microbiol.* Apr,20(1):191-9.
Paglia at at (1997) "The defined attenuated *Listeria monocytogenes* delta mp12 mutant is an effective oral vaccine carrier to trigger a long-lasting immune responise against a mouse fibrosarcoma" *Eur J Immunol* 27:1570-1575.
Palmeros et al. (2000) "A family of removable cassettes designed to obtain antibiotic-resistance-free gertamic modifications of *Escherichia coli* and other bacteria," *Gene*, Apr. 18:247(1-2):255-64.
Pan (1999) "Regression of established B16F10 melanoma with a recombinant *Listeria monocytogenes* vaccine." *CancerRes* 59(20)6264-5289.
Pan et al. (1995) "A recombinant *Listeria monocytogenes* vaccine expressing a model tumour antigen protects mice against lethal tumour cell challenge and causes regression of established tumours." *Nature Med.* 1;471-477.
Pan et al. (1995) "Regression of established tumors in mice mediated by the oral administration of a recombinant *Listeria monocytogenes* vaccine" *Cancer Res* 55:4776-4779.
Parida et al. (1993) "Internalin B is essential for adhesion and mediates the invasion of *Listeria monocytogenes* into human endothelial cells." *Mol Microbiol.* Apr;28(1):81-93.
Paul et at. (1939) "Fundamental Immunology", Second Edition, Raven Press, 967-988.
Peng at al. (2004) "The ability of two *Listeria monocytogenes* vaccines targeting human papillornavirus-16 E7 to induce an antitumor response correlates with myeloid dendritic cell function." *J. Immunol.* 172:6030-6038.
Penichet et al. (2001) "Antibody-cytokine fusion proteins for the therapy of cancer." *J. Immunological Methods* 248:91-101.
Peters et at. (2403) "Tailoring host immune responses to *Listeria* by manipulation of virulence genes—the interface between innate and acquired immunity." *FEMS Immunol Med Microbiol.* Apr. 1;35(3):243-53.
Pfeifer et al. (1993) "Phagocyte processing of bacterial antigens or class I MHC presentation to T cells" *Nature.* Jan. 28;361(6410):359-62.
Pupa et al. (2001) "Prevention of spontaneous neu-expressing mammary tumor development in mice transgenic for rat proto-neu by DNA vaccination." *Gene Ther.* Jan;8(1):75-9.
Quénée et al. (2005) "Combined sacB-based negative selection and cre-lox antibiotic marker recycling for efficient gene deletion in pseudomonas aeruginosa" *Biotechniques.* Jan:38(1):63-7.
Radford et al. (2002) "A recombinant *E. coil* vaccine to promote MHC class I-dependent antigen presentation: application to cancer immunotherapy." *Gene Therapy* 9:1465-1463.
Radford el at. (2003) "Recombinant *E. coil* efficiently delivers antigen and maturation signals to human dendritic cells: presentation of MART1 to CD8+ T cells." *Int J. Cancer* 105:811-619.
Raveneali et al. (1992) "Reduced virulence of a *Listeria monocytogenes* phospholipase-deficient mutant obtained by transposon insertion into the zinc metalloprotease gene," *Infect. Immun.* 60:916-921.
Realini et al, (1994) "KEKE motifs. Proposed roles in protein-protein association and presentation of peptides by MHC class I receptors" *FEBS Letters* 348:109-113.
Rechsteiner at al. (1996) "PEST sequences and regulation by proteolysis" *TIBS* 21:267-271.

(56) References Cited

OTHER PUBLICATIONS

Reiter at al, (1969) "Transfer RNA genes frequently serve as integration sites for prokaryotic genetic elements," *Nucleic Acids Research* 17(5)1907-14.
Renard at al (2003) "HER-2 DNA and protein vaccines containing potent Th cell epitopes induce distinct protective and therapeutic antitumor responses in Her-2 transgenic mice." *J Immunol.* 171(3):1588-95.
Repique (1992) "Immunosuppression derived from human B-lymphoblastoid and melanoma cell lines." *Cancer Invest.* 10(3):201-208.
Roden et al. (2004) "Vaccination to prevent and treat cervical cancer." *Hum Pathol* 35(8):971-82.
Rüssmann et al. (1998) "Delivery of epitopes by the *Salmonella* type III secretion system for vaccine development." *Science.* Jul. 24;281(5376):555-8.
Fley at al, (1991) "Role of Listariolysin-o (LLO) in the T Lymphocyte response to infection *Listeria monocytogenes*" *J Immunol*, 146(10):3804-3816.
Schafer at al. (1992) "Induction of a cellular immune response to a foreign antigen by a recombinant *Listeria monocytogenes* vaccine," *J. Immunol.* 149(1):53-59.
Scheirlinck et al. (1989) "Integration and expression of alpha-amylase and endoglucariase genes in the *Lactobacillus plantarum* chromosome." *Appl Environ Microbiol* 56(9)1130-7.
Schmidt at al. (1995) "Molecular Analysis of the Plasmid-Encoded Hemolysin of *Escherichia coli* O157:H7 Strain EDL 933" *Infection and Immunity*, S3(2):1056-1061.
Scortti et al. (2007) "The PrfA virulence regulon." *Microbes Infect.* Aug: (10):1196-207.
Sewell et al. (2004) "Regression of HPV-positive tumors treated with e new *Listeria monocytogenes* vaccine." *Arch Otolaryngol Head Neck Surg* 130:92-97.
Sewell et al. (2004) "Recombinant *Listeria* vaccines containing PEST sequences are potent immune adjuvants tar the tumor-associated antigen human papillornavinis-16 E7." *Cancer Res.* Dec 15.64(24):8821-5.
Shen et at. (1995) "Recombinant *Listeria monocytogenes* as a live ive vaccine vehicle for the induction of protective anti-viral cell-mediated immunity." *Proc Nat'l Acad Sci U S A.*92(9):3987-91.
Shen et al (1998) "*Listeria monocytogenes* as a probe to study cell-medlated immunity" *Curr Opin. Immunol.* 10(4):450-458.
Shen et al. (1998) "Compartmentalization of bacterial antigens: differential effects on priming of CD8 T cells and protective immunity," *Cell.* Feb. 20:92(4):535-45.
Shetron-Rama et al (2002) "Intracellular induction of *Listeria monocytogenes* actA expression." *Infect. Immun.* 70:1087-109S.
Shimizu et al (1994) "Effects of CD4+ and CDB+ T Cells tumor-bearing mice on antibody production" *Cancer Immunol Immunother.* 38(4):272-276.
Singh et al. (2005) "Fusion to Listeriotysin O and delivery by *Listeria monocytogenes* enhances the immunogenicity of HER-2/neu and reveals subdominant epitopes in the FVB/N mouse." *J Immunol.* Sep. 15:175(6):5663-73.
Sirard et al. (1997) "Intracytoplesrnic delivery of Listertolysin O by a vaccinal strain of *Bacillus anthracis* induces CD8-mediated protection against *Listeria monocytogenes*" *J Immun.* 159:4435-4443.
Skoble, J. et al. (2000). "Three regions within acta promote arp2/3 complex-mediated actin nucleation and *Listeria monocytogenes* motility" *The Journal of Cell Biology* 150(3):527-537.
Skolnick et al. (2000) "From genes to protein structure and function: novel applications of computational approached in the genomic era" *Trends in Biotech.* 18(1):34-39.
Slifka at ai, (1996) "Antiviral cytotoxic T-cell memory by vaccination with recombinant *Listeria monocytogenes*," *J. Virol.* 70(5):2902-10.
Smith et at, (1995) "The two distinct phospholipases C of *Listeria monocytogenes* have overlapping roles in escape from a vacuole and cell-to-cell spread." *Infect Immun.* 63 4231-4237.
Smith et al. (1995) "Asymmetric Distribution of the *Listeria monocytogenes* ActA Protein is Required and Sufficient to Direct Actin-Based Motility" *Molecular Microbiology* 17:945-951.
Souders at al. (2006) "In vivo bactofection: listeria can function as a DNA-cancer vaccine." *DNA Cell Biol.* Mar;26(3);142-51.
Stahl et al. (1984) "Replacement of the *Bacillus subtilis* subtilisin structural gene with an in vitro-derived deletion mutation," *J. Bacteriol* 158:411-418.
Starks et al. (2004) "*Listeria monocytogenes* as a vaccine vector: virulence attenuation or existing antivector immunity does not diminish therapeutic efficacy," *J. Immunology* 173:420-427.
Stitz et al. (1990) "Characterization and immunological properties of influenza A virus nucleoprotein (NP): cell-associated NP isolated from infected cells or viral NP expressed by vaccinia recombinant virus do not confer protection." *J Gen Virol.* 71(Pt 5):1169-1179.
Strugnell et al. (1990) "Statile expression of foreign antigens from the chromosome of *Salmonella typhimurium* vaccine strains." *Gene* 88:57-83.
Stryer et al. (1998) Biochemistry, Third Edition, WH Freeman Company, New York, 31-33.
Sun et al. (1990) "Isolation of *Listeria monocytogenes* small-plaque mutants defective for intracelluter growth and cell-to-cell spread." *Infect Immun.* 58 3770-3778.
Tanabe et al. (1999) "Induction of Protective T Cells against *Listeria monocytogenes* in Mice by immunization with a Listeriolysin O-Negative Avirulent Strain of Bacteria and Liposome-Encapsulated Listeriolysin O" *Infect. Immun.* 67(2):566-575.
Tilney et al. (1989) "Actin filaments and the growth, movement, and spread of the intracellular bacterial parasite, *Listeria moncytogenes*," *J Cell Biol.* Oct;109(4 Pt 1)1597-608.
Vasil et al. (1982) "Cloning of a phosehate-regulated hemolysin gene (phospholipase C) from *Pseudomonas aertiginosa.*" *J Bacteriol.* Oct;152(1)A31-40.
Vazquez-Boland et al. (1992) "Nucleotide sequence of the lecithinase operon of *Listeria monocytogenes* and possible role of lecithinase in cell-to-cell spread." *Infect. Immun.* 60:219-230.
Verch et al. (2004) "*Listeria monocytogenes*-based antibiotic resistance gene-free antigen delivery system applicable to other bacterial vectors and DNA vaccines." *Infect Immun.* Nov;72(11):6416-25.
Verma et al. (1995) "Delivery of class I and class II MHC-restricted T-cell epitopes of listeriolysin of *Listeria monocytogenes* by attenuated *Salmonella*", *Vaccine* 13(2):142-150.
Walker at al. (1994) "Tumor growth alters T cell and macrophage production of and responsiveness to granulocyte-maorophage colony-stimulating factor: partial dysregulation through interleukin-10." *Cell Immunol.* 154(1):342-357.
Watson et al. (1991) "Splenic macrophages from tumor-bearing mice co-expressing MAC-1 and MAC-2 antigens exert immunoregulatory functions via two distinct mechanisms." *J. Leukoc Biol.* 49(2): 126-138.
Wei et al. (2005) "*Listeria monocytogenes* phosphatidylinositol-specific phospholipase C has evolved for virulence by greatly reduced activity on GPI anchors." *Proc. Natl. Acad. Sci. USA* 102:10927-12931.
Weidt et al, (1994) "CD8+ T lymphocyte-mediated antiviral immunity in mice as a result of injection of recombinant viral proteins." *J Immunol.* Sep. 15;153(6)2554-61.
Weiskirch et al. (1997) "*Listeria monocytogenes*: a potent vaccine vector for neoplastic and infectious disease." *Immunologcal Reviews* 158:159-189.
Welch at al. (1998) "Interaction of Human Afrp2/3 Complex and the *Listeria monocytogenes* ActA Protein in Actin Filament Nucleation" *Science* 261:105-108.
Wirth et al. (1986) "Highly efficient protoplast transformation system for *Streptococcus faecalis* and a new *Escherichia coil-S. faeaatis* shuttle vector." *J Bacteriol.* 165(3):831-8.
Wu et al. (1995) "Engineering an intracellular pathway for major histocompatibilily complex class II presentation of antigens" *Cancer Res.*, 56:21-26.
Young et at (1992) "Tumor-derived cytokines induce bone marrow suppressor cells that mediate immunosuppression through transforming growth factor beta." *Cancer Immunol Immunother*, 35(1): 14-18.

(56) References Cited

OTHER PUBLICATIONS

Young et al. (1995) "Holins form and function in bacteriophage lysis." *FEMS Microbiol Rev.* Aug;17 (1-2): 191-205.
Zhang et al. (1993) "Functional replacement of the nemolysin A transport signal by a different primary sequence." *Proc. Natl. Acad Sci U S A.* May 1;90(9):4211-5.
Abachin et al., "Formation of D-alanyl-lipoteichoic acid is required for adhesion and virulence of *Listeria monocytogenes*", Molecular Microbiology, 2002, 43(1), 1-14.
Aggarvval et al., "Oral *Salmonella*: Malaria Gircumsporozoite Recombinants induce Specific CD8+ Cytotoxic T Cells", J. Exp. Med. 1990, 172, 1083-1090.
Alexander et al , "Characterization of an aromatic amino acid-dependent *Listeria monocytogenes* mutant attenuation, persistence, and ability to induce protective immunity in mice", infection and immunity, May 1993, p. 2245-2248.
Amici et al., "DNA vaccination with full-length or truncated Neu induces protective immunity against the development of spontaneous mammary tumors in HER-2/neu transgenic mice", Gene Therapy, 2000, 7, 703-706.
Angelov et al., "Therapeutic vaccine for acute and chronic motor neuron diseases: Implications for amyotrophic lateral sclerosis", PNAS, Apr. 2003, vol. 100, No. 8, 4790-4795.
Anido et al., "Biosynthesis of tumorigenic HER2 C-terminal Fragments by alternative initiation of translation", The EMBO Journal, 2006, 25, 3234-3244.
Bai et al., "Antigenic drift as a mechanism for tumor evasion of destruction by cytplytic T lymphocytes", J. Clin. Invest., 2003, 111, 1487-1496.
Bast et al., "Antitumor activity of bacterial infection: I. Effect of *Listeria monocytogenes* on growth of a murine fibrosarcoma", J. Natl. Cancer Inst., 54:749-756, 1975.
Baxeranis et al., "Immunobiology of HER-2/neu oncoprotein and its potential application in cancer immunotherapy", Cancer Immunol. Immunother., 2004, 53, 166-175.
Beattie et al., "Cloning and characterization of T-cell-reactive protein antigens from *Listeria monocytogenes*", Infect. Immun., Sep. 1990; 58(9):2792-803.
Beatty, "A dual role for IFN-gamma in resolving the balance between tumor prouression and regression", University of Pennsylvania, 2001, ii-xiii, pp. 1-10, AAT 9989557, UMI No. 9989567, Bell and Howell Information and Learning Company, Ann Arbor, Michigan.
Bergmann et al., "The neu oncogene encodes an epidermal growth factor receptor-related protein", Nature, vol. 319, Jan. 1986, 226-230.
Biragyn et al., "Models for Lymphoma", Current Protocols in Immunology, 2001, 20.6.1-20.6.30.
Boon et al., "Tumor Antigens Recognized by T Lymphocytes", Annu Rev. Immunol. 1994,12, 337-365.
Bouwer et al., "Acquired immunity to an intracellular pathogen: immunologic recognition of *L. monocytogenes*-infected cells", Aug. 1997;158.137-46.
Bouwer et al., "Cytotoxic-T-lymphocyte responses to epitopes of listeriolysin O and p60 following infection with *Listeria monocytogenes*", Infect. Immun., Jul. 1996; 64(7):2515-22.
Bowie et al., "Deciphering the message in protein sequences: tolerance to amino acid substitutions", Science 247:1306-1310, 1990.
Bron et al., "Use of the alr gene as a food-grade selection marker in lactic acid bacteria", Applied and Environmental Microbiology, Nov. 2002, vol. 68, No. 11, p. 5663-5670.
Bruder et al., "Efficient induction of cytotoxic CD8+ T cells against exogenous proteins. establishment and charcterization of a T cell line specific for the membrane protein ActA of *Listeria monocytogenes*", Eur. J. Immunol., Sep. 1998, 28(9):2630-9.
Brunner et al., "Quantitative assay of the lytic action of immune lymphoid cells on cr-labelled allogeneic target cells in vitro; inhibition by isoantibody and by drugs", Immunology, 1968, 14, 181-196.
Camilli et al, "*Listeria monocytogenes* mutants lacking phosphatidylinositol-specific phospholipase C are avirulent", J. Exp. Med., vol. 173, 751-754, Mar. 1991.
Catic et al., "Introduction of protein or DNA delivered via recombinant *Salmonella typhimurium* into the major histocompatibility complex class I pesentation pathway of macrophages", Microbes Infect., Feb. 1999, 1(2):113-21.
Chazin et al., "Transformation mediated by the human Her-2 gene independent of the epidermal growth factor receptor", Oncogene, 1992, 7, 1859-1866.
Cheever et al., "T-Cell Immunity to Oncogeneic Proteins Including Mutated RAS and Chimeric BCR-ABL", *Ann. N.Y. Acad. Sci.* 1993 690:101-112.
Chen et al., "DNA Vaccines Encoding Full-Length or Truncated Neu Induce Protective Immunity against New-expressing Mammary Tumors", Cancer Research 58, 1965-1971, May 1, 1998.
Cho et al., "Structure of the extracellular reaion of HER2 alone and in complex with the herceptin Fab", Nature, vol. 421, Feb. 2003, 756-760.
Ciurea et al , "Viral persistence in vivo through selection of neutralizing antibody-escape variants", PNAS, Mar. 2000, vol. 97, No. 6, 2749-2754.
Cohen, J "Cancer vaccines get a shot in the arm", Science 262:841-843.
Concetti et al., "Autoantibody to P185$^{erbB2/neu}$ oncoprotein by vaccination with xenogenic DNA", Cancer Immunol. Immunother., 1996, 43, 307-315.
Coussens et al., "Tyrosine kinase receptor with extensive homology to EGF receptor shares chromosomal location with neu oncogene", Sceince, vol. 230, 1132-1139, Dec. 1985.
Darji et al., "Antigen-specific T cell receptor antagonism by antigen-presenting cells treated with the hemolysin of *Listeria monocytogenes*: a novel type of immune escape", Eur. J. Immunol., Jul. 1997; 27(7):1696-703.
Darji et al., "T-cell anergy induced by antigen presenting cells treated with the hemolysin of *Listeria monocytogenes*", Immunol. Lett., Jun. 1997; 57(1-3):33-7.
Darji et al,, "The role of the bacterial membrane protein ActA in immunity and protection against Listeria monocytogenes", J. Immunol., Sep. 1, 1998; 161(5):2414-20.
Di Carlo et al., "Inhibition of Mammary Carcinogenesis by systemic interleukin 12 or P185$^{neu}$ DNA vaccination in HER-2/neu transgenic BALB/c mice", Clinical Cancer Research, Mar. 2001, vol. 7, 830s-837s.
Disis et al,. "Effect of dose on immune response in patients vaccinated with an her-2/neu intracellular domain protein-based vaccine", Journal of Clinical Oncology, vol. 22, No. 10, May 2004, 1916-1925.
Disis et at, "Generation of T-cell Immunity to the HER-2/neu Protein After Active Immunization with HER-2/neu Peptide-Based Vaccines", J Clin. Oncol. 20:2624-2632, 2002.
Disis et al., "Her-2/neu protein: a target for antigen-specific immunotherapy of Human Cancer", Adv Cancer Res 71:343-371,1997.
Disis et al., "Immunity to the HER-2/neu oncogenic protein", Ciba Found, Symp. 1994 187:198-211.
Disis et at, "Peptide-Based, but not whole protein, vaccines elicit immunity to HER-2/neu, an oncogenic self-protein", The Journal of Immunology, 1996, 156:3151-3158.
Doling et al., "Cytotoxic T-lymphocyte epitopes fused to anthrax toxin induce protective antiviral immunity", Infect. Immun., Jul. 1999, 67(7):3290-6.
Dumitrescu et al., "Understanding breast cancer risk—where do we stand in 2005?", J. Cell. Mol. Med., vol. 9, No 1, 2005, pp. 208-221.
Dunn et al., "A critical function for type I interferons in cancer immunoediting", vol. 6, No. 7, Jul. 2005, Nature Immunology, 722-729.
Dunn et al., "Cancer immunoediting from immunosurveillance to tumor escape", Nature Immunology, vol. 3, No. 11, Nov. 2002, 991-998.
Dunn et al., "Interferon-γ and cancer Immunoediting", Immunologic Research, 2005, 32/1-3: 231-245.
Dunn, "The Immunobiology of cancer Immunosurveillance and Immunoediting", Immunity, Aug. 2004, vol. 21, 137-148.
Ercolini et al., "Recruitment of latent pools of high-avidity CD8+ T cells to the antitumor immune response", JEM, vol. 201, No. 10, May 2005, 1591-1602.

(56) References Cited

OTHER PUBLICATIONS

Esserman et al., "Vaccination with the extracellular domain of P185$^{neu}$ prevents mammary tumor development in neu transgenic mice", Cancer Immunol. Immunother., 1999, 47, 337-342.
Fields, "Preparation of antipeptide antibodies—Introduction to peptide synthesis", Current Protocols in Molecular Biology, 2002, 11.15.1-11.15.9.
Finn et al., "MUC-1 Epithelial Tumor Mucin-Based Immunity and Cancer Vaccines", Immuno. Rev. 1995, 145:61-89.
Foy et al., "Vaccination with HER-2/neu DNA or protein subunits protects against growth of HER-2/neu—expressing murine tumor", Vaccine, 19, 2001, 2598-2606.
Freshney, "Culture of animal cells—a manual of basic technique", Chapter 1, Second Edition, 1983, 1-6.
Gallo et al., "Xenogeneic immunization in mice using HER2 DNA delivered by an adenoviral vector". Int J. Cancer, 113, 67-77, 2005.
Gansbacher et al., "Interleukin 2 Gene Transfer into Tumor Cells Abrogates Tumorigenicity and Induces Protective Immunity", J. Exp. Med. 1990, 172, 1217-1224.
Garay-Malpartida et al., "Caspredictor: a new computer-based tool for caspase substrate prediction", Bioinformatics, vol. 21, suppl. 1, 2005, p. 169-176.
Garcia-Lora et al., "MHC class I-deficient metastatic tumor variants immunoselected by T lymphocyes orginate fom the corrdinated downegulation of Apm components", Int J Cancer 106, 521-527, 2003.
Gillespie et al., "The potential of melanoma antigen expression in cancer therapy", Cancer Treat. Rev. 1999, 25(4):219-27.
Glenting et al., "A plasmid selection system in lactococcus lactis and its use for gene expression in L lactis and human kidney fibroblasts", Applied and Environmental Microbiolooy, Oct. 2002, vol. 68, No. 10, P. 5051-5056.
Golsteyn et al., "Structural and functional similarities between the human cytoskeletal protein zyxin and the ActA protein of Listeria monocytogenes", J. Cell Sci. 110:1893-1906, 1997.
Golumbek et al., "Treatment of Established Renal Cancer by Tumor Cells Engineered to Secrete Interleukin-4", Science 1991, 254, 713-716.
Gregory et al., 1997, "Internalin B promotes the replication of Listeria monocytogenes in mouse hepatocytes", Infect. lmmun. 65(12):5137-41.
Gritzapis et al., "Vaccination with Human HER-2/neu (435-443) CTL peptide induces effective antitumor immunity against HER-2/neu -expressing tumor cells in vivo", Cancer Res., 66, 10, May 2006, 5452-5460.
Gunn, "Recombinant Listeria monocytogenes as a tumor therapeutic", Univ. of Pennsylvania—Electronic Dissertation. Paper AAI3015316, UMI Microform 3015316, 2001, pp. v-vi, Bell and Howell Information and Learning Company, Ann Arbor, Michigan, abstract.
Guy et al., "Expression of the neu proto oncogene in the mammary epithelium of transgenic mi e induces metastatic disease", Proc. Natl. Aced Sci. USA, Nov, 1992, vol. 89, pp. 10578-10582.
Harris et al., "Molecular Basis for Hetreogeneity of the Human p53 protein", Molecular and Cellular Biology, Dec. 1986, vol. 6. No. 12, p. 4650-4656.
Harty et al., "CD8 T lymphocytes specific for the secreted p60 antigen protect against Listeria monocytogenes infection", J. Immunol., May 1, 1995; 154(9):4642-50.
Hess et al., "Live antigen carriers as tools for improved anti-tuberculosis vaccines", FEMS Immunol. Med. Microbiol., Feb. 1999, 23(2), 165-73.
Higgins et al., "Delivery of protein to the cytosol of macrophages using Escherichia coli K-12", Mol, Microbiol., Mar. 1999, 31(6):1631-41.
Hiltbold et al., "Mechanisms of processing and presentation of the antigens of Listeria monocytogenes", Infect. Agents Dis., Oct. 1993; 2(5):314-23.
Hiltbold et al., "The presentation of class I and class II epitopes of listeriolysin O is regulated by intracellular localization and by intracellular localization and by intercellular spread of Listeria monocytogenes", J. Immunol., Aug. 1996; 157k3):1163-75.
Hoogenboom et al., "By passing Immunisation—human antibodies from synthetic repertoires of germline $V_H$ gene segments rearranged in vitro", J. Mol. Biol , 1992, 227, 381-388.
Hueman et al., "Phase I clinical trial of a HER-2/neu peptide (E75) vaccine for the prevention of prostate—specific antigen recurrence in high-risk prostate cancer patients", Clin. Cancer Res., 11(20), Oct. 2005, 7470-7479.
Ikonomidis et al., "Influenza-specific immunity induced by recombinant Listeria monocytogenes vaccines", Vaccine, vol. 15, No. 4, pp. 433-440, 1997.
Ikonomidis et al., "Recombinant Listeria monocytogenes Cancer Vaccines", Vaccine 95, 1995, 95:317-326.
Ikonomidis et al., ASM Las Vegas, The 94$^{th}$ General Meeting of the American Society for Microbiology, May 23-27, 1994, Las Vegas Convention Center, Las Vages, Nevada, p. 29, 159, 662, 664.
International Search Report of Application No. PCT/U501/09736 dated Jul. 27, 2001.
International Search Report of Application No. PCT/US05/32682 dated Jun. 1, 2006.
International Search Report of Application No, PCT/US07/06292 dated Jun. 17, 2008.
International Search Report of Application No. PCT/US07/10635 dated Sep. 11, 2008.
International Search Report of Application No. PCT/US08/03067 dated Aug. 29, 2008.
International Search Report of Application No. PCT/US08/06048 dated Nov. 20, 2008.
International Search Report of Application No. PCT/US95/14741 dated Feb. 15, 1996.
Jenson et al., "Recombinant Listeria monocytogenes as a live vaccine vehicle and a probe for studying cell-mediated Immunity", Immunological Review, vol. 158, 147-157.
Kawashima et al., "The Multi-epitope Approach for Immunotberapy for Cancer: Identification of Several CTL Epitopes from Various Tumor-Associated Antigens Expressed on Solid Epithelial Tumors", Hum. Immunol. 1998 59:1-14.
Khong et al., "Identification of multiple antigens recognized by tumor-infiltrating lymphocytes from a single patient: Tumor escape by antigen loss and loss of MHC expression", J. Immunother., 2004, 27, 184-190.
King et al., "Amplification of a Novel v-erbB-related gene in a human mammary carcinoma", Science, Sep. 1985, vol. 229, 974-976.
Kohler et al., "Expression of the iap gene coding for protein p60 of Listeria monocytogenes is controlled on the posttranscriptional level", Journal of Bacteriology, Aug. 1991, vol, 173, No. 15, p. 4668-4674.
Kruisbeek, "In vivo depletion of CD4– and CD8-specific T cells" Current Protocols in Immunology, John Wiley & Sons, Inc., eds., 1991, V.1, 4.1.1-4.1.2.
Kumar et al., "Amino acid variations at a single residue in an autoimmune peptide profoundly affect its properties- T-cell activation, major histocompatibility complex binding, and ability to block experimental allergic encephalomyelitis", PNAS, 87:1337-1341, 1990.
Kuntson et al., "Neu antigen negative variants can be generated after neu-specific antibody therapy in neu transgenic mice", Cancer Research 64, Feb. 2004, 1146-1151.
Kuntson et al., "Immunization with a HER-2/neu helper peptide vaccine generates HER-2/neu CD8 T-cell immunity in cancer patients", The Journal of Clinical Investigation, 107:477-484,2001.
Kyte et al., "A simple method for displaying the hydropathic character of a protein", J. Mol. Biol., 1982, 157, 105-132.
Lacey et al., "Phase IIa safety and immunogenicity of a therapeutic vaccine, TA-GW, in persons with genital warts", The Journal of Infectious Diseases, 1999, 179:612-8.
Lauer et al., "Systematic mutational analysis of the amino-terminal domain of the Listeria monocytogenes ActA protein reveals novel functions in actin-based motility", Molecular Microbiology 42(5):1163-1177, 2001.

(56) References Cited

OTHER PUBLICATIONS

Lee et al., "Delivery of macromolecules into cytosol using liposomes containing hemolysin from *Listeria monocytogenes*", J. Biol. Chem., Mar. 29, 1996; 271(13):7249-52.
Lee et al., "The murine MHC class I genes. H-2D and H-2L, and two genes reported to encode tumor-specific antigens", J. Exp. Med., Nov. 1988, vol. 168, 1719-1739.
Leitner et al., "DNA and RNA-based vaccines: prinicples, progress and prospects", Vaccine, Dec. 1999, 18(9-10):765-777.
Lifford et al., "Vaccination with immunociorninant peptides encapsulated in Quil A-containing liposomes induces peptide-specific primary CD8+ cytotoxic T cells", Vaccine, Jan. 1994; 12(1):73-80.
Liu, "Vaccine developments", Nature Medicine Vaccine Supplement, May 1998, vol. 4, No. 5, 515-519.
Marks et al., "By-Passing immunization human antibodies from V-gene libraries displayed on phage", J. Mol. Biol. 1991, 222, 581-597.
Mata et al., "Evalution of a recombinant *Listeria monocytogenes* expressing an HIV protein that protects mice against viral challenge", Vaccine, 19, 2001, 1435-1445.
Mazzaccaro et al., "Major histocompatibility Class I presentation of soluble antigen facilitated by *Mycobacterium tuberculosis* infection", Proc. Natl. Acad. Sci. USA; Oct. 15, 1996; 93 21 :11786-91.
McCarty et al., "Targeting p53 for Adoptive T-Cell Immunotherapy", Cancer Research 1998, 15:58 2601-5.
McKaig et al., "Human Papillomavirus and Head and Neck Cancer: Epidemiology and Molecular Biology", Head Neck 1998, 20 (3):250-65.
Mengaud et al., "Expression in *Escherichia coli* and sequence analysis of the Listeriolysin O determinant of *Listeria monocytogenes*", Infect. Immun., vol. 56, No. 4, 766-712, 1988.
Miller et al., "Targeted vectors for gene therapy", The FASEB Journal, Feb. 1995, vol. 9, p. 190-199.
Muller, "Expression of activated oncogenes in the murine mammary gland: transgenic models for human breast cancer", Cancer and Metastasis Reviews, 10:217-227, 1991.
Murali et al., "Structural analysis of P185$^{c-neu}$ and epidermal growth factor receptor tyrosine kinases: oligomerization of kinase domains", Proc. Natl. Acad. Sci. USA, vol. 93, pp. 6252-6257, Jun. 1996, Biochemistry.
Naz et al., "Novel human prostate-specific cDNA: molecular cloning, expression, and nobiology of the recombinant protein", Biochemical and Biophysical Research Communications 297, 2002, 1075-1084.
Neeson e al., "A DNA prime-oral listeria boost vaccine in rhesus macaques induces a SIV-specific CD8 T cell mucosal response characterized by high levels of α4β7 integrin and an effector memory phenotype", Virology, Oct. 2006, 354(2), 299-315.
Neeson et al , "Listeriolysin O is an improved protein idiotype and provides systemic protection against 38c/3 lymphoma", Cancer Immunol. Immunother., 2007, 13 pages.
Nielsen et al., "Peptide nucleic acids as therapeutic agents", Nucleic acids, p. 353-357, Curr Opinion Struc Biol 9(3): 353-7, Jun. 1997.
Pagano, J.S., "Epstein-Barr Virus: The First Human Tumor Virus and its Role in Cancer", Proc. Assoc. Am. Physicians 1999 111(6):573-80.
Pardoll, "Cancer Vaccines", Nature Medicine Vaccine Supplement, May 1998, vol. 4, No. 5, 525-531.
Paterson et al., "Recombinant *Listeria monocytogenes* cancer vaccines", Curr Opin Immunoi. 1996 Oct;8(5) 664-669.
Paterson et al., Proceedings of the American Association for Cancer Research, Mar. 2000. 41:890, abstract # S25.
Paterson, "Rational approaches to immune regulation", Immunogenic Research, 27(2-3).451- 462, Jun. 2003.
Piechocki et al., "Complementary Antitumor Immunity Induced by Plasmid DNA Encoding Secreted and Cytoplasmic Human ErbB-2", The Journal of Immunology, 2001, 167:3367-3374.
Pilgrim et al., "Bactofection of mammalian cells by *Listeria monocytogenes*: improvement and mechanism of DNA delivery", Gene Therapy, 2003, 10, 2036-2045.

Pilon et al., "Vaccination with Crytoplasmic ErbB-2 DNA Protects Mice from Mammary Tumor Growth Without Anti-ErbB-2 Antibody", The Journal of Immunology, 2001, 167:3201-3206.
Pricher et al., "Viral escape by selection of cytotoxic T cell-resistant virus variants in vivo", Nature, vol. 346. Aug. 1990, 629-633.
Pucci et al,, "*Straphylococcus hameolyticus* contains a glutamate racemase and a D-amino acid transaminase", Journal of Bacteriology, Jan. 1995, vol. 177, No. 2, p. 336-342.
Punwaney et al., "Human Papillomavirus May be Common within Nasopharyngeal Carcinoma of Caucasian Americans: investigation of Epstein-Barr virus and human papillomavirus in Easter and Western Nasopharyngeal Carcinoma using Ligation-Dependent polymerase chain reaction", Head Neck, 1999, 21(1):21-9.
Raffaghello et al., "Multiple defects of the antigen-processing machinery components in human neuroblastoma: immunotherapeutic implications", Oncogene, 2005, 24, 4634-4644.
Reilly et al., "HER-2/neu is a tumor rejection target in tolerized HER-2/neu transgenic mice", Cancer Research 60, 3569-3576, Jul. 2000.
Restifo et al., "identification of Human Cancers Deficient in Antigen Processing", J. Exp. Med. 1993, 177, 265-272.
Restifo et al., "The promise of nucleic acid vaccines", Gene Ther , Jan. 2000, 7(2): 89-92.
Rogers et al., "Amino acid sequences common to rapidly degraded pro is: the PEST hypothesis", Science, Reports, Oct. 1986, vol. 234, 364-368.
Romero et al., "Coordinated downregulation of the anti gen presentation machinery and HLA class 1/β2-microglobulin complex is responsible fo HLA-ABC loss in bladde cancer", Int. J. Cancer, 2005, 113, 605-610.
Rovero et al., "DNA Vacciniation Against Rat Her-2/Neu p185 More Effectively inhibits Carcinogenesis Than Transplantable Carcinomas in Transgenic BALB/c Mice", The Journal of Immunology, 2000, 165:5133-5142.
Scardino et al., "Her-2/neu and hTERT cryptic epitopes as Novel targets for broad spectrum tumor Immunotherapy", The Journal of Immunology, 2002, 168:5900-5906.
Schlom et al., "Cancer Vaccines:Moving Beyond Current Paradigms", Clin. Cancer Res. 2007; 13(13), Jul. 1, 2007.
Schmidt et al., "Molecular Analysis of the Plasmid-Encoded Hemolysin of *Escherichia coli* O157:H7 Strain EDL 933", Infection and Immunity, 63(3):1055-1061, 1995.
Schneider et al., "Induction of pulmonary allergen-specific IgA responses or airway hyperresponsiveness in the absence of allergic lung disease following sensitization with limiting doses of ovalbumin-alum", Cellular Immunology, 212, 101-109, 2001.
Schnupf et al., "Phosphorylation, ubiquitination and degradation of listeriolysin O in mammalian cells: role of the PEST-like sequence", Cellular Microbiology 8(2):353-364, 2006.
Schwartz, "T cell energy". Annu. Rev. Immunol, 2003, 21, 305-34.
Scortti et al., "The PrfA virulence regulon", Microbes Infect. Aug. 2007;9(10):1196-207. Epub May 7, 2007.
Seffernick et al., "Melamine deaminase and atrazine chlorohydrolase. 98 percent identical but functionally different", J. Bacteriol. 183(8):2405-10, Apr. 2001.
Serth et al., "Increased Levels of Human Papillomavirus Type 16 DNA in a Subset of Prostate Cancers", Cancer Res. 1999 15:59(4):823-5.
Sewell et al., "Regression of HPV-positive tumors treated with a new *Listeria monocytogenes* vaccine", Arch Otolaryngol Head Neck Surg, Jan. 2004, vol. 130, 92-97.
Shen et al., "Recombinant *Listeria monocytogenes* as a Live Vaccine Vehicle for the Induction of Protective Anti-Viral Cell-Mediated Immunity", Proc. Natl. Acad. Sci., USA, 92:3987-3991, Apr. 25, 1995.
Shrikant et al., "CTLA-4 blockade reverses CD8+ T cell tolerance to tumor by a CD4+ T cell-and IL-2-dependent mechanism", Immunity, Oct. 1999, vol. 11, 483-493.
Silverman et al., "Expression of c-myc, c-raf-1, and c-Ki-ras in azaserine-induced pancreatic carcinomas and growing pancreas in rats" Mol. Carcinog 3(6):379-86, 1990.

(56) References Cited

OTHER PUBLICATIONS

Singh et al., "Structure-Based design of a potent, selective arid irreversible inhibitor of the catalytic domain of the erbb receptor subfamily of protein tyrosine kinases", J. Med. Chem., 1997, 40, 1130-1135.

Singh et al., "Vaccination strategy determines the emergence and dominance of CD8+ T-cell epitopes in a FVB/N Rat HER-2/neu mouse model of breast cancer", Cancer Res., 66, 15, Aug. 2006, 7748-7757.

Stover et al., "New Use of BCG for Recombinant Vaccines", Nature 1991, 351, 456-460.

Strych et al., "Mutant analysis shows that alanine racemases from *Pseudomonas aeruginosa* and *Escherichia coli* are dimeric". Journal of Bacteriology, Aug. 2002, p. 4321-4325.

Szalay et al., "Presentation of *Listeria monocytogenes* antigens by major histocompatibility complex class I molecules to CD8 cytooxc T lymphocyes independent of listeriolysin secretion and virulence", Eur. J. Immunol., Jul. 1994; 24(7)1471-7.

Teitelbaum et al., "Mycobacterial infection of macrophages results in membrane-permeable phagosomes", Proc. Natl. Acad. Sci. USA, Dec. 1999; 96(26)1 5190-5.

Thompson et al., "Pathogenicity and Immunogenicity of a *Listeria monocytogenes* strain that requires D-alaninc for growth", Infection and Immunity, Aug. 1998, vol. 66, No. 8, p. 3552-3561.

Thull et al., "Recognition and management of hereditary breast cancer syndromes", The Oncologist, 2004; 9:13-24.

Townsend et al., "Tumor Rejection after Direct Costimulation of CD8+ T Cells by B7-Transfected Melanoma Cells", Science 1993, 259, 368-370.

Travis, "A Stimulating New Approach to Cancer Treatment", Science 1993, 259, 310-311.

Ulmanen et al., "Transcription and Translation of Foreign genes in *Bacillus subtilis* by the aid o a secretion vector", Journal of Bacteriology, Apr. 1985, vol. 162, No. 1, p. 176-182.

Uyttenhove et al., "Escape of mouse mastocytoma P815 after Nearly complete rejection is due to antigen-loss variants rather than immunosuppression", J. Exp. Med., vol. 157, Mar. 1983, 1040-1052.

Vazquez et al., "Differerential regulation of Ia expression and antigen presentation by listeriolysin-producing versus non-producing strains of Listeria monocytogenes", J. Leukoc Biol., May 1996; 59(5):683-90.

Villanueva et al., "Listeriolysin is processed efficiently into an MHC class I-associated epitope in *Listeria monocytogenes*-infected cells", J. Immunol., Dec. 1, 1995; 155(11):5227-33.

Vines et al., "Identification and charcterization of nucleotide sequence difference in there virulence-associate genes of *Listeria monocytogenes* strains representing clinically important serotypes", Current Microbiology, May 1998, vol. 36, No. 5, pp. 309-318.

Vitiello et al., "Development of a Lipopeptide-based Therapeutic Vaccine to treat chronic HBV infection", J. Ciin. Invest., vol. 95, Jan. 1995, 341-349.

Watson et al., "Immunosurveillance is active in colorectal cancer as downregulation but not complete loss of MHC class I expression correlates with a poor prognosis", Int. J. Cancer, 2000, 118, 6-10.

Wei et al., "Protection against mammary tumor growth by vaccination with full-length, modified human ErbB-2 DNA", Int. J. Cancer, 81, 748-754, 1999.

Wilson et al., "Transient expression of bacterial gene fragments in eukaryotic cells: implications for CD8(+) T cell epitope analysis", J. lmmunol. Methods, Feb. 2000, 234(1-2):137-47.

Wingens et al., "Structural analysis of an epidermal growth factor / transforming growth factor-α chimera with uniqe ErbB binding specificity", The Journal of Biological Chemistry, vol, 278, No. 40, Issue of Oct. 3, pp. 39114-39123, 2003.

Witkowski et al., "Conversion of a beta-ketoacyl synthase to a malonyl decarboxylase by replacement of the active-site cysteine with glutamine", Biochemistry 38(36):11643-50, Sep. 7, 1999.

Wu et al., "Engineering an intracellular pathway for major histocompatibility complex class II presentation of antigens", Proc. Natl. Acad. Sci. USA, 1995, 92:11671-5.

Wunderlich et al., "Assays for T cell function: induction and measurement of sytotoxic T lymphocyte activity", Current Protocols in Immunology, 1997, vol. 3, p. 3.11-3.11.20.

Yaghmai et al., "Optimized regulation of gene expression using artificial transcription factors", Molecular Therapy, Jun. 2002, vol. 5, No. 6, 685-694.

Young et al., "Cloning and Expression of Influenza Virus Genes", The Origin of Pandemic Influenza Viruses, W.G. Laver, eds., Elsevier Science Publishing Co., Inc., NY, 1983, p. 129.

Zhang et al., "Selection of Tumor Antigens as Targets for Immune Attack Using Immunohistochemistry: Protein Antigens", Clin Cancer Res. 1998 4:2669-2676.

Zubair et al., "Live recombinant vaccine vectors for HPV antigens associated with infection and malignancy", In: Vaccines for Human Papillomavirus Infection and Anogential Disease (ed. Robert W. Tindle), 1999, pp. 173-192.

Zwickey et al., "Peptide epitopes from noncytosolic *Listeria monocytogenes* can be presented by major histocompatibiity complex class I molecules", Infect. Immun., May 1996; 64(5):1870-2.

Zwickey et al.,"Antigen secreted from noncytosolic listeria monocytogenes is processed by the classical MHC class I processing pathway", J. Immunol., Jun. 1999, 162(11):6341-50.

Meneguzzi et al., Virology, 1991, vol. 181, pp. 62-69.

Peng et al., Cancer Immunol. Immunother., 2007, vol. 56, pp. 797-806.

Jager et al., J. Exp. Med., 2000, vol. 191, pp. 625-630.

Hausen et al., J. of the National Cancer Institute, 2000, vol. 92, pp. 690-698.

Hussain et al., Cancer Immunology, Immunotherapy, 2005, vol. 54, no. 6, pp. 577-589.

Paterson et al., Faseb Journal, vol. 16, No. 2, Mar. 2002, p. A665.

Borysiewicz et al. "A recombinant vaccinia virus encoding Human Papillomavirus Types 16 and 18, E6 and E7 proteins as immunotherapy for Cervical Cancer" Lancet, 0099-5355, Jun. 1, 1996, vol. 347, Issue 9014.

Einstein et al. "Heat shock fusion protein-based immunotherapy for treatment of cervical intraepithelial neoplasia III" Gynecologic Oncology 106 (2007) 453-460.

Mandavi et al., "Vaccines against Human Papillomavirus and Cervical Cancer: Promises and Challenges" The Oncologist 2005; 10:528-538.

Paterson et al., "*Listeria*-based vaccines for cancer treatment", Current opinion in molecular therapeutics, Current drugs, vol. 7, No. 5, 2005, pp. 454-460.

Michel et al., Attenuated mutants of the intracellular bacterium *Listeria monocytogenes* obtained by single amino acid listeriolysin O, Molecular Microbiology (1990), 4(12), pp. 2167-2178.

Gene Bank Accession No. AA 435505 (1999, p. 1-4).

* cited by examiner

1: Liver
2: Spleen
3: Thyroid
4: Thymus

5. Cathepsin S
6. E7
7. Actin
8. Negative Control

DAYS POST TUMOR INOCULATION

COMPOSITIONS AND METHODS FOR TREATMENT OF NON-HODGKINS LYMPHOMA

FIELD OF INVENTION

The present invention provides recombinant peptides comprising a B cell receptor (BCR) or a fragment thereof, nucleotide molecules encoding same, and vaccines and vectors comprising same; and methods of treating, inducing an immune response against, inducing a regression of, and suppressing a formation of a lymphoma, comprising administering same. The present invention also provides methods of inducing a humoral immune response in an animal against an antigen, comprising administering to the animal a fusion peptide comprising an LLO protein or fragment thereof fused to the antigen.

BACKGROUND OF THE INVENTION

Non-Hodgkin's Lymphoma is a group of lymphoid malignancies classified into sub-groups based on histological appearance, biology and clinical presentation/course. In 2002 there were approximately 54,000 new cases of NHL in the US, representing 4% of all cancers (Ries et al., 2002). The annual incidence rate was 19.1 cases per 100,000 people. Most NHL cases arise in the lymph node (70-80%). Currently, there is an increased incidence of NHL in the US of 2.6% per year in males and 2.0% per year in females. Immunodeficiency (both acquired and congenital) is the strongest risk factor known to increase NHL (Rabkin et al., 1997).

Cytogenetic studies have shown that some histological and immunological sub-types of NHL have chromosomal abnormalities with reciprocal translocations, frequently involving genes for the B-cell receptor and an oncogene. Lymphomagenesis results in clonal expansion of the transformed B-cell, with each daughter cell expressing the B-cell receptor (BCR) on the cell surface as well as BCR-derived peptides associated with MHC class I and II molecules. The BCR has a unique conformation formed by the hypervariable regions of the heavy and light chain, this is referred to as the "idiotype," is the same for every daughter cell within the tumor, and is not present on significant numbers of normal cells. Therefore, the idiotype is a specific tumor antigen and a target for lymphoma therapy.

The follicular lymphomas are the most common subtype of indolent NHL, representing about 30% of NHL. Rituximab, a chimeric anti-CD20 antibody originally studied in patients with relapsed and refractory follicular low-grade NHL, exhibits a high overall response rates as an initial therapy, but a limited response duration. In addition, idiotype-based clinical trials for follicular NHL have been successful in the setting of minimal residual disease, increasing disease free survival as well as molecular remission. A current idiotype-based vaccine for B-NHL uses KLH as a protein carrier coupled to the patient's own B cell receptor (BCR) idiotype (Id) and GM-CSF as an adjuvant. Patients who respond to the Id-KLH vaccine with an anti-idiotype response (50-70%) exhibit higher rates of disease-free survival.

Improved therapies for NHL continue to be needed in the art.

SUMMARY OF THE INVENTION

The present invention provides recombinant peptides comprising a B cell receptor (BCR) or a fragment thereof, nucleotide molecules encoding same, and vaccines and vectors comprising same; and methods of treating, inducing an immune response against, inducing a regression of, and suppressing a formation of a lymphoma, comprising administering same. The present invention also provides methods of inducing a humoral immune response in an animal against an antigen, comprising administering to the animal a fusion peptide comprising an LLO protein or fragment thereof fused to the antigen.

In one embodiment, the present invention provides a recombinant peptide comprising a listeriolysin O (LLO) protein or a fragment thereof and either: (a) a BCR; or (b) a fragment of a BCR, wherein the fragment comprises the idiotype of the BCR.

In another embodiment, the present invention provides a method for inducing an immune response against a lymphoma, comprising administering a peptide of the present invention, thereby inducing an immune response against a lymphoma.

In another embodiment, the present invention provides a method for inducing an immune response against a lymphoma, comprising administering a nucleotide molecule of the present invention, thereby inducing an immune response against a lymphoma.

In another embodiment, the present invention provides a method for treating a lymphoma, comprising administering a peptide of the present invention, thereby treating a lymphoma.

In another embodiment, the present invention provides a method for treating a lymphoma, comprising administering a nucleotide molecule of the present invention, thereby treating a lymphoma.

In another embodiment, the present invention provides a method for inducing a regression of a lymphoma, comprising administering a peptide of the present invention, thereby inducing a regression of a lymphoma.

In another embodiment, the present invention provides a method for inducing a regression of a lymphoma, comprising administering a nucleotide molecule of the present invention, thereby inducing a regression of a lymphoma.

In another embodiment, the present invention provides a method for overcoming an immune tolerance to a lymphoma, comprising administering a peptide of the present invention, thereby overcoming an immune tolerance to a lymphoma.

In another embodiment, the present invention provides a method for overcoming an immune tolerance to a lymphoma, comprising administering a nucleotide molecule of the present invention, thereby overcoming an immune tolerance to a lymphoma.

In another embodiment, the present invention provides a method for reducing an incidence of relapse of a lymphoma in a subject in remission from the lymphoma, comprising administering to the subject a peptide of the present invention, thereby reducing an incidence of relapse of a lymphoma in a subject in remission from the lymphoma.

In another embodiment, the present invention provides a method for reducing an incidence of relapse of a lymphoma in a subject in remission from the lymphoma, comprising administering to the subject a nucleotide molecule of the present invention, thereby reducing an incidence of relapse of a lymphoma in a subject in remission from the lymphoma.

In another embodiment, the present invention provides a method for suppressing a formation of a lymphoma, thereby suppressing a formation of a lymphoma.

In another embodiment, the present invention provides a method for suppressing a formation of a lymphoma, comprising administering a nucleotide molecule of the present invention, thereby suppressing a formation of a lymphoma.

In another embodiment, the present invention provides a method of inducing a remission of a residual B cell lymphoma disease, comprising administering a peptide of the present invention, thereby inducing a remission of a residual B cell lymphoma disease.

In another embodiment, the present invention provides a method of inducing a remission of a residual B cell lymphoma disease, comprising administering a nucleotide molecule of the present invention, thereby inducing a remission of a residual B cell lymphoma disease.

In another embodiment, the present invention provides a method of inducing a humoral immune response in an animal against an antigen, comprising administering to the animal a peptide comprising an LLO protein or a fragment thereof and the antigen or a fragment thereof, thereby inducing a humoral immune response in an animal against an antigen.

DETAILED DESCRIPTION OF THE INVENTION

Figure 1:
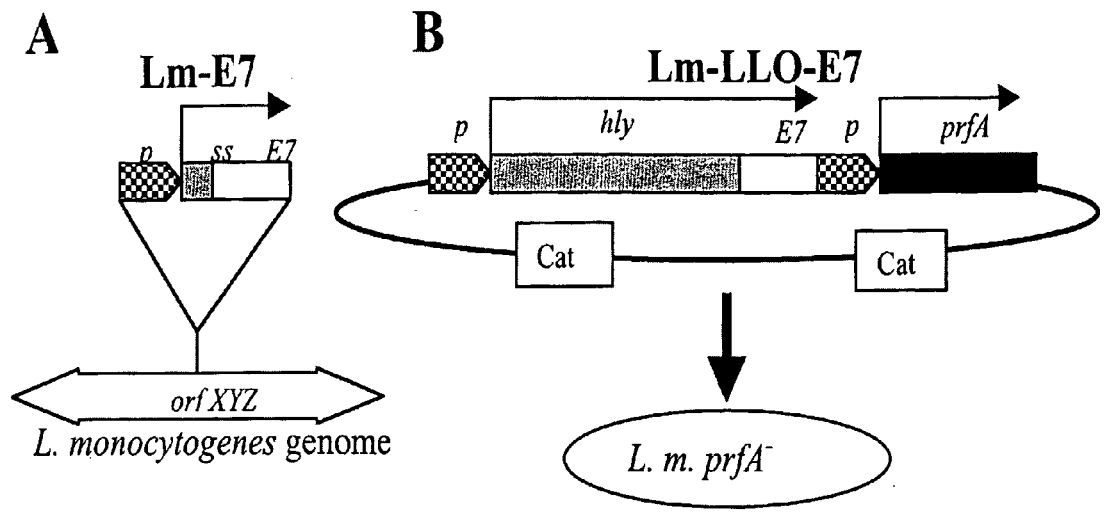
FIG. 1. Lm-E7 and Lm-LLO-E7 use different expression systems to express and secrete E7. Lm-E7 was generated by introducing a gene cassette into the orfZ domain of the *L. monocytogenes* genome (A). The hly promoter drives expression of the hly signal sequence and the first five amino acids (AA) of LLO followed by HPV-16 E7. B), Lm-LLO-E7 was generated by transforming the prfA-strain XFL-7 with the plasmid pGG-55. pGG-55 has the hly promoter driving expression of a nonhemolytic fusion of LLO-E7. pGG-55 also contains the prfA gene to select for retention of the plasmid by XFL-7 in vivo.

The present invention provides recombinant peptides comprising a B cell receptor (BCR) or a fragment thereof, nucleotide molecules encoding same, and vaccines and vectors comprising same; and methods of treating, inducing an immune response against, inducing a regression of, and suppressing a formation of a lymphoma, comprising administering same. The present invention also provides methods of inducing a humoral immune response in an animal against an antigen, comprising administering to the animal a fusion peptide comprising an LLO protein or fragment thereof fused to the antigen.

In one embodiment, the present invention provides a recombinant peptide comprising a listeriolysin O (LLO) protein or a fragment thereof and either: (a) a BCR; or (b) a fragment of a BCR, wherein the fragment comprises the idiotype of the BCR.

As provided herein, the present invention has produced a conformationally intact fusion protein comprising an LLO protein and a BCR idiotype (Example 21).

In another embodiment, the LLO protein or fragment thereof is on the N-terminal end of a fusion peptide of the present invention. In another embodiment, the LLO protein or fragment thereof is internal. In another embodiment, the LLO protein or fragment thereof is on the C-terminal end. Each possibility represents a separate embodiment of the present invention.

In another embodiment, a peptide of the present invention is a fusion peptide. In another embodiment, "fusion peptide" refers to a peptide or polypeptide comprising two or more proteins linked together by peptide bonds or other chemical bonds. In another embodiment, the proteins are linked together directly by a peptide or other chemical bond. In another embodiment, the proteins are linked together with one or more AA (e.g. a "spacer") between the two or more proteins. Each possibility represents a separate embodiment of the present invention.

The LLO protein utilized to construct vaccines of the present invention (in another embodiment, used as the source of the LLO fragment incorporated in the vaccines) has, in another embodiment, the sequence:
mkkimlvfitlilvslpiaqqteak-dasafnkensissmappasppaspkt-piekkhadeidkyiqgldynknnylvyhgdavtnvpprkgykdgneyivvekkkksinqn-nadiqvvnaissltypgalvkansel-venqpdvlpvkrdsltlsidlpgmtnqdnkivvknat ksnvnnavntlver-wnekyaqaypnvsakidyddemaysesqliakfgtafkavnnslnvnfgais-egkmqeevisfkqiyynvn vneptrpsrffgkavtkeqlqalgv-naenppayissvaygrqvylklstnsh-stkvkaafdaavsgksvsgdveltniiknssfkaviyg gsakdevqiidgn-lgdlrdilkkgatfnretpgvpiayttnflkdnelaviknnseyiettskaytdgki-nidhsggyvaqfniswdevn ydpegneivqhknwsennksklah-ftssiylpgnarninvyakectglawew-wrtviddrnlplvknrnisiwgttlypkysnkvdn pie (GenBank Accession No. P13128; SEQ ID NO: 42; nucleic acid sequence is set forth in GenBank Accession No. X15127). The first 25 AA of the proprotein corresponding to this sequence are the signal sequence and are cleaved from LLO when it is secreted by the bacterium. Thus, in this embodiment, the full length active LLO protein is 504 residues long.

In another embodiment, the N-terminal fragment of an LLO protein utilized in compositions and methods of the present invention has the sequence:

```
Mkkimlvfitlilvslpiaqqteakdasafnkensi    (SEQ ID NO:25)
ssvappasppaspktpiekkhadeidkyiqgldynk
nnvlvyhgdavtnvpprkgykdgneyivvekkkksi
nqnnadiqvvnaissltypgalvkanselvenqpdv
lpvkrdsltlsidlpgmtnqdnkivvknatksnvnn
avntlverwnekyaqaysnvsakidyddemaysesq
liakfgtafkavnnslnvnfgaisegkmqeevisfk
qiyynvnvneptrpsrffgkavtkeqlqalgvnaen
```
```
ppayissvaygrqvylklstnshstkvkaafdaavs
gksvsgdveltniiknssfkaviyggsakdevqiid
gnlgdlrdilkkgatfnretpgvpiayttnflkdne
laviknnseyiettskaytdgkinidhsggyvaqfn
iswdevnyd.
```

In another embodiment, the LLO fragment is "LLO-detox" (Examples). In another embodiment, the LLO fragment corresponds to AA 20-442 of an LLO protein utilized herein.

In another embodiment, the LLO fragment has the sequence:

```
Mkkimlvfitlilvslpiaqqteakdasafnkensi    (SEQ ID NO:41)
ssvappasppaspktpiekkhadeidkyiqgldynk
nnvlvyhgdavtnvpprkgykdgneyivvekkkksi
nqnnadiqvvnaissltypgalvkanselvenqpdv
lpvkrdsltlsidlpgmtnqdnkivvknatksnvnn
avntlverwnekyaqaysnvsakidyddemaysesq
liakfgtafkavnnslnvnfgaisegkmqeevisfk
qiyynvnvneptrpsrffgkavtkeqlqalgvnaen
ppayissvaygrqvylklstnshstkvkaafdaavs
gksvsgdveltniiknssfkaviyggsakdevqiid
gnlgdlrdikkgatfnretpgvpiayttnflkdnel
aviknnseyiettskaytd.
```

In another embodiment, "truncated LLO" or "ΔLLO" refers to a fragment of LLO that comprises the PEST-like domain. In another embodiment, the terms refer to an LLO fragment that comprises a PEST sequence. In another embodiment, the LLO fragment consists of a PEST sequence.

In another embodiment, the terms refer to an LLO fragment that does not contain the activation domain at the amino terminus and does not include cysteine 484. In another embodiment, the terms refer to an LLO fragment that is not hemolytic. In another embodiment, the LLO fragment is rendered non-hemolytic by deletion or mutation of the activation domain. In another embodiment, the LLO fragment is rendered non-hemolytic by deletion or mutation of cysteine 484. In another embodiment, the LLO fragment is rendered non-hemolytic by deletion or mutation at another location. Each possibility represents a separate embodiment of the present invention.

In another embodiment, the LLO fragment consists of about the first 441 AA of the LLO protein. In another embodiment, the LLO fragment consists of about the first 420 AA of LLO. In another embodiment, the LLO fragment is a non-hemolytic form of the LLO protein.

In another embodiment, the LLO fragment contains residues of a homologous LLO protein that correspond to one of the above AA ranges. The residue numbers need not, in another embodiment, correspond exactly with the residue numbers enumerated above; e.g. if the homologous LLO protein has an insertion or deletion, relative to an LLO protein utilized herein.

In another embodiment, the LLO fragment is any other LLO fragment known in the art. Each possibility represents a separate embodiment of the present invention.

In another embodiment, the fragment of an LLO protein contained in peptides of the present invention is an N-terminal fragment. In another embodiment, the fragment is an internal fragment. Each possibility represents a separate embodiment of the present invention.

In another embodiment, a whole LLO protein is utilized in methods and compositions of the present invention. In another embodiment, the whole LLO protein is a non-hemolytic LLO protein.

In another embodiment, an LLO protein of the present invention is rendered non-hemolytic by chemical treatment. In another embodiment, the LLO protein is rendered nonhemolytic by glutaraldehyde treatment, as exemplified herein. In another embodiment, the LLO protein is rendered non-hemolytic by any other method known in the art. Each possibility represents a separate embodiment of the present invention.

In another embodiment, a complete B cell receptor (BCR) is contained or utilized in methods and compositions of the present invention. In another embodiment, a fragment of a BCR is contained or utilized. In another embodiment, the BCR fragment contains the idiotype thereof. In another embodiment, the BCR fragment contains a T cell epitope. In another embodiment, the BCR fragment contains an antibody epitope. In another embodiment, "antigen" is used herein to refer to the BCR or fragment thereof that is the target of immune responses induced by methods and compositions of the present invention.

In another embodiment, the fragment of a BCR contained in peptides of the present invention is a single chain fragment of the variable regions (scFV) of the BCR. In another embodiment, the BCR fragment is conformationally intact. In another embodiment, the BCR fragment contains the idiotype of the BCR. In another embodiment, the BCR idiotype is conformationally intact. Each possibility represents a separate embodiment of the present invention.

"Idiotype" refers, in another embodiment, to the complementarity-determining region (cdr) of a BCR. In another embodiment, the term refers to the unique region of a BCR. In another embodiment, the term refers to the antigen-binding site of the BCR. Each possibility represents a separate embodiment of the present invention.

"Conformationally intact" refers, in another embodiment, to a conformation that is not significantly altered relative to the native conformation. In another embodiment, the term refers to an antibody reactivity that is not significantly altered relative to the native protein. In another embodiment, the term refers to an antibody reactivity that overlaps substantially with the native protein. Each possibility represents a separate embodiment of the present invention.

In another embodiment, a recombinant peptide of the present invention further comprises a detectable tag polypeptide. In another embodiment, a detectable tag polypeptide is not included. In other embodiments, the tag polypeptide is green fluorescent protein (GFP), myc, myc-pyruvate kinase (myc-PK), $His_6$, maltose biding protein (MBP), an influenza virus hemagglutinin tag polypeptide, a flag tag polypeptide (FLAG), and a glutathione-S-transferase (GST) tag polypeptide. However, the invention should in no way be construed to be limited to the nucleic acids encoding the above-listed tag polypeptides. In another embodiment, the present invention utilizes any nucleic acid sequence encoding a polypeptide which functions in a manner substantially similar to these tag polypeptides. Each possibility represents a separate embodiment of the present invention.

In another embodiment, the present invention provides a nucleotide molecule encoding a fusion peptide of the present invention. In another embodiment, the present invention provides a vaccine comprising a nucleotide molecule of the present invention. In another embodiment, the vaccine further comprises an adjuvant. Each possibility represents a separate embodiment of the present invention.

In another embodiment, the present invention provides a vaccine comprising a peptide of the present invention. In another embodiment, the vaccine further comprises an adjuvant. Each possibility represents a separate embodiment of the present invention.

In another embodiment, the present invention provides an immunogenic composition comprising a peptide of the present invention. In another embodiment, the immunogenic composition further comprises an adjuvant. Each possibility represents a separate embodiment of the present invention.

The adjuvant utilized in methods and compositions of the present invention is, in another embodiment, a granulocyte/macrophage colony-stimulating factor (GM-CSF) protein. In another embodiment, the adjuvant comprises a GM-CSF protein. In another embodiment, the adjuvant is a nucleotide molecule encoding GM-CSF. In another embodiment, the adjuvant comprises a nucleotide molecule encoding GM-CSF. In another embodiment, the adjuvant is saponin QS21. In another embodiment, the adjuvant comprises saponin QS21. In another embodiment, the adjuvant is monophosphoryl lipid A. In another embodiment, the adjuvant comprises monophosphoryl lipid A. In another embodiment, the adjuvant is SBAS2. In another embodiment, the adjuvant comprises SBAS2. In another embodiment, the adjuvant is an unmethylated CpG-containing oligonucleotide. In another embodiment, the adjuvant comprises an unmethylated CpG-containing oligonucleotide. In another embodiment, the adjuvant is an immune-stimulating cytokine. In another embodiment, the adjuvant comprises an immune-stimulating cytokine. In another embodiment, the adjuvant is a nucleotide molecule encoding an immune-stimulating cytokine. In another embodiment, the adjuvant comprises a nucleotide molecule encoding an immune-stimulating cytokine. In another embodiment, the adjuvant is or comprises a quill glycoside. In another embodiment, the adjuvant is or comprises a bacterial mitogen. In another embodiment, the adjuvant is or comprises a bacterial toxin. In another embodiment, the adjuvant is or comprises any other adjuvant known in the art. Each possibility represents a separate embodiment of the present invention.

In another embodiment, the present invention provides a recombinant vaccine vector encoding a peptide of the present invention. In another embodiment, the present invention provides a recombinant vaccine vector comprising a peptide of the present invention. Each possibility represents a separate embodiment of the present invention.

In another embodiment, the present invention provides a recombinant vaccine vector comprising a nucleotide molecule of the present invention. In another embodiment, the expression vector is a plasmid. In another embodiment, the present invention provides a method for the introduction of a nucleotide molecule of the present invention into a cell. Methods for constructing and utilizing recombinant vectors are well known in the art and are described, for example, in Sambrook et al. (2001, Molecular Cloning: A Laboratory Manual, Cold Spring Harbor Laboratory, New York), and in Brent et al. (2003, Current Protocols in Molecular Biology, John Wiley & Sons, New York). In another embodiment, the vector is a bacterial vector. In other embodiments, the vector is selected from *Salmonella* sp., *Shigella* sp., BCG, *L. monocytogenes* and *S. gordonii*. In another embodiment, the fusion proteins are delivered by recombinant bacterial vectors modified to escape phagolysosomal fusion and live in the cytoplasm of the cell. In another embodiment, the vector is a viral vector. In other embodiments, the vector is selected from Vaccinia, Avipox, Adenovirus, AAV, Vaccinia virus NYVAC, Modified vaccinia strain Ankara (MVA), Semliki Forest virus, Venezuelan equine encephalitis virus, herpes viruses, and retroviruses. In another embodiment, the vector is a naked DNA vector. In another embodiment, the vector is any other vector known in the art. Each possibility represents a separate embodiment of the present invention.

In another embodiment, a nucleotide of the present invention is operably linked to a promoter/regulatory sequence that drives expression of the encoded peptide in cells into which the vector is introduced. Promoter/regulatory sequences useful for driving constitutive expression of a gene are well known in the art and include, but are not limited to, for example, the cytomegalovirus immediate early promoter enhancer sequence, the SV40 early promoter, and the Rous sarcoma virus promoter. In another embodiment, inducible and tissue specific expression of the nucleic acid encoding a peptide of the present invention is accomplished by placing the nucleic acid encoding the peptide under the control of an inducible or tissue specific promoter/regulatory sequence. Examples of tissue specific or inducible promoter/regulatory sequences which are useful for his purpose include, but are not limited to the MMTV LTR inducible promoter, and the SV40 late enhancer/promoter. In another embodiment, a promoter that is induced in response to inducing agents such as metals, glucocorticoids, and the like, is utilized. Thus, it will be appreciated that the invention includes the use of any promoter/regulatory sequence, which is either known or unknown, and which is capable of driving expression of the desired protein operably linked thereto.

In another embodiment, the present invention provides a recombinant *Listeria* strain comprising a recombinant polypeptide of the present invention. In another embodiment, the present invention provides a recombinant *Listeria* strain comprising a recombinant nucleotide encoding a recombinant polypeptide of the present invention. In another embodiment, the *Listeria* vaccine strain is the species *Listeria monocytogenes* (LM). Each possibility represents a separate embodiment of the present invention.

In another embodiment, the present invention provides a cell comprising a vector of the present invention. Methods for producing cells comprising vectors and/or exogenous nucleic acids are well-known in the art. See, for example, Sambrook et al. (1989, Molecular Cloning: A Laboratory Manual, Cold Spring Harbor Laboratory, New York), and in Ausubel et al. (1997, Current Protocols in Molecular Biology, John Wiley & Sons, New York).

In another embodiment, the present invention provides a method for inducing an immune response against a lymphoma, comprising administering a peptide of the present invention, thereby inducing an immune response against a lymphoma.

In another embodiment, the present invention provides a method for inducing an immune response against a lymphoma, comprising administering a nucleotide molecule of the present invention, thereby inducing an immune response against a lymphoma.

In another embodiment, the present invention provides a method for treating a lymphoma, comprising administering a peptide of the present invention, thereby treating a lymphoma.

In another embodiment, the present invention provides a method for treating a lymphoma, comprising administering a nucleotide molecule of the present invention, thereby treating a lymphoma.

As provided herein, fusion of LLO (Examples 1 and 3) or ActA (Example 5) to an antigen increases its immunogenicity. In addition, administration of LLO-fusion proteins to an animal halts tumor growth, (Examples 2 and 11) results in clearing of existing tumors (Examples 11) and the induction of antigen specific CD8+ cells capable of infiltrating infected or tumor cells (Examples 6 and 12). Enhancement of immunogenicity does not require a *Listeria* vector (Examples 4 and 13), but rather is an inherent property of the fusion peptides. Moreover, compositions of the present invention are capable of overcoming tolerance to a self antigen (Examples 10, 14, and 15) and reducing the incidence of autochthonous tumors (Example 16). In addition, administration of fusion proteins of the present invention results in protection against tumor challenge.

Moreover, as provided herein, the present invention has produced a conformationally intact fusion protein comprising an LLO protein and a BCR idiotype, has demonstrated accurate and effective methodologies for testing anti-lymphoma vaccines in mouse and animal models, and has shown the efficacy of vaccines of the present invention in protecting against lymphoma and their superiority over currently accepted anti-lymphoma vaccines (Examples 17-24).

Thus, vaccines of the present invention are efficacious in inducing an immune response to, preventing, treating, and inducing remission of lymphoma.

In another embodiment, a peptide of the present invention activates an APC (e.g. a DC), mediating at least part of its increased immunogenicity (Example 13). In another embodiment, ΔLLO need not be attached to the idiotype-containing protein to enhance its immunogenicity. Each possibility represents a separate embodiment of the present invention.

In another embodiment, the present invention provides a method for inducing a regression of a lymphoma, comprising administering a peptide of the present invention, thereby inducing a regression of a lymphoma.

In another embodiment, the present invention provides a method for inducing a regression of a lymphoma, comprising administering a nucleotide molecule of the present invention, thereby inducing a regression of a lymphoma.

In another embodiment, the present invention provides a method for overcoming an immune tolerance to a lymphoma, comprising administering a peptide of the present invention, thereby overcoming an immune tolerance to a lymphoma.

In another embodiment, the present invention provides a method for overcoming an immune tolerance to a lymphoma, comprising administering a nucleotide molecule of the present invention, thereby overcoming an immune tolerance to a lymphoma.

"Tolerance" refers, in another embodiment, to a lack of responsiveness of the host to an antigen. In another embodiment, the term refers to a lack of detectable responsiveness of the host to an antigen. In another embodiment, the term refers to a lack of immunogenicity of an antigen in a host. In another embodiment, tolerance is measured by lack of responsiveness in an in vitro CTL killing assay. In another embodiment, tolerance is measured by lack of responsiveness in a delayed-type hypersensitivity assay. In another embodiment, tolerance is measured by lack of responsiveness in any other suitable assay known in the art. In another embodiment, tolerance is determined or measured as depicted in the Examples herein. Each possibility represents another embodiment of the present invention.

"Overcome" refers, in another embodiment, to a reversal of tolerance by a vaccine. In another embodiment, the term refers to conferment of detectable immune response by a vaccine. In another embodiment, overcoming of immune tolerance is determined or measured as depicted in the Examples herein. Each possibility represents another embodiment of the present invention.

In another embodiment, the present invention provides a method for reducing an incidence of relapse of a lymphoma in a subject in remission from the lymphoma, comprising administering to the subject a peptide of the present invention, thereby reducing an incidence of relapse of a lymphoma in a subject in remission from the lymphoma.

In another embodiment, the present invention provides a method for reducing an incidence of relapse of a lymphoma in a subject in remission from the lymphoma, comprising administering to the subject a nucleotide molecule of the present invention, thereby reducing an incidence of relapse of a lymphoma in a subject in remission from the lymphoma.

In another embodiment, the present invention provides a method for suppressing a formation of a lymphoma, thereby suppressing a formation of a lymphoma.

In another embodiment, the present invention provides a method for suppressing a formation of a lymphoma, comprising administering a nucleotide molecule of the present invention, thereby suppressing a formation of a lymphoma.

In another embodiment, the present invention provides a method of inducing a remission of a residual B cell lymphoma disease, comprising administering a peptide of the present invention, thereby inducing a remission of a residual B cell lymphoma disease.

In another embodiment, the present invention provides a method of inducing a remission of a residual B cell lymphoma disease, comprising administering a nucleotide molecule of the present invention, thereby inducing a remission of a residual B cell lymphoma disease.

In another embodiment, the present invention provides a method of eliminating minimal residual B cell lymphoma disease, comprising administering a peptide of the present invention, thereby eliminating minimal residual B cell lymphoma disease.

In another embodiment, the present invention provides a method of eliminating minimal residual B cell lymphoma disease, comprising administering a nucleotide molecule of the present invention, thereby eliminating minimal residual B cell lymphoma disease.

In another embodiment, the present invention provides a method of reducing a size of a B cell lymphoma, comprising administering a peptide of the present invention, thereby reducing a size of a B cell lymphoma.

In another embodiment, the present invention provides a method of reducing a size of a B cell lymphoma, comprising administering a nucleotide molecule of the present invention, thereby reducing a size of a B cell lymphoma.

In another embodiment, the present invention provides a method of reducing a volume of a B cell lymphoma, comprising administering a peptide of the present invention, thereby reducing a volume of a B cell lymphoma.

In another embodiment, the present invention provides a method of reducing a volume of a B cell lymphoma, comprising administering a nucleotide molecule of the present invention, thereby reducing a volume of a B cell lymphoma.

In another embodiment, the residual B cell lymphoma disease or minimal residual B cell lymphoma disease treated by a method of the present invention is that remaining after de-bulking therapy. Methods for performing de-bulking therapy are well known in the art, and are described, for example, in Winter J N et al (Low-grade lymphoma. Hematology (Am Soc Hematol Educ Program). 2004:203-20) and Buske C et al (Current status and perspective of antibody therapy in follicular lymphoma. Haematologica. 2006 January; 91(1):104-12). Each possibility represents a separate embodiment of the present invention.

In another embodiment, the present invention provides a method of killing a cell of a tumor, comprising administering a vaccine, immunogenic composition, or vector comprising or encoding a recombinant polypeptide of the present invention, thereby killing a cell of a tumor. In another embodiment, the cell expresses an antigen present in the recombinant polypeptide. Each possibility represents a separate embodiment of the present invention.

In another embodiment, the present invention provides a method of suppressing a formation of a tumor, comprising administering an effective amount of a vaccine comprising either: (a) a recombinant polypeptide comprising an LLO or ActA protein or fragment thereof fused to the antigen or a fragment thereof; or (b) a recombinant nucleotide encoding the recombinant polypeptide, whereby the subject mounts an immune response against the antigen-expressing tumor, thereby suppressing a formation of a HPV-transformed or Her-2-transformed tumor.

In another embodiment of methods of the present invention, a vaccine of the present invention is administered. In another embodiment, an immunogenic composition of the present invention is administered. Each possibility represents a separate embodiment of the present invention. In another embodiment of methods and compositions of the present invention, a peptide, vaccine, or immunogenic composition of the present invention elicits an immune response against the cell.

In another embodiment of methods and compositions of the present invention, a peptide or nucleotide molecule of the present invention is administered to a subject having a lymphoma. In another embodiment, the peptide or nucleotide molecule is administered ex vivo to cells of a subject having a lymphoma. In another embodiment, the peptide is administered to a lymphocyte donor; lymphocytes from the donor are then administered, in another embodiment, to a subject having a lymphoma. In another embodiment, the peptide is administered to an antibody donor; antiserum from the donor is then administered, in another embodiment, to a subject having a lymphoma. Each possibility represents a separate embodiment of the present invention.

In another embodiment, the lymphoma that is a target of a method of present invention is, in another embodiment, a Non-Hodgkins Lymphoma. In another embodiment, a lymphoma is a B cell lymphoma. In another embodiment, a lymphoma is a low-grade lymphoma. In another embodiment, a lymphoma is a low-grade NHL. In another embodiment, a lymphoma is residual disease from one of the above types of lymphoma. In another embodiment, the lymphoma is any other type of lymphoma known in the art. In another embodiment, the lymphoma is any other known type of lymphoma that expresses of BCR.

In another embodiment, cells of the tumor that is targeted by methods and compositions of the present invention express a BCR. In another embodiment, the tumor is associated with a BCR. In another embodiment, the BCR has an idiotype that is characteristic of the tumor. In another embodiment, the BCR expressed by a tumor cell is the target of the immune responses induced by methods and compositions of the present invention.

In another embodiment, the BCR expressed by the target cell is required for a tumor phenotype. In another embodiment, the BCR is necessary for transformation of a tumor cell. In another embodiment, tumor cells that lose expression of the BCR lose their uncontrolled growth, invasiveness, or another feature of malignancy. Each possibility represents a separate embodiment of the present invention.

In another embodiment, a peptide utilized in methods of the present invention comprises an idiotype that is homologous to an idiotype expressed by cells of the lymphoma. In another embodiment, the peptide comprises an idiotype that is identical to an idiotype expressed by cells of the lymphoma. Each possibility represents a separate embodiment of the present invention.

In another embodiment, a nucleotide molecule utilized in methods of the present invention encodes an idiotype that is homologous to an idiotype expressed by cells of the lymphoma. In another embodiment, the nucleotide molecule encodes an idiotype that is identical to an idiotype expressed by cells of the lymphoma. In another embodiment, the antigen is highly homologous to the antigen expressed by the tumor cell. "Highly homologous" refers, in another embodiment, to a homology of greater than 90%. In another embodiment, the term refers to a homology of greater than 92%. In another embodiment, the term refers to a homology of greater than 93%. In another embodiment, the term refers to a homology of greater than 94%. In another embodiment, the term refers to a homology of greater than 95%. In another embodiment, the term refers to a homology of greater than 96%. In another embodiment, the term refers to a homology of greater than 97%. In another embodiment, the term refers to a homology of greater than 98%. In another embodiment, the term refers to a homology of greater than 99%. In another embodiment, the term refers to a homology of 100%. Each possibility represents a separate embodiment of the present invention.

Each type of lymphoma represents a separate embodiment of the present invention.

In another embodiment, the present invention provides a method for enhancing the immunogenicity of a BCR or fragment thereof, comprising fusing an LLO protein or fragment thereof to the BCR or fragment thereof. As demonstrated by the data disclosed herein, fusing an LLO protein, ActA protein, or fragment thereof to an antigen enhances the immunogenicity of a BCR or fragment thereof.

In another embodiment, the present invention provides a method for enhancing the immunogenicity of a BCR idiotype, comprising fusing an LLO protein or fragment thereof to the idiotype. In another embodiment, the idiotype is associated with a B cell lymphoma. Each possibility represents a separate embodiment of the present invention.

In another embodiment of methods and compositions of the present invention, an N-terminal fragment of an ActA protein is fused to the BCR or fragment thereof. In another embodiment, the N-terminal fragment of an ActA protein has the sequence set forth in SEQ ID NO: 23: MRAMMVVFITANCITINPDIIFAATD-SEDSSLNTDEWEEEKTEEQPSEVNTGPRYETARE VSSRDIKELEKSNKVRNTNKADLIAM-LKEKAEKGPNINNNNSEQTENAAINEEASGADR PAIQVERRHPGLPSDSAAEIKKRRKA-IASSDSELESLTYPDKPTKVNKKKVAKESVADAS ESDLDSSMQSADESSPQPLKANQQPFFP-KVFKKIKDAGKWVRDKIDENPEVKKAIVDKS AGLIDQLLTKKKSEEVNASDFPPPPT-DEELRLALPETPMLLGFNAPATSEPSSFEFPPPPTD EELRLALPETPMLLGFNAPATSEPSS-FEFPPPPTEDELEIIRETASSLDSSFTRGDLASLRNA INRHSQNFSDFPPIPTEEELNGRGGRP. In another embodiment, the ActA fragment comprises the sequence set forth in SEQ ID NO: 23. In another embodiment, the ActA fragment is any other ActA fragment known in the art. Each possibility represents a separate embodiment of the present invention.

In another embodiment, the recombinant nucleotide encoding a fragment of an ActA protein comprises the sequence set forth in SEQ ID NO: 24: Atgcgtgcgatgatggtg-gttttcattactgccaattgcattac-gattaaccccgacataatatttgcagcgacagatagcgaagattctagtct aaaca-cagatgaatgggaagaagaaaaaacagaagagcaaccaagcgaggtaaatacg-gaccaagatacgaaactgcacgtgaagt aagttcacgtgatattaaagaacta-gaaaaatcgaataaagtgagaaatac-gaacaaagcagacctaatagcaatgttgaaagaaaaagca gaaaaggtc-caaatatcaataataacaacagtgaacaaactgagaatgcggctataaatgaaga-ggcttcaggagccgaccgaccagct atacaagtggagcgtcgtcatccaggat-tgccatcggatagcgcagcggaaat-taaaaaaagaaggaaagccatagcatcatcggatagt gagcttgaaagccttact-tatccggataaaccaacaaaagtaaataagaaaaaagtggcgaaagagtcagttg-cggatgcttctgaaagtga cttagattctagcatgcagtcagcagat-gagtcttcaccacaacctttaaaag-caaaccaacaaccattttcctaaagtatttaaaaaaataa aagatgcggg-gaaatgggtacgtgataaaatcgacgaaaatcctgaagtaaagaaagcgattgttg-ataaaagtgcagggttaattgacca attattaaccaaaaagaaaagtgaagag-gtaaatgcttcggacttcccgccaccac-ctacggatgaagagttaagacttgctttgccagaga caccaatgcttcttggttt-taatgctcctgctacatcagaaccgagctcattcgaatttccaccaccacctacgga-tgaagagttaagacttgctt tgccagagacgccaatgcttcttggttt-taatgctcctgctacatcggaac-cgagctcgttcgaatttccaccgcctccaacagaagatgaact agaaatcatc-cgggaaacagcatcctcgctagattctagttttacaagaggggatttagctagtttg-agaaatgctattaatcgccatagtcaaa atttctctgatttcccaccaatcccaa-cagaagaagagttgaacgggagaggcggtagacca. In another embodiment, the recombinant nucleotide has the sequence set forth in SEQ ID NO: 24. In another embodiment, the recombinant nucleotide comprises any other sequence that encodes a fragment of an ActA protein. Each possibility represents a separate embodiment of the present invention.

In another embodiment of methods and compositions of the present invention, a PEST-like AA sequence is fused to the BCR or fragment thereof. As provided herein, enhanced cell mediated immunity was demonstrated for fusion proteins comprising an antigen and LLO containing the PEST-like AA sequence KENSISSMAPPASPPASPKTPIEKKHADEIDK (SEQ ID NO: 1). The ΔLLO used in some of the Examples was 416 AA long, as 88 residues from the amino terminus which is inclusive of the activation domain containing cysteine 484 were truncated. In other experiments (e.g. Example 11) a truncated LLO containing 441 AA of LLO was utilized. Thus, any ΔLLO without the activation domain, and in particular without cysteine 484, are suitable for methods and compositions of the present invention. More particularly, it is believed that fusion of an antigen to any ΔLLO including the PEST-like AA sequence, SEQ ID NO: 1, can enhance cell mediated and anti-tumor immunity of the antigen.

The PEST-like AA sequence has, in another embodiment, a sequence selected from SEQ ID NO: 2-7. In another embodiment, the PEST-like sequence is a PEST-like sequence from the LM ActA protein. In another embodiment, the PEST-like sequence is KTEEQPSEVNTGPR (SEQ ID NO: 2), KASVTDTSEGDLDSSMQSADESTPQPLK (SEQ ID NO: 3), KNEEVNASDFPPPPTDEELR (SEQ ID NO: 4), or RGGIPTSEEFSSLNSGDFTDDENSETTEEEIDR (SEQ ID NO: 5). In another embodiment, the PEST-like sequence is from Streptolysin O protein of *Streptococcus* sp. In another embodiment, the PEST-like sequence is from *Streptococcus pyogenes* Streptolysin O, e.g. KQNTASTETTTTNEQPK (SEQ ID NO: 6) at AA 35-51. In another embodiment, the PEST-like sequence is from *Streptococcus equisimilis* Streptolysin O, e.g. KQNTANTETTTTNEQPK (SEQ ID NO: 7) at AA 38-54. In another embodiment, the PEST-like sequence is another PEST-like AA sequence derived from a prokaryotic organism. In another embodiment, the PEST-like sequence is any other PEST-like sequence known in the art. Each possibility represents a separate embodiment of the present invention.

As demonstrated herein, fusion of an antigen to the PEST-like sequence of LM enhanced cell mediated and anti-tumor immunity of the antigen. Thus, fusion of an antigen to other PEST-like sequences derived from other prokaryotic organisms will also enhance immunogenicity of the antigen. PEST-like sequence of other prokaryotic organism can be identified in accordance with methods such as described by, for example Rechsteiner and Rogers (1996, Trends Biochem. Sci. 21:267-271) for LM. Alternatively, PEST-like AA sequences from other prokaryotic organisms can also be identified based by this method. Other prokaryotic organisms wherein PEST-like AA sequences would be expected to include, but are not limited to, other *Listeria* species. In another embodiment, the PEST-like sequence is embedded within the antigenic protein. Thus, in another embodiment, "fusion" refers to an antigenic protein comprising both the antigen and the PEST-like amino acid sequence either linked at one end of the antigen or embedded within the antigen.

As provided herein, fusion of an antigen to a non-hemolytic form of listeriolysin O (LLO) enhanced immunogenicity. In addition, an LM vector that expresses and secretes a fusion product of Human Papilloma Virus (HPV) strain 16 E7 and LLO, which comprises the PEST-like AA sequence SEQ ID NO: 1, is a more potent cancer immunotherapeutic for HPV immortalized tumors than a strain of LM that secretes the E7 protein alone. Experiments were also performed demonstrating that a recombinant vaccinia virus that carries the gene for the fusion protein LLO-E7, which comprises SEQ ID NO: 1, is a much more potent cancer immunotherapeutic for HPV immortalized tumors than an isogenic strain of vaccinia that carries the gene for E7 protein alone. In comparison, a short fusion protein Lm-AZ/-E7 comprising the E7 antigen fused to the promoter, signal sequence and the first 7 AA residues of LLO was an ineffective anti-tumor immunotherapeutic. This short fusion protein terminates directly before the PEST-like sequence and does not contain it. Thus, fusion to PEST-like sequences enhances immunogenicity.

In another embodiment, the LLO protein, ActA protein, or fragment thereof of the present invention need not be that which is set forth exactly in the sequences set forth herein, but rather that other alterations, modifications, or changes can be made that retain the functional characteristics of an LLO or ActA protein fused to an antigen as set forth elsewhere herein. In another embodiment, the present invention utilizes an analog of an LLO protein, ActA protein, or fragment thereof. Analogs differ, in another embodiment, from naturally occurring proteins or peptides by conservative AA sequence differences or by modifications which do not affect sequence, or by both.

In another embodiment, "homology" refers to identity to an LLO sequence (e.g. to SEQ ID No: 25, 41, or 42) of greater than 70%. In another embodiment, "homology" refers to identity to SEQ ID No: 25, 41, or 42 of greater than 72%. In another embodiment, "homology" refers to identity to SEQ ID No: 25, 41, or 42 of greater than 75%. In another embodiment, "homology" refers to identity to SEQ ID No: 25, 41, or 42 of greater than 78%. In another embodiment, "homology" refers to identity to SEQ ID No: 25, 41, or 42 of greater than 80%. In another embodiment, "homology" refers to identity to SEQ ID No: 25, 41, or 42 of greater than 82%. In another embodiment, "homology" refers to identity to SEQ ID No: 25, 41, or 42 of greater than 83%. In another embodiment, "homology" refers to identity to SEQ ID No: 25, 41, or 42 of greater than 85%. In another embodiment, "homology" refers to identity to SEQ ID No: 25, 41, or 42 of greater than 87%. In another embodiment, "homology" refers to identity to SEQ ID No: 25, 41, or 42 of greater than 88%. In another embodiment, "homology" refers to identity to SEQ ID No: 25, 41, or 42 of greater than 90%. In another embodiment, "homology" refers to identity to SEQ ID No: 25, 41, or 42 of greater than 92%. In another embodiment, "homology" refers to identity to SEQ ID No: 25, 41, or 42 of greater than 93%. In another embodiment, "homology" refers to identity to SEQ ID No: 25, 41, or 42 of greater than 95%. In another embodiment, "homology" refers to identity to SEQ ID No: 25, 41, or 42 of greater than 96%. In another embodiment, "homology" refers to identity to SEQ ID No: 25, 41, or 42 of greater than 97%. In another embodiment, "homology" refers to identity to SEQ ID No: 25, 41, or 42 of greater than 98%. In another embodiment, "homology" refers to identity to SEQ ID No: 25, 41, or 42 of greater than 99%. In another embodiment, "homology" refers to identity to SEQ ID No: 25, 41, or 42 of 100%. Each possibility represents a separate embodiment of the present invention.

In another embodiment of the present invention, "nucleic acids" or "nucleotide" refers to a string of at least two base-sugar-phosphate combinations. The term includes, in one embodiment, DNA and RNA. "Nucleotides" refers, in one embodiment, to the monomeric units of nucleic acid polymers. RNA is, in one embodiment, in the form of a tRNA (transfer RNA), snRNA (small nuclear RNA), rRNA (ribosomal RNA), mRNA (messenger RNA), anti-sense RNA, small inhibitory RNA (siRNA), micro RNA (mRNA) and ribozymes. The use of siRNA and mRNA has been described (Caudy A A et al, Genes & Devel 16: 2491-96 and references cited therein). In other embodiments, DNA can be in form of plasmid DNA, viral DNA, linear DNA, or chromosomal DNA or derivatives of these groups. In addition, these forms of DNA and RNA can be single, double, triple, or quadruple stranded. The term also includes, in another embodiment, artificial nucleic acids that contain other types of backbones but the same bases. In one embodiment, the artificial nucleic acid is a PNA (peptide nucleic acid). PNA contain peptide backbones and nucleotide bases and are able to bind, in one embodiment, to both DNA and RNA molecules. In another embodiment, the nucleotide is oxetane modified. In another embodiment, the nucleotide is modified by replacement of one or more phosphodiester bonds with a phosphorothioate bond. In another embodiment, the artificial nucleic acid contains any other variant of the phosphate backbone of native nucleic acids known in the art. The use of phosphothiorate nucleic acids and PNA are known to those skilled in the art, and are described in, for example, Neilsen P E, Curr Opin Struct Biol 9:353-57; and Raz N K et al Biochem Biophys Res Commun. 297:1075-84. The production and use of nucleic acids is known to those skilled in art and is described, for example, in Molecular Cloning, (2001), Sambrook and Russell, eds. and Methods in Enzymology: Methods for molecular cloning in eukaryotic cells (2003) Purchio and G. C. Fareed. Each nucleic acid derivative represents a separate embodiment of the present invention.

Protein and/or peptide homology for any AA sequence listed herein is determined, in one embodiment, by methods well described in the art, including immunoblot analysis, or via computer algorithm analysis of AA sequences, utilizing any of a number of software packages available, via established methods. Some of these packages include the FASTA, BLAST, MPsrch or Scanps packages, and employ, in other embodiments, the use of the Smith and Waterman algorithms, and/or global/local or BLOCKS alignments for analysis, for example. Each method of determining homology represents a separate embodiment of the present invention.

In another embodiment, a recombinant peptide of the present invention is made by a process that comprises the step of chemically conjugating a peptide comprising the LLO protein or fragment thereof to a peptide comprising the BCR or a fragment thereof. In another embodiment, an LLO protein or fragment thereof is chemically conjugated to a peptide comprising the BCR or a fragment thereof. In another embodiment, a peptide comprising the LLO protein or fragment thereof is chemically conjugated to the BCR or a fragment thereof. In another embodiment, the LLO protein or fragment thereof is chemically conjugated to the BCR or a fragment thereof. Each possibility represents a separate embodiment of the present invention.

"Peptide" refers, in another embodiment, to a chain of AA connected with peptide bonds. In another embodiment, the term refers to a variant peptide molecule, containing any modification disclosed or enumerated herein. In another embodiment, the term refers to a molecule containing one or more moieties introduced by a chemical cross-linker. In another embodiment, the term refers to a peptide mimetic molecule. In another embodiment, the term refers to any other type of variant of a peptide molecule known in the art. Each possibility represents a separate embodiment of the present invention.

In another embodiment, the method used for conjugating the LLO protein, ActA protein, or fragment thereof to the BCR or fragment thereof is that described in Example 21. In another embodiment, another method known in the art is utilized. Methods for chemical conjugation of peptides to one another are well known in the art, and are described for, example, in (Biragyn, A and Kwak, L W (2001) Mouse models for lymphoma in "Current Protocols in Immunology" 20.6.1-20.6.30) and (Collawn, J. F. and Paterson, Y. (1989) Preparation of Anti-peptide antibodies. In Current Protocols in Molecular Biology. Supplement 6. Ed. F. M. Ausubel et. al. Greene Publishing/Wiley 11.14.1-11.15.3).

In another embodiment, the LLO protein, ActA protein, or fragment thereof is attached to the antigen or fragment thereof by chemical conjugation. In another embodiment, glutaraldehyde is used for the conjugation. In another embodiment, the conjugation is performed using any suitable method known in the art. Each possibility represents another embodiment of the present invention.

In another embodiment, fusion proteins of the present invention are prepared by any suitable method, including, for example, cloning and restriction of appropriate sequences or direct chemical synthesis by methods discussed below. In another embodiment, subsequences are cloned and the appropriate subsequences cleaved using appropriate restriction enzymes. The fragments are then ligated, in another embodiment, to produce the desired DNA sequence. In another embodiment, DNA encoding the fusion protein is produced using DNA amplification methods, for example polymerase chain reaction (PCR). First, the segments of the native DNA on either side of the new terminus are amplified separately. The 5' end of the one amplified sequence encodes the peptide linker, while the 3' end of the other amplified sequence also encodes the peptide linker. Since the 5' end of the first fragment is complementary to the 3' end of the second fragment, the two fragments (after partial purification, e.g. on LMP agarose) can be used as an overlapping template in a third PCR reaction. The amplified sequence will contain codons, the segment on the carboxy side of the opening site (now forming the amino sequence), the linker, and the sequence on the amino side of the opening site (now forming the carboxyl sequence). The insert is then ligated into a plasmid.

In another embodiment, the LLO protein, ActA protein, or fragment thereof and the BCR or fragment thereof are conjugated by a means known to those of skill in the art. In another embodiment, the BCR or fragment thereof is conjugated, either directly or through a linker (spacer), to the ActA protein or LLO protein. In another embodiment, the chimeric molecule is recombinantly expressed as a single-chain fusion protein.

In another embodiment, a fusion peptide of the present invention is synthesized using standard chemical peptide synthesis techniques. In another embodiment, the chimeric molecule is synthesized as a single contiguous polypeptide. In another embodiment, the LLO protein, ActA protein, or fragment thereof; and the BCR or fragment thereof are synthesized separately, then fused by condensation of the amino terminus of one molecule with the carboxyl terminus of the other molecule, thereby forming a peptide bond. In another embodiment, the ActA protein or LLO protein and antigen are each condensed with one end of a peptide spacer molecule, thereby forming a contiguous fusion protein.

In another embodiment, the peptides and proteins of the present invention are prepared by solid-phase peptide synthesis (SPPS) as described by Stewart et al. in Solid Phase Peptide Synthesis, 2nd Edition, 1984, Pierce Chemical Company, Rockford, Ill.; or as described by Bodanszky and Bodanszky (The Practice of Peptide Synthesis, 1984, Springer-Verlag, New York). In another embodiment, a suitably protected AA residue is attached through its carboxyl group to a derivatized, insoluble polymeric support, such as cross-linked polystyrene or polyamide resin. "Suitably protected" refers to the presence of protecting groups on both the alpha-amino group of the amino acid, and on any side chain functional groups. Side chain protecting groups are generally stable to the solvents, reagents and reaction conditions used throughout the synthesis, and are removable under conditions which will not affect the final peptide product. Stepwise synthesis of the oligopeptide is carried out by the removal of the N-protecting group from the initial AA, and couple thereto of the carboxyl end of the next AA in the sequence of the desired peptide. This AA is also suitably protected. The carboxyl of the incoming AA can be activated to react with the N-terminus of the support-bound AA by formation into a reactive group such as formation into a carbodiimide, a symmetric acid anhydride or an "active ester" group such as hydroxybenzotriazole or pentafluorophenly esters.

Examples of solid phase peptide synthesis methods include the BOC method which utilized tert-butyloxcarbonyl as the alpha-amino protecting group, and the FMOC method which utilizes 9-fluorenylmethyloxcarbonyl to protect the alpha-amino of the AA residues, both methods of which are well-known by those of skill in the art.

In another embodiment, incorporation of N- and/or C-blocking groups is achieved using protocols conventional to solid phase peptide synthesis methods. For incorporation of C-terminal blocking groups, for example, synthesis of the desired peptide is typically performed using, as solid phase, a supporting resin that has been chemically modified so that cleavage from the resin results in a peptide having the desired C-terminal blocking group. To provide peptides in which the C-terminus bears a primary amino blocking group, for instance, synthesis is performed using a p-methylbenzhydrylamine (MBHA) resin so that, when peptide synthesis is completed, treatment with hydrofluoric acid releases the desired C-terminally amidated peptide. Similarly, incorporation of an N-methylamine blocking group at the C-terminus is achieved using N-methylaminoethyl-derivatized DVB, resin, which upon HF treatment releases a peptide bearing an N-methylamidated C-terminus. Blockage of the C-terminus by esterification can also be achieved using conventional procedures. This entails use of resin/blocking group combination that permits release of side-chain peptide from the resin, to allow for subsequent reaction with the desired alcohol, to form the ester function. FMOC protecting group, in combination with DVB resin derivatized with methoxyalkoxybenzyl alcohol or equivalent linker, can be used for this purpose, with cleavage from the support being effected by TFA in dicholoromethane. Esterification of the suitably activated carboxyl function e.g. with DCC, can then proceed by addition of the desired alcohol, followed by deprotection and isolation of the esterified peptide product.

Incorporation of N-terminal blocking groups can be achieved while the synthesized peptide is still attached to the resin, for instance by treatment with a suitable anhydride and nitrile. To incorporate an acetyl blocking group at the N-terminus, for instance, the resin coupled peptide can be treated with 20% acetic anhydride in acetonitrile. The N-blocked peptide product can then be cleaved from the resin, deprotected and subsequently isolated.

In another embodiment, analysis of the peptide composition is conducted to verify the identity of the produced peptide. In another embodiment, AA composition analysis is conducted using high resolution mass spectrometry to determine the molecular weight of the peptide. Alternatively, or additionally, the AA content of the peptide is confirmed by hydrolyzing the peptide in aqueous acid, and separating, identifying and quantifying the components of the mixture using HPLC, or an AA analyzer. Protein sequencers, which sequentially degrade the peptide and identify the AA in order, can also be used to determine definitely the sequence of the peptide.

In another embodiment, prior to its use, the peptide is purified to remove contaminants. In another embodiment, the peptide is purified so as to meet the standards set out by the appropriate regulatory agencies and guidelines. Any one of a number of a conventional purification procedures can be used to attain the required level of purity, including, for example, reversed-phase high-pressure liquid chromatography (HPLC) using an alkylated silica column such as $C_4$-, $C_8$- or $C_{18}$-silica. A gradient mobile phase of increasing organic content is generally used to achieve purification, for example, acetonitrile in an aqueous buffer, usually containing a small amount of trifluoroacetic acid. Ion-exchange chromatography can be also used to separate peptides based on their charge.

Solid phase synthesis in which the C-terminal AA of the sequence is attached to an insoluble support followed by sequential addition of the remaining AA in the sequence is used, in another embodiment, for the chemical synthesis of the peptides of this invention. Techniques for solid phase synthesis are described by Barany and Merrifield in Solid-Phase Peptide Synthesis; pp. 3-284 in The Peptides: Analysis, Synthesis, Biology. Vol. 2: Special Methods in Peptide Synthesis, Part A., Merrifield, et al. J. Am. Chem. Soc., 85: 2149-2156 (1963), and Stewart et al., Solid Phase Peptide Synthesis, 2nd ed. Pierce Chem. Co., Rockford, Ill. (1984).

In another embodiment, fusion proteins of the present invention are synthesized using recombinant DNA methodology. In another embodiment, DNA encoding the fusion protein of the present invention is prepared by any suitable method, including, for example, cloning and restriction of appropriate sequences or direct chemical synthesis by methods such as the phosphotriester method of Narang et al. (1979, Meth. Enzymol. 68: 90-99); the phosphodiester method of Brown et al. (1979, Meth. Enzymol 68: 109-151); the diethylphosphoramidite method of Beaucage et al. (1981, Tetra. Lett., 22: 1859-1862); and the solid support method of U.S. Pat. No. 4,458,066.

In another embodiment, peptides of the present invention incorporate AA residues which are modified without affecting activity. In another embodiment, the termini are derivatized to include blocking groups, i.e. chemical substituents suitable to protect and/or stabilize the N- and C-termini from "undesirable degradation", a term meant to encompass any type of enzymatic, chemical or biochemical breakdown of the compound at its termini which is likely to affect the function of the compound, i.e. sequential degradation of the compound at a terminal end thereof.

In another embodiment, blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include $C_1$-$C_5$ branched or unbranched alkyl groups, acyl groups such as formyl and acetyl groups, as well as substituted forms thereof, such as the acetamidomethyl (Acm) group. Desamino AA analogs are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines ($—NH_2$), and mono- and di-alkyl amino groups such as methyl amino, ethylamino, dimethylamino, diethylamino, methylethylamino and the like are examples of C-terminal blocking groups. Descarboxylated AA analogues such as agmatine are also useful C-terminal blocking groups and can be either coupled to the peptide's C-terminal residue or used in place of it. In another embodiment, the free amino and carboxyl groups at the termini are removed altogether from the peptide to yield desamino and descarboxylated forms thereof without affect on peptide activity.

In another embodiment, other modifications are incorporated without adversely affecting the activity. In another embodiment, such modifications include, but are not limited to, substitution of one or more of the AA in the natural L-isomeric form with D-isomeric AA. In another embodiment, the peptide includes one or more D-amino acid resides, or comprises AA that are all in the D-form. Retro-inverso forms of peptides in accordance with the present invention are also contemplated, for example, inverted peptides in which all amino acids are substituted with D-amino acid forms.

In another embodiment, acid addition salts peptides of the present invention are utilized as functional equivalents thereof. In another embodiment, a peptide in accordance with the present invention treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tataric, citric, benzoic, cinnamie, mandelic, methanesulfonic, ethanesulfonic, p-toluenesulfonic, salicyclic and the like, to provide a water soluble salt of the peptide is suitable for use in the invention.

In another embodiment, modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated AA residues, e.g., phosphotyrosine, phosphoserine, or phosphothreonine.

In another embodiment, polypeptides are modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

In another embodiment, the present invention provides a method of inducing a humoral immune response in an animal against an antigen, comprising administering to the animal a peptide comprising an LLO protein or a fragment thereof and the antigen or a fragment thereof, thereby inducing a humoral immune response in an animal against an antigen. As provided herein, methods and compositions of the present invention are efficacious in producing antibodies to any antigen of interest (Example 22).

In another embodiment, the present invention provides an antiserum induced by a method of the present invention.

In another embodiment, the present invention provides a method of producing a monoclonal antibody, comprising inducing a humoral immune response in an animal by a method of the present invention, and generating a hybridoma from a B cell of the animal.

In another embodiment, the present invention provides a kit comprising an LLO protein, ActA protein, or fragment thereof fused to a BCR of fragment thereof, an applicator, and instructional material that describes use of the methods of the invention. Although model kits are described below, the contents of other useful kits will be apparent to the skilled artisan in light of the present disclosure. Each of these kits is contemplated within the present invention.

In another embodiment, the present invention provides a kit for eliciting an enhanced immune response to an antigen. The kit is used, in another embodiment, in the same manner as the methods disclosed herein for the present invention. In another embodiment, kit is used to administer an LLO protein, ActA protein, or fragment thereof fused to a BCR of fragment thereof. In another embodiment, the kit further comprises an applicator and an instructional material for the use of the kit. These instructions embody, in another embodiment, the examples provided herein.

In another embodiment, the present invention provides a kit for inducing a humoral immune response in an animal against an antigen. The kit is used, in another embodiment, in the same manner as the methods disclosed herein for the present invention

EXPERIMENTAL DETAILS SECTION

Example 1

LLO-Antigen Fusions Induce Anti-Tumor Immunity

Materials and Experimental Methods (Examples 1-2)

Cell Lines

The C57BL/6 syngeneic TC-1 tumor was immortalized with HPV-16 E6 and E7 and transformed with the c-Ha-ras oncogene. TC-1 expresses low levels of E6 and E7 and is highly tumorigenic. TC-1 was grown in RPMI 1640, 10% FCS, 2 mM L-glutamine, 100 U/ml penicillin, 100 μg/ml streptomycin, 100 μM nonessential amino acids, 1 mM sodium pyruvate, 50 micromolar (mcM) 2-ME, 400 microgram (mcg)/ml G418, and 10% National Collection Type Culture-109 medium at 37° with 10% $CO_2$. C3 is a mouse embryo cell from C57BL/6 mice immortalized with the complete genome of HPV 16 and transformed with pEJ-ras. EL-4/E7 is the thymoma EL-4 retrovirally transduced with E7.

L-Monocytogenes Strains and Propagation

Listeria strains used were Lm-LLO-E7 (hly-E7 fusion gene in an episomal expression system; FIG. 1A), Lm-E7 (single-copy E7 gene cassette integrated into Listeria genome), Lm-LLO-NP ("DP-L2028"; hly-NP fusion gene in an episomal expression system), and Lm-Gag ("ZY-18"; single-copy HIV-1 Gag gene cassette integrated into the chromosome). E7 was amplified by PCR using the primers 5'-GG CTCGAGCATGGAGATACACC-3' (SEQ ID No: 8; XhoI site is underlined) and 5'-GGGG ACTAGTTTATGGTTTCTGAGAACA-3' (SEQ ID No: 9; SpeI site is underlined) and ligated into pCR2.1 (Invitrogen, San Diego, Calif.). E7 was excised from pCR2.1 by XhoI/SpeI digestion and ligated into pGG-55. The hly-E7 fusion gene and the pluripotential transcription factor prfA were cloned into pAM401, a multicopy shuttle plasmid (Wirth R et al, J Bacteriol, 165: 831, 1986), generating pGG-55. The hly promoter drives the expression of the first 441 AA of the hly gene product, (lacking the hemolytic C-terminus, referred to below as "ΔLLO," and having the sequence set forth in SEQ ID No: 25), which is joined by the XhoI site to the E7 gene, yielding a hly-E7 fusion gene that is transcribed and secreted as LLO-E7. Transformation of a prfA negative strain of Listeria, XFL-7 (provided by Dr. Hao Shen, University of Pennsylvania), with pGG-55 selected for the retention of the plasmid in vivo (FIGS. 1A-B). The hly promoter and gene fragment were generated using primers 5'-GGGG GCTAGCCCTCCTTTGATTAGTATATTC-3' (SEQ ID No: 10; NheI site is underlined) and 5'-CTCC CTCGAGATCATAAATTTACTTCATC-3' (SEQ ID No: 11; XhoI site is underlined). The prfA gene was PCR amplified using primers 5'-GACTACAAGGACGATGACCGA-CAAGTGATAACCCGGGATCTAAATAAATCCGTTT-3' (SEQ ID No: 12; XbaI site is underlined) and 5'-CCC GTCGACCAGCTCTTCTTGGTGAAG-3' (SEQ ID No: 13; SalI site is underlined). Lm-E7 was generated by introducing an expression cassette containing the hly promoter and signal sequence driving the expression and secretion of E7 into the orfZ domain of the LM genome. E7 was amplified by PCR using the primers 5'-GC GGATCCCATGGAGATACACCTAC-3' (SEQ ID No: 43; BamHI site is underlined) and 5'-GC TCTAGATTATGGTTTCTGAG-3' (SEQ ID No: 44; XbaI site is underlined). E7 was then ligated into the pZY-21 shuttle vector. LM strain 10403S was transformed with the resulting plasmid, pZY-21-E7, which includes an expression cassette inserted in the middle of a 1.6-kb sequence that corresponds to the orfX, Y, Z domain of the LM genome. The homology domain allows for insertion of the E7 gene cassette into the orfZ domain by homologous recombination. Clones were screened for integration of the E7 gene cassette into the orfZ domain. Bacteria were grown in brain heart infusion medium with (Lm-LLO-E7 and Lm-LLO-NP) or without (Lm-E7 and ZY-18) chloramphenicol (20 μg/ml). Bacteria were frozen in aliquots at −80° C. Expression was verified by Western blotting (FIG. 2)

Western Blotting

Listeria strains were grown in Luria-Bertoni medium at 37° C. and were harvested at the same optical density measured at 600 nm. The supernatants were TCA precipitated and resuspended in 1× sample buffer supplemented with 0.1 N NaOH. Identical amounts of each cell pellet or each TCA-precipitated supernatant were loaded on 4-20% Tris-glycine SDS-PAGE gels (NOVEX, San Diego, Calif.). The gels were transferred to polyvinylidene difluoride and probed with an anti-E7 monoclonal antibody (mAb) (Zymed Laboratories, South San Francisco, Calif.), then incubated with HRP-conjugated anti-mouse secondary Ab (Amersham Pharmacia Biotech, Little Chalfont, U.K.), developed with Amersham ECL detection reagents, and exposed to Hyperfilm (Amersham Pharmacia Biotech).

Measurement of Tumor Growth

Tumors were measured every other day with calipers spanning the shortest and longest surface diameters. The mean of these two measurements was plotted as the mean tumor diameter in millimeters against various time points. Mice were sacrificed when the tumor diameter reached 20 mm. Tumor measurements for each time point are shown only for surviving mice.

Effects of *Listeria* Recombinants on Established Tumor Growth

Six- to 8-wk-old C57BL/6 mice (Charles River) received $2 \times 10^5$ TC-1 cells s.c. on the left flank. One week following tumor inoculation, the tumors had reached a palpable size of 4-5 mm in diameter. Groups of eight mice were then treated with 0.1 $LD_{50}$ i.p. Lm-LLO-E7 ($10^7$ CFU), Lm-E7 ($10^6$ CFU), Lm-LLO-NP ($10^7$ CFU), or Lm-Gag ($5 \times 10^5$ CFU) on days 7 and 14.

$^{51}$Cr Release Assay

C57BL/6 mice, 6-8 wk old, were immunized i.p. with $0.1 LD_{50}$ Lm-LLO-E7, Lm-E7, Lm-LLO-NP, or Lm-Gag. Ten days post-immunization, spleens were harvested. Splenocytes were established in culture with irradiated TC-1 cells (100:1, splenocytes:TC-1) as feeder cells; stimulated in vitro for 5 days, then used in a standard $^{51}$Cr release assay, using the following targets: EL-4, EL-4/E7, or EL-4 pulsed with E7H-2b peptide (RAHYNIVTF). E:T cell ratios, performed in triplicate, were 80:1, 40:1, 20:1, 10:1, 5:1, and 2.5:1. Following a 4-h incubation at 37° C., cells were pelleted, and 50 µl supernatant was removed from each well. Samples were assayed with a Wallac 1450 scintillation counter (Gaithersburg, Md.). The percent specific lysis was determined as [(experimental counts per minute–spontaneous counts per minute)/(total counts per minute–spontaneous counts per minute)]×100.

TC-1-Specific Proliferation

C57BL/6 mice were immunized with 0.1 $LD_{50}$ and boosted by i.p. injection 20 days later with 1 $LD_{50}$ Lm-LLO-E7, Lm-E7, Lm-LLO-NP, or Lm-Gag. Six days after boosting, spleens were harvested from immunized and naive mice. Splenocytes were established in culture at $5 \times 10^5$/well in flat-bottom 96-well plates with $2.5 \times 10^4$, $1.25 \times 10^4$, $6 \times 10^3$, or $3 \times 10^3$ irradiated TC-1 cells/well as a source of E7 Ag, or without TC-1 cells or with 10 µg/ml ConA. Cells were pulsed 45 h later with 0.5 µCi [$^3$H]thymidine/well. Plates were harvested 18 h later using a Tomtec harvester 96 (Orange, Conn.), and proliferation was assessed with a Wallac 1450 scintillation counter. The change in counts per minute was calculated as experimental counts per minute–no Ag counts per minute.

Flow Cytometric Analysis

C57BL/6 mice were immunized intravenously (i.v.) with 0.1 $LD_{50}$ Lm-LLO-E7 or Lm-E7 and boosted 30 days later. Three-color flow cytometry for CD8 (53-6.7, PE conjugated), CD62 ligand (CD62L; MEL-14, APC conjugated), and E7H-2 Db tetramer was performed using a FACSCalibur® flow cytometer with CellQuest® software (Becton Dickinson, Mountain View, Calif.). Splenocytes harvested 5 days after the boost were stained at room temperature (rt) with H-2 Db tetramers loaded with the E7 peptide (RAHYNIVTF) or a control (HIV-Gag) peptide. Tetramers were used at a 1/200 dilution and were provided by Dr. Larry R. Pease (Mayo Clinic, Rochester, Minn.) and by the National Institute of Allergy and Infectious Diseases Tetramer Core Facility and the National Institutes of Health AIDS Research and Reference Reagent Program. Tetramer$^+$, CD8$^+$, CD62L$^{low}$ cells were analyzed.

Depletion of Specific Immune Components

CD8$^+$ cells, CD4$^+$ cells and IFN were depleted in TC-1-bearing mice by injecting the mice with 0.5 mg per mouse of mAb: 2.43, GK1.5, or xmg1.2, respectively, on days 6, 7, 8, 10, 12, and 14 post-tumor challenge. CD4$^+$ and CD8$^+$ cell populations were reduced by 99% (flow cytometric analysis). CD25$^+$ cells were depleted by i.p. injection of 0.5 mg/mouse anti-CD25 mAb (PC61, provided by Andrew J. Caton) on days 4 and 6. TGF was depleted by i.p. injection of the anti-TGF-mAb (2G7, provided by H. I. Levitsky), into TC-1-bearing mice on days 6, 7, 8, 10, 12, 14, 16, 18, and 20. Mice were treated with $10^7$ Lm-LLO-E7 or Lm-E7 on day 7 following tumor challenge.

Adoptive Transfer

Donor C57BL/6 mice were immunized and boosted 7 days later with 0.1 $LD_{50}$ Lm-E7 or Lm-Gag. The donor splenocytes were harvested and passed over nylon wool columns to enrich for T cells. CD8$^+$ T cells were depleted in vitro by incubating with 0.1 µg 2.43 anti-CD8 mAb for 30 min at rt. The labeled cells were then treated with rabbit complement. The donor splenocytes were >60% CD4$^+$ T cells (flow cytometric analysis). TC-1 tumor-bearing recipient mice were immunized with 0.1 $LD_{50}$ 7 days post-tumor challenge. CD4$^+$-enriched donor splenocytes ($10^7$) were transferred 9 days after tumor challenge to recipient mice by i.v. injection.

B16F0-Ova Experiment

24 C57BL/6 mice were inoculated with $5 \times 10^5$ B16F0-Ova cells. On days 3, 10 and 17, groups of 8 mice were immunized with 0.1 $LD_{50}$ Lm-OVA ($10^6$ cfu), Lm-LLO-OVA ($10^8$ cfu) and eight animals were left untreated.

Statistics

For comparisons of tumor diameters, mean and SD of tumor size for each group were determined, and statistical significance was determined by Student's t test. $p \leq 0.05$ was considered significant.

Results

Figure 3A:
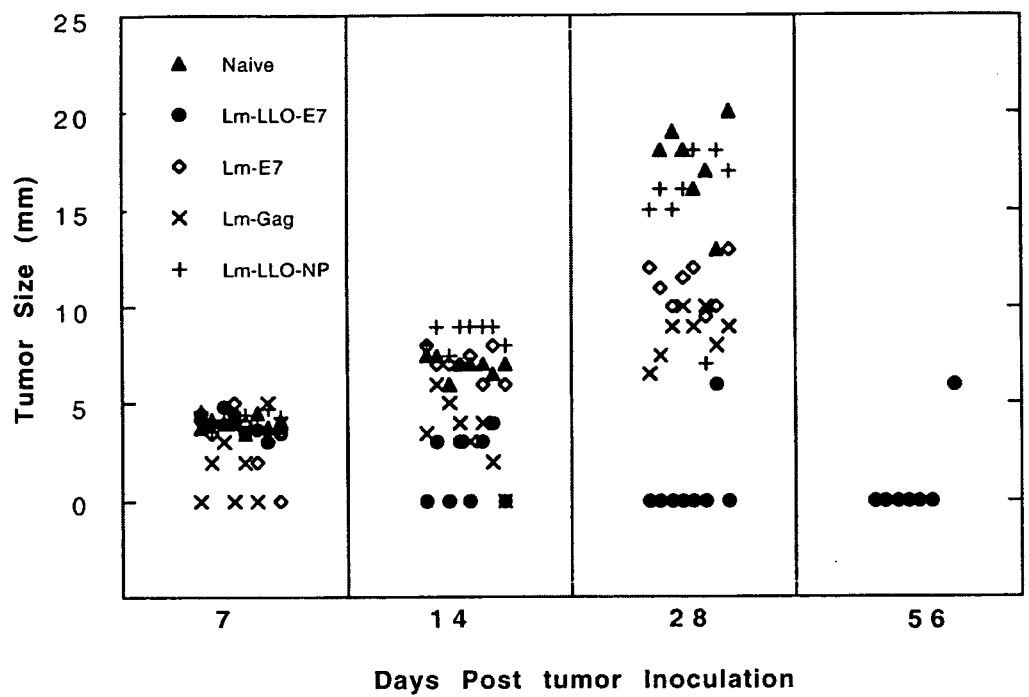
FIG. 3. A. Tumor immunotherapeutic efficacy of LLO-E7 fusions. Tumor size in millimeters in mice is shown at 7, 14, 21, 28 and 56 days post tumor-inoculation. Naive mice: open-circles; Lm-LLO-E7: filled circles; Lm-E7: squares; Lm-Gag: open diamonds; and Lm-LLO-NP: filled triangles. B. Tumor immunotherapeutic efficacy of LLO-Ova fusions.

Lm-E7 and Lm-LLO-E7 were compared for their abilities to impact on TC-1 growth. Subcutaneous tumors were established on the left flank of C57BL/6 mice. Seven days later tumors had reached a palpable size (4-5 mm). Mice were vaccinated on days 7 and 14 with 0.1 $LD_{50}$ Lm-E7, Lm-LLO-E7, or, as controls, Lm-Gag and Lm-LLO-NP. Lm-LLO-E7 induced complete regression of 75% of established TC-1 tumors, while the other 2 mice in the group controlled their tumor growth (FIG. 3A). By contrast, immunization Lm-E7 and Lm-Gag did not induce tumor regression. This experiment was repeated multiple times, always with very similar results. In addition, similar results were achieved for Lm-LLO-E7 under different immunization protocols. In another experiment, a single immunization was able to cure mice of established 5 mm TC-1 tumors.

In other experiments, similar results were obtained with 2 other E7-expressing tumor cell lines: C3 and EL-4/E7. To confirm the efficacy of vaccination with Lm-LLO-E7, animals that had eliminated their tumors were re-challenged with TC-1 or EL-4/E7 tumor cells on day 60 or day 40, respectively. Animals immunized with Lm-LLO-E7 remained tumor free until termination of the experiment (day 124 in the case of TC-1 and day 54 for EL-4/E7).

Figure 3B:
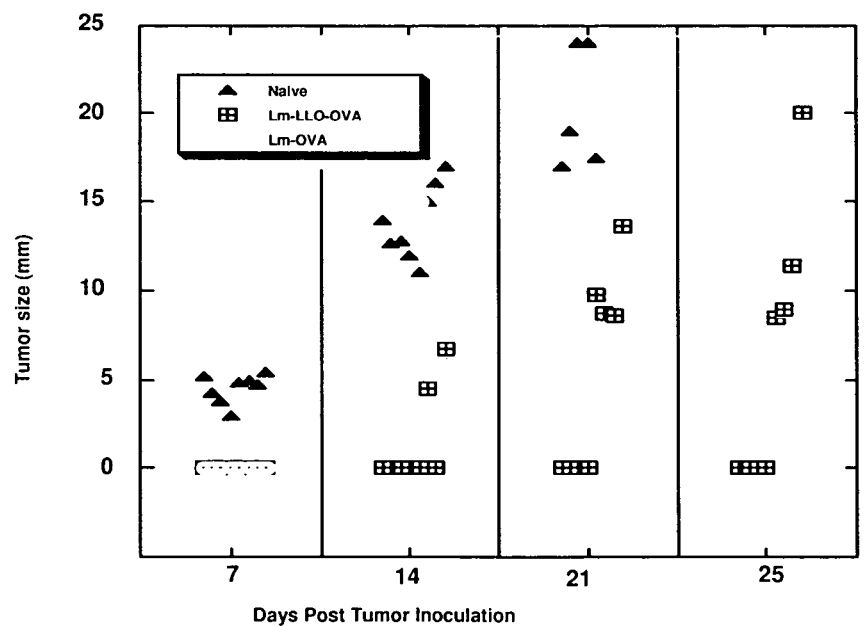

A similar experiment was performed with the chicken ovalbumin antigen (OVA). Mice were immunized with either Lm-OVA or Lm-LLO-OVA, then challenged with either an EL-4 thymoma engineered to express OVA or the very aggressive murine melanoma cell line B16F0-Ova, which has very low MHC class I expression. In both cases, Lm-LLO-OVA, but not Lm-OVA, induced the regression of established tumors. For example, at the end of the B16F0 experiment (day 25), all the mice in the naive group and the Lm-OVA group had died. All the Lm-LLO-OVA mice were alive, and 50% of them were tumor free. (FIG. 3B).

Thus, expression of an antigen gene as a fusion protein with ΔLLO enhances the immunogenicity of the antigen.

Example 2

Lm-LLO-E7 Treatment Elicits TC-1 Specific Splenocyte Proliferation

Figure 4:
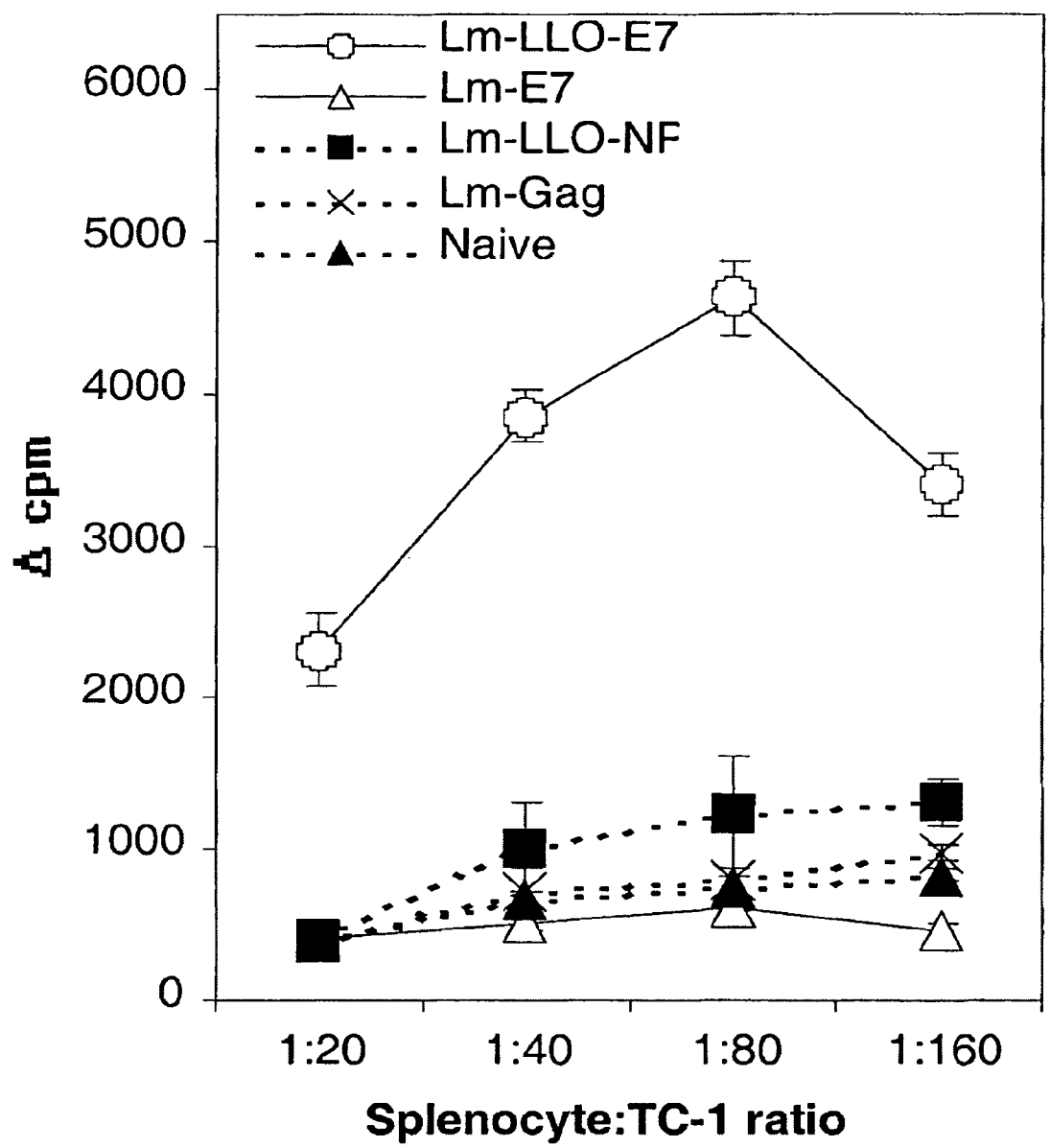
FIG. 4. Splenocytes from Lm-LLO-E7-immunized mice proliferate when exposed to TC-1 cells. C57BL/6 mice were immunized and boosted with Lm-LLO-E7, Lm-E7, or control rLm strains. Splenocytes were harvested 6 days after the boost and plated with irradiated TC-1 cells at the ratios shown. The cells were pulsed with $^3$H thymidine and harvested. Cpm is defined as (experimental cpm)–(no-TC-1 control).

To measure induction of T cells by Lm-E7 with Lm-LLO-E7, TC-1-specific proliferative responses of splenocytes from rLm-immunized mice, a measure of antigen-specific immunocompetence, were assessed. Splenocytes from Lm-LLO-E7-immunized mice proliferated when exposed to irradiated TC-1 cells as a source of E7, at splenocyte: TC-1 ratios of 20:1, 40:1, 80:1, and 160:1 (FIG. 4). Conversely, splenocytes from Lm-E7 and rLm control immunized mice exhibited only background levels of proliferation.

Example 3

Fusion of NP to LLO Enhances its Immunogenicity

Materials and Experimental Methods

Figure 2:
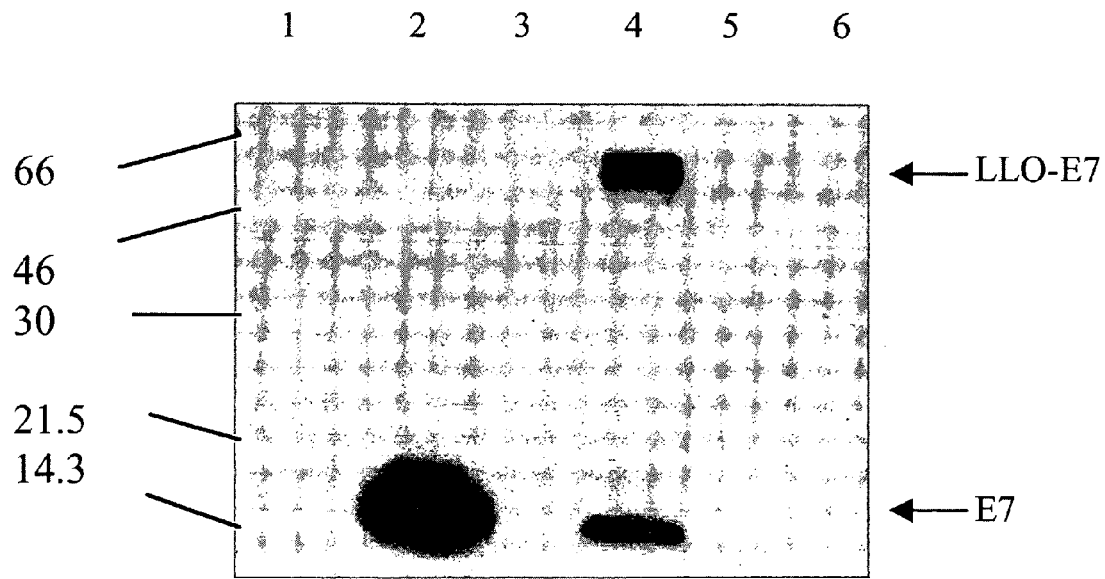
FIG. 2. Lm-E7 and Lm-LLO-E7 secrete E7. Lm-Gag (lane 1), Lm-E7 (lane 2), Lm-LLO-NP (lane 3), Lm-LLO-E7 (lane 4), XFL-7 (lane 5), and 10403S (lane 6) were grown overnight at 37° C. in Luria-Bertoni broth. Equivalent numbers of bacteria, as determined by OD at 600 nm absorbance, were pelleted and 18 ml of each supernatant was TCA precipitated. E7 expression was analyzed by Western blot. The blot was probed with an anti-E7 mAb, followed by HRP-conjugated anti-mouse (Amersham), then developed using ECL detection reagents.

Lm-LLO-NP was prepared as depicted in FIG. 1, except that influenza nucleoprotein (NP) replaced E7 as the antigen. 32 BALB/c mice were inoculated with $5 \times 10^5$ RENCA-NP tumor cells. RENCA-NP is a renal cell carcinoma retrovirally transduced with influenza nucleoprotein NP (described in U.S. Pat. No. 5,830,702, which is incorporated herein by reference). After palpable macroscopic tumors had grown on day 10, eight animals in each group were immunized i.p. with 0.1 $LD_{50}$ of the respective *Listeria* vector. The animals received a second immunization one week later.

Results

Figure 5:
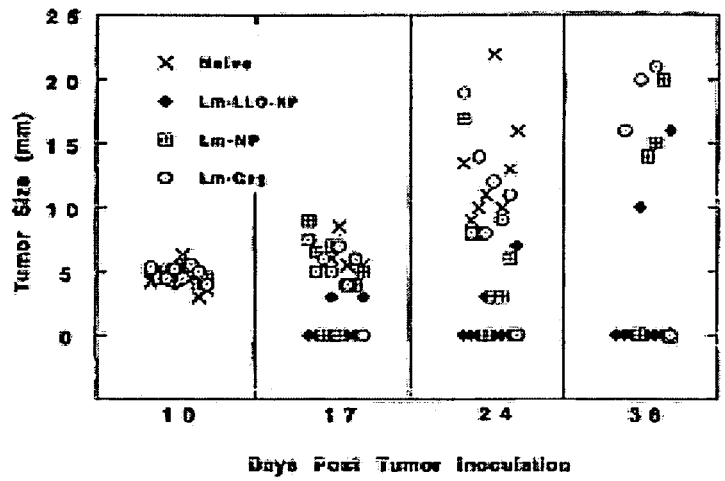
FIG. 5. Tumor immunotherapeutic efficacy of NP antigen expressed in LM. Tumor size in millimeters in mice is shown at 10, 17, 24, and 38 days post tumor-inoculation. Naive mice: X's; mice administered Lm-LLO-NP: filled diamonds; Lm-NP: squares; Lm-Gag: open circles.

In order to confirm the generality of the finding that fusing LLO to an antigen confers enhanced immunity, Lm-LLO-NP and Lm-NP (similar to the Lm-E7 vectors) were constructed, and the vectors were compared for ability to induce tumor regression, with Lm-Gag (isogenic with Lm-NP except for the antigen expressed) as a negative control. As depicted in FIG. 5, 6/8 of the mice that received Lm-LLO-NP were tumor free. By contrast, only 1/8 and 2/8 mice in the Lm-Gag and Lm-NP groups, respectively, were tumor free. All the mice in the naive group had large tumors or had died by day 40. Thus, enhancement of immunogenicity of an antigen by fusion to LLO is not restricted to E7, but rather is a general phenomenon.

Example 4

Figure 6:
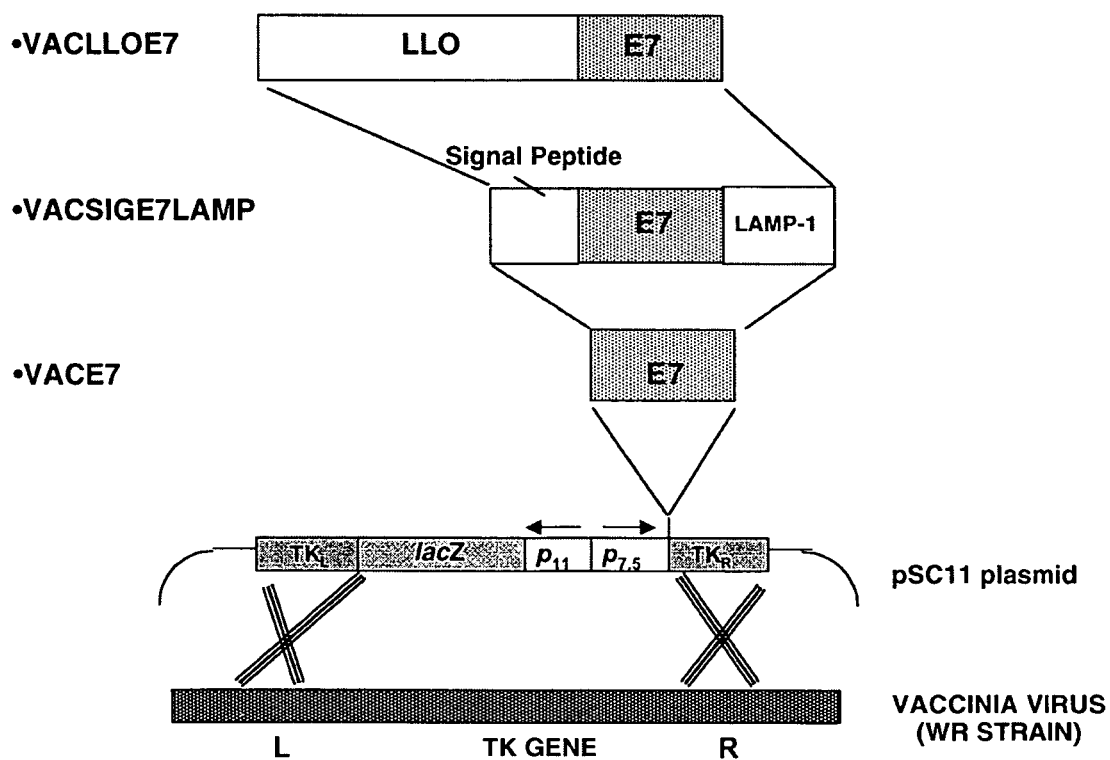
FIG. 6. Depiction of vaccinia virus constructs expressing different forms of HPV16 E7 protein.

Enhancement of Immunogenicity by Fusion of an Antigen to LLO does not Require a *Listeria* Vector Materials and Experimental Methods Construction of Vac-SigE7Lamp The WR strain of vaccinia was used as the recipient and the fusion gene was excised from the Listerial plasmid and inserted into pSC II under the control of the p75 promoter. This vector was chosen because it is the transfer vector used for the vaccinia constructs Vac-SigE7Lamp and Vac-E7 and would therefore allow direct comparison with Vac-LLO-E7. In this way all three vaccinia recombinants would be expressed under control of the same earlyaate compound promoter p7.5. In addition, SC11 allows the selection of recombinant viral plaques to TK selection and beta-galactosidase screening. FIG. 6 depicts the various vaccinia constructs used in these experiments. Vac-SigE7Lamp is a recombinant vaccinia virus that expressed the E7 protein fused between lysosomal associated membrane protein (LAMP-1) signal sequence and sequence from the cytoplasmic tail of LAMP-1. It was designed to facilitate the targeting of the antigen to the MHC class II pathway.

The following modifications were made to allow expression of the gene product by vaccinia: (a) the T5XT sequence that prevents early transcription by vaccinia was removed from the 5' portion of the LLO-E7 sequence by PCR; and (b) an additional XmaI restriction site was introduced by PCR to allow the final insertion of LLO-E7 into SC11. Successful introduction of these changes (without loss of the original sequence that encodes for LLO-E7) was verified by sequencing. The resultant pSCI 1-E7 construct was used to transfect the TK-ve cell line CV1 that had been infected with the wild-type vaccinia strain, WR. Cell lysates obtained from this co-infection/transfection step contain vaccinia recombinants that were plaque-purified 3 times. Expression of the LLO-E7 fusion product by plaque purified vaccinia was verified by Western blot using an antibody directed against the LLO protein sequence. In addition, the ability of Vac-LLO-E7 to produce $CD8^+$ T cells specific to LLO and E7 was determined using the LLO (91-99) and E7 (49-57) epitopes of Balb/c and C57/BL6 mice, respectively. Results were confirmed in a chromium release assay.

Results

Figure 7:
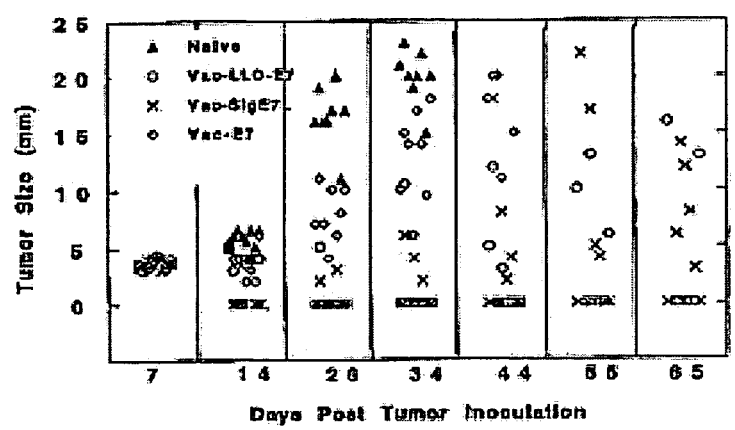
FIG. 7. VacLLOE7 causes long-term regression of tumors established from 2×10$^5$ TC-1 cells injected s.c. into C57BL/6 mice. Mice were injected 11 and 18 days after tumor challenge with 10$^7$ PFU of VacLLOE7, VacSigE7LAMP-1, or VacE7/mouse i.p. or were left untreated (naive). 8 mice per treatment group were used, and the cross section for each tumor (average of 2 measurements) is shown for the indicated days after tumor inoculation.

To determine whether enhancement of immunogenicity by fusion of an antigen to LLO requires a *Listeria* vector, a vaccinia vector expressing E7 as a fusion protein with a non-hemolytic truncated form of LLO (ΔLLO) was constructed. Tumor rejection studies were performed with TC-1 following the protocol described for Example 1. Two experiments were performed with differing delays before treatment was started. In one experiment, treatments were initiated when the tumors were about 3 mm in diameter (FIG. 7). As of day 76, 50% of the Vac-LLO-E7 treated mice were tumor free, while only 25% of the Vac-SigE7Lamp mice were tumor free. In other experiments, ΔLLO-antigen fusions were more immunogenic than E7 peptide mixed with SBAS2 or unmethylated CpG oligonucleotides in a side-by-side comparison.

These results show that (a) fusion of ΔLLO-antigen fusions are immunogenic not only in the context of *Listeria*, but also in other contexts; and (b) the immunogenicity of ΔLLO-antigen fusions compares favorably with other accepted vaccine approaches.

Example 5

ActA-E7 Fusions Confer Anti-Tumor Immunity

Materials and Experimental Methods

Construction of Lm-actA-E7

Figure 8:
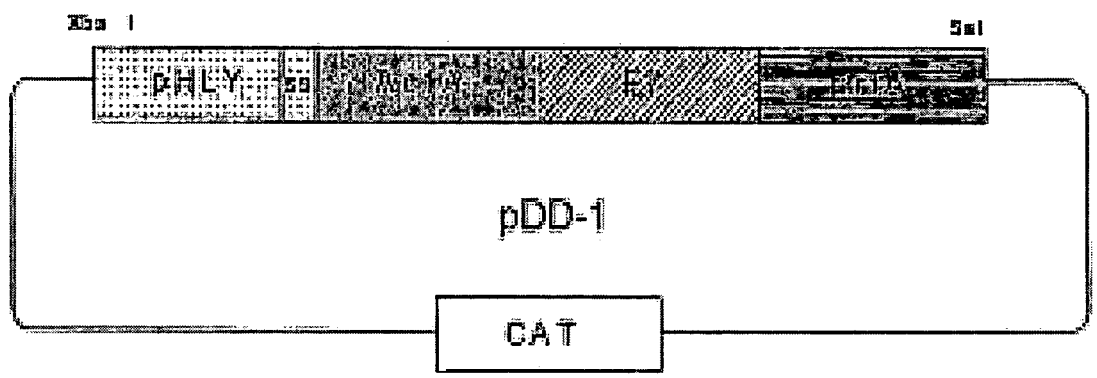
FIG. 8. Schematic representation of the pActA-E7 expression system used to express and secrete E7 from recombinant *Listeria* bacteria. The hly promoter (pHLY) drives expression, the prfA gene is used to select retention of the plasmid by recombinant *Listeria* in vivo.

Lm-actA-E7 is a recombinant strain of LM, comprising a plasmid that expresses the E7 protein fused to a truncated version of the actA protein. Lm-actA-E7 was generated by introducing a plasmid vector pDD-1 constructed by modifying pDP-2028 into LM. pDD-1 comprises an expression cassette expressing a copy of the 310 bp hly promoter and the hly signal sequence (ss), which drives the expression and secretion of actA-E7; 1170 bp of the actA gene that comprises four PEST sequences (SEQ ID NO: 24) (the truncated ActA polypeptide consists of the first 390 AA of the molecule, SEQ ID NO: 23); the 300 bp HPV E7 gene; the 1019 bp prfA gene (controls expression of the virulence genes); and the CAT gene (chloramphenicol resistance gene) for selection of transformed bacteria clones. (FIG. 8) (Sewell et al. (2004), Arch. Otolaryngol. Head Neck Surg., 130: 92-97).

The hly promoter (pHly) and gene fragment were PCR amplified from pGG55 (Example 1) using primer 5'-GGGG<u>TCTAGA</u>CCTCCTTTGATTAGTATATTC-3' (Xba I site is underlined; SEQ ID NO: 14) and primer 5'-ATCTTCGC-TATCTGTCGCCGC<u>GGCGCGT</u>GCTTCAGTTTGTTGCGC-'3 (Not I site is underlined. The first 18 nucleotides are the ActA gene overlap; SEQ ID NO: 15). The actA gene was PCR amplified from the LM 10403s wildtype genome using primer 5'-GCGCAA-CAAACTGAAGCAGCGGCC<u>GCGGC</u>GACAGATAGCGAAGAT-3' (NotI site is underlined; SEQ ID NO: 16) and primer 5'-TGTAGGTG-TATCTCCATG<u>CTCGAG</u>AGCTAGGCGATCAATTTC-3' (XhoI site is underlined; SEQ ID NO: 17). The E7 gene was PCR amplified from pGG55 (pLLO-E7) using primer 5'-GGAATTGATCGCCTAGCT<u>CTCGAG</u>CATGGAGATACACCTACA-3' (XhoI site is underlined; SEQ ID NO: 18) and primer 5'-AAACGGATT-TATTTAGAT<u>CCCGGG</u>TTATGGTTTCTGAGAACA-3' (XmaI site is underlined; SEQ ID NO: 19). The prfA gene was PCR amplified from the LM 10403s wild-type genome using primer 5'-TGTTCTCAGAAACCATAA<u>CCCGGG</u>ATCTAAATAAATCCGTTT-3' (XmaI site is underlined; SEQ ID NO: 20) and primer 5'-GGGGG<u>TCGAC</u>CAGCTCTTCTTGGTGAAG-3' (SalI site is underlined; SEQ ID NO: 21). The hly promoter was fused to the actA gene (pHly-actA) was PCR generated and amplified from purified pHly DNA and purified actA DNA using the upstream pHly primer (SEQ ID NO: 14) and downstream actA primer (SEQ ID NO: 17).

The E7 gene fused to the prfA gene (E7-prfA) was PCR generated and amplified from purified E7 DNA and purified prfA DNA using the upstream E7 primer (SEQ ID NO: 18) and downstream prfA gene primer (SEQ ID NO: 21).

The pHly-actA fusion product fused to the E7-prfA fusion product was PCR generated and amplified from purified fused pHly-actA DNA product and purified fused E7-prfA DNA product using the upstream pHly primer (SEQ ID NO: 14) and downstream prfA gene primer (SEQ ID NO: 21) and ligated into pCR11 (Invitrogen, La Jolla, Calif.). Competent E. coli (TOP10'F, Invitrogen, La Jolla, Calif.) were transformed with pCRII-ActAE7. After lysis and isolation, the plasmid was screened by restriction analysis using BamHI (expected fragment sizes 770 bp and 6400 bp (or when the insert was reversed into the vector: 2500 bp and 4100 bp)) and BstXI (expected fragment sizes 2800 bp and 3900 bp) and also screened with PCR analysis using the upstream pHly primer (SEQ ID NO: 14) and the downstream prfA gene primer (SEQ ID NO: 21).

The pHly-ActA-E7-PrfA DNA insert was excised from pCRII by double digestion with Xba I and Sal I and ligated into pDP-2028 also digested with Xba I and Sal I. After transforming TOP10'F competent E. coli (Invitrogen, La Jolla, Calif.) with expression system pActAE7, chloramphenicol resistant clones were screened by PCR analysis using the upstream pHly primer (SEQ ID NO: 14) and the downstream PrfA gene primer (SEQ ID NO: 21). A clone comprising pActAE7 was grown in brain heart infusion medium (with chloramphenicol (20 mcg (microgram)/ml (milliliter), Difco, Detroit, Mich.) and pActAE7 was isolated from the bacteria cell using a midiprep DNA purification system kit (Promega, Madison, Wis.). A prfA-negative strain of penicillin-treated Listeria (strain XFL-7) was transformed with expression system pActAE7, as described in Ikonomidis et al. (1994, J. Exp. Med. 180: 2209-2218) and clones were selected for the retention of the plasmid in vivo. Clones were grown in brain heart infusion with chloramphenicol (20 mcg/ml) at 37° C. Bacteria were frozen in aliquots at −80° C.

Immunoblot Verification of Antigen Expression

Figure 9:
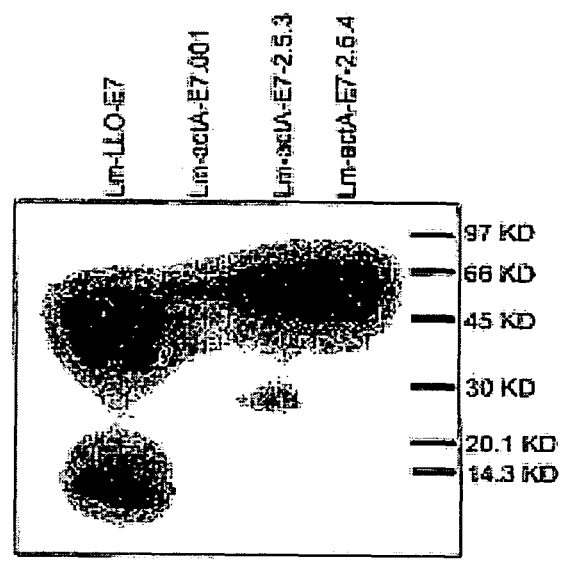
FIG. 9. Western blot demonstrating that Lm-ActA-E7 secretes E7. Lane 1: Lm-LLO-E7; lane 2: Lm-ActA-E7.001; lane 3; Lm-ActA-E7-2.5.3; lane 4: Lm-ActA-E7-2.5.4.

To verify that Lm-ActA-E7 secretes ActA-E7, (about 64 kD), Listeria strains were grown in Luria-Bertoni (LB) medium at 37° C. Protein was precipitated from the culture supernatant with trichloroacetic acid (TCA) and resuspended in 1× sample buffer with 0.1N sodium hydroxide. Identical amounts of each TCA precipitated supernatant were loaded on 4% to 20% Tris-glycine sodium dodecyl sulfate-polyacrylamide gels (NOVEX, San Diego, Calif.). Gels were transferred to polyvinylidene difluoride membranes and probed with 1:2500 anti-E7 monoclonal antibody (Zymed Laboratories, South San Francisco, Calif.), then with 1:5000 horseradish peroxidase-conjugated anti-mouse IgG (Amersham Pharmacia Biotech, Little Chalfont, England). Blots were developed with Amersham enhanced chemiluminescence detection reagents and exposed to autoradiography film (Amersham). (FIG. 9).

Results

Figure 10:
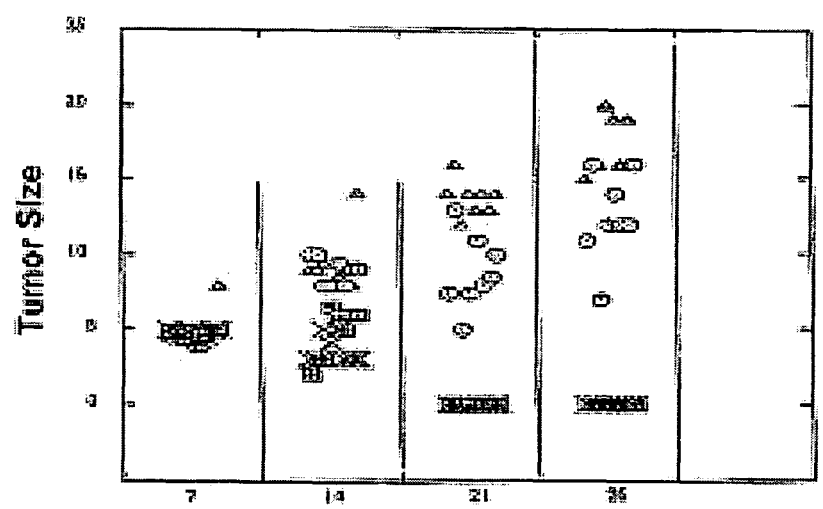
FIG. 10. Graph depicting tumor size in mice administered Lm-ActA-E7 (rectangles), Lm-E7 (ovals), Lm-LLO-E7 (X), and naive mice (non-vaccinated; solid triangles).

To compare the anti-tumor immunity induced by Lm-ActA-E7 versus Lm-LLO-E7, 2×10$^5$ TC-1 tumor cells were implanted subcutaneously in mice and allowed to grow to a palpable size (approximately 5 millimeters [mm]). Mice were immunized i.p. with one LD$_{50}$ of either Lm-ActA-E7 (5×10$^8$ CFU). Lm-LLO-E7 (10$^8$ CFU) or Lm-E7 (10$^6$ CFU) on days 7 and 14. By day 26, all of the animals in the Lm-LLO-E7 and Lm-ActA-E7 were tumor free and remained so, whereas all of the naive animals and the animals immunized with Lm-E7 grew large tumors (FIG. 10).

Example 6

Fusion of E7 to LLO or ActA Enhances E7-Specific Immunity and Generates Tumor-Infiltrating E7-Specific CD8$^+$ Cells Materials and Experimental Methods 500 mcl (microliter) of MATRIGEL®, comprising 100 mcl of 2×10$^5$ TC-1 tumor cells in phosphate buffered saline (PBS) plus 400 mcl of MATRIGEL® (BD Biosciences, Franklin Lakes, N.J.) were implanted subcutaneously on the left flank of 12 C57BL/6 mice (n=3). Mice were immunized intraperitoneally on day 7, 14 and 21, and spleens and tumors were harvested on day 28. Tumor MATRIGELs were removed from the mice and incubated at 4° C. overnight in tubes containing 2 milliliters (ml) of RP 10 medium on ice. Tumors were minced with forceps, cut into 2 mm blocks, and incubated at 37° C. for 1 hour with 3 ml of enzyme mixture (0.2 mg/ml collagenase-P, 1 mg/ml DNAse-1 in PBS). The tissue suspension was filtered through nylon mesh and washed with 5% fetal bovine serum+0.05% of NaN$_3$ in PBS for tetramer and IFN-gamma staining.

Splenocytes and tumor cells were incubated with 1 micromole (mcm) E7 peptide for 5 hours in the presence of brefeldin A at $10^7$ cells/ml. Cells were washed twice and incubated in 50 mcl of anti-mouse Fc receptor supernatant (2.4 G2) for 1 hour or overnight at 4° C. Cells were stained for surface molecules CD8 and CD62L, permeabilized, fixed using the permeabilization kit Golgi-stop® or Golgi-Plug® (Pharmingen, San Diego, Calif.), and stained for IFN-gamma. 500,000 events were acquired using two-laser flow cytometer FACS-Calibur and analyzed using Cellquest Software (Becton Dickinson, Franklin Lakes, N.J.). Percentages of IFN-gamma secreting cells within the activated ($CD62L^{low}$) $CD8^+$ T cells were calculated.

For tetramer staining, H-2 $D^b$ tetramer was loaded with phycoerythrin (PE)-conjugated E7 peptide (RAHYNIVTF, SEQ ID NO: 22), stained at rt for 1 hour, and stained with anti-allophycocyanin (APC) conjugated MEL-14 (CD62L) and FITC-conjugated CD8β at 4° C. for 30 min. Cells were analyzed comparing tetramer$^+$CD8$^+$ $CD62L^{low}$ cells in the spleen and in the tumor.

Results

Figure 11:
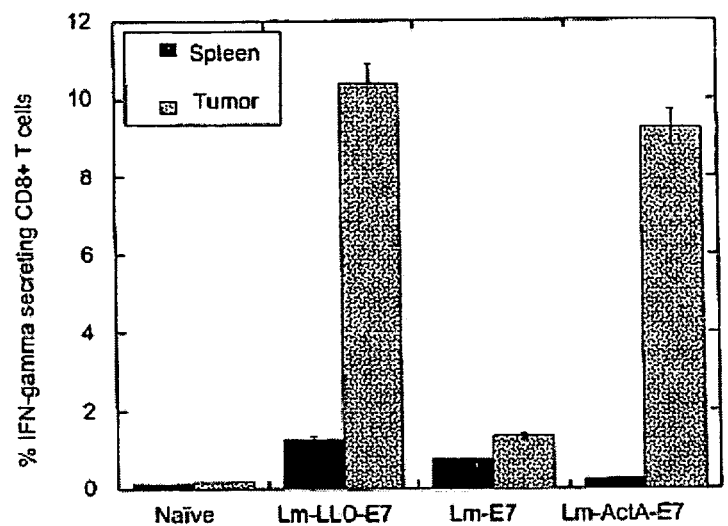
FIG. 11. Graph depicting the induction of E7 specific IFN-gamma secreting CD8$^+$ T cells in the spleens and tumors of mice administered TC-1 tumor cells and subsequently administered Lm-E7, Lm-LLO-E7, Lm-ActA-E7 or no vaccine (naive).
Figure 12:
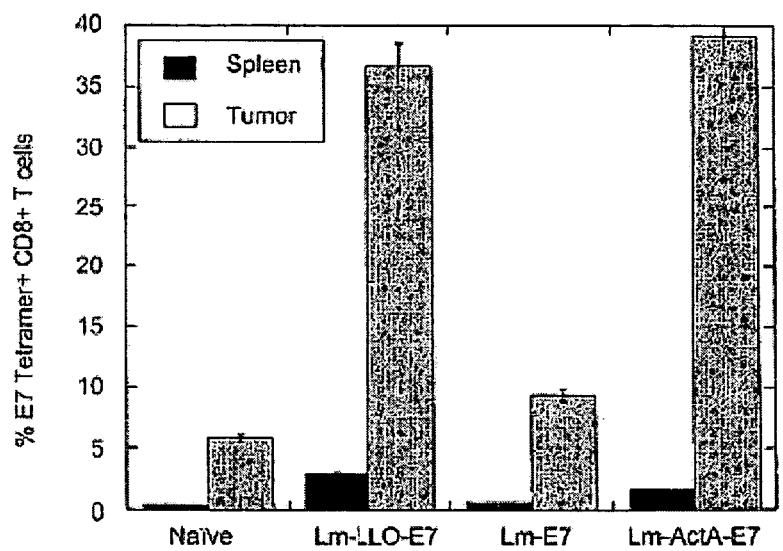
FIG. 12. Graph depicting the induction and penetration of E7 specific CD8$^+$ cells in the spleens and tumors of mice administered TC-1 cells and subsequently administered a recombinant *Listeria* vaccine (naive, Lm-LLO-E7, Lm-E7, Lm-ActA-E7).

To analyze the ability of Lm-ActA-E7 to enhance antigen specific immunity, mice were implanted with TC-1 tumor cells and immunized with either Lm-LLO-E7 ($1\times10^7$ CFU), Lm-E7 ($1\times10^6$ CFU), or Lm-ActA-E7 ($2\times10^8$ CFU), or were untreated (naïve). Tumors of mice from the Lm-LLO-E7 and Lm-ActA-E7 groups contained a higher percentage of IFN-gamma-secreting CD8$^+$ T cells (FIG. 11) and tetramer-specific CD8$^+$ cells (FIG. 12) than in mice administered Lm-E7 or naive mice.

Thus, Lm-LLO-E7 and Lm-ActA-E7 are both efficacious at induction of tumor-infiltrating CD8$^+$ T cells and tumor regression.

Example 7

E6/E7 Transgenic Mouse Phenotype: a Model for Spontaneous Tumor Growth and Tolerance to a Tumor Antigen Materials and Experimental Methods Several C57BL/6 mouse zygotes were injected with plasmids containing the HPV-16 E6/E7 gene under the control of the thyroglobulin promoter (provided by M Parmentier, Brussels). Tail clippings of several litters were screened via PCR for the E6/E7 gene. The E7 gene and the thyroglobulin promoter were integrated into the majority of the progeny. Positive mosaic E7 transgenic mice were then selected for F0×wild type breeding. Subsequent F1 generations were screened, via PCR, for the presence of the E7 gene. E7 positive pups generated from F0×wt breeding pairs were selected for F1×F1 breeding. The zygosity of F1 breeding pair derived generations was determined by Taqman real-time PCR and the ΔΔCt method (Charles River, 2001). Homozygous E7 transgenic mice were selected for F2×F2 breeding. The subsequent F3 generation was screened via Taqman real-time PCR and backcrossing to confirm fidelity of homozygosity. The levels of gene copy number and transgene expression of the E7 gene was assessed for every homozygous line using Taqman real-time PCR. After six back-crossings, these lines were used as the parents of the colony. Transgene expression was further confirmed by appearance of thyroid hyperplasia, as described in the Results section.

Results

Figure 13:
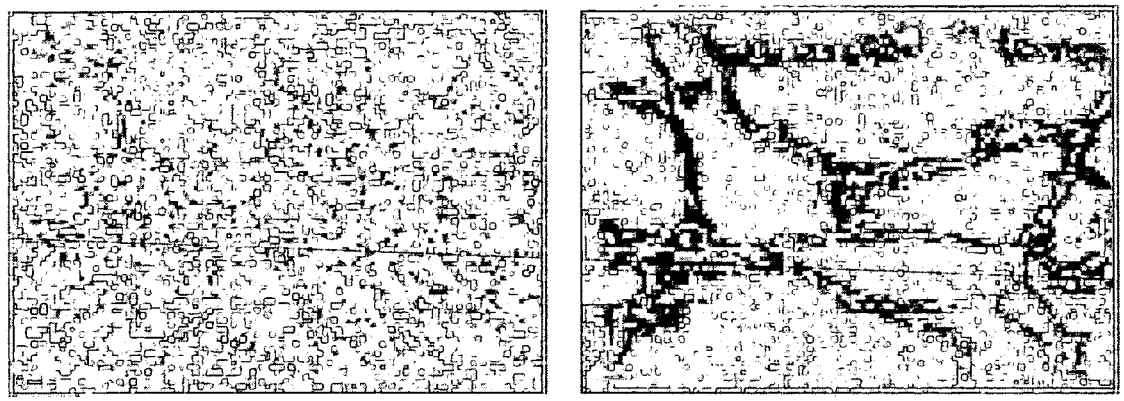
FIG. 13. E6/E7 transgenic mice develop tumors in their thyroid, where the E7 gene is expressed. Mice were sacrificed at 3 months and had their thyroids removed, sectioned, and stained by hematoxylin and eosin. A. Left panel: normal thyroid at 20× magnification. Follicles are of normal size and lined with cuboidal cells with abundant pink cytoplasm (arrow). Right panel: E6/E7 transgenic mouse thyroid. Note the greatly enlarged follicles because of the increased production of colloid. The cuboidal cells lining the follicles are smaller with very little cytoplasm.

E6/E7 transgenic mice were generated, and their phenotype assessed. The mice began to develop thyroid hyperplasia at 8 weeks and palpable goiters at 6 months. By 6 to 8 months, most mice exhibited thyroid cancer. Transgenic mice sacrificed at 3 months of age exhibited de-differentiation of the normal thyroid architecture, indicative of an early stage of cancer. The enlarged, de-differentiated cells were filled with colloid, where thyroid hormones accumulate (FIG. 13).

Example 8

E7 is Expressed in Medullary Thymic Epithelial Cells of E6/E7 Transgenic Mice

Figure 14:
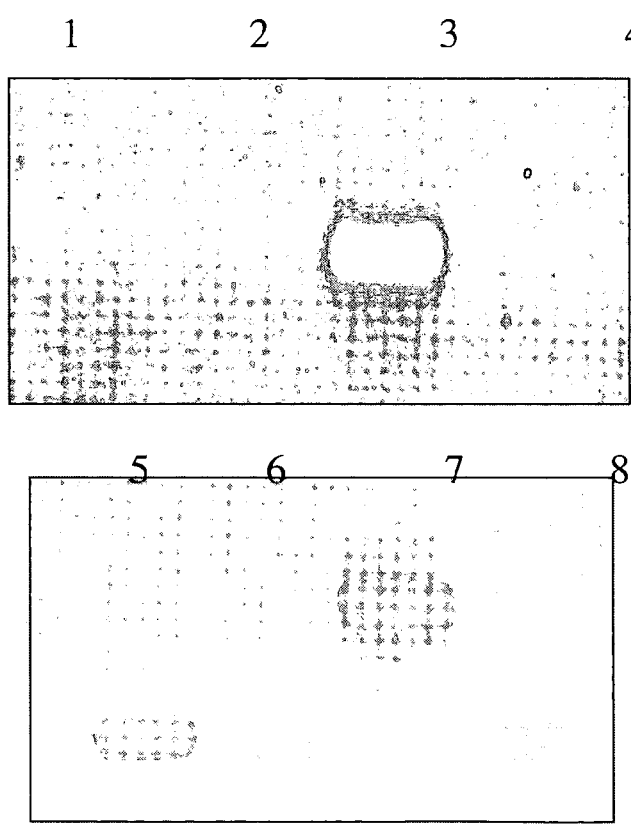
FIG. 14. E7 message is expressed in the thyroid and medullary thymic epithelial cells of the E6/E7 transgenic mouse. A. Tissue-specific expression of the E7 transgene is detected in the thyroid only but not the liver, spleen, or whole thymus. Lane 1: Liver; Lane 2: Spleen; Lane 3: Thyroid; Lane 4: Whole Thymus. B. Medullary thymic epithelial cells (mTECs) express E7. RT-PCR results are as shown for equivalent amounts of cDNA loaded for 40 cycles. Lane 5: Cathepsin S; Lane 6: E7; Lane 7: Actin; and Lane 8: Negative Control.

To determine whether or not E7 was expressed in the thymus, liver, spleen, thymus and thyroid were examined for the expression of the transgene in 6 to 8 week old mice. Abundant E7 message was found in the thyroid but not in other tissues (FIG. 14A). The absence of E7 message in whole thymus preparations was not indicative of lack of expression in the thymus, since the level of message of a peripherally expressed, organ-specific antigen, including thyroglobulin, has been shown to be too low to detect in whole thymocyte preparations (Derbinski, J., A. Schulte, B. Kyewski, and L. Klein. 2001. Promiscuous gene expression in medullary thymic epithelial cells mirrors the peripheral self. Nat Immunol 2:1032).

Tolerance to peripheral antigens in the thymus, including thyroglobulin, is mediated by the transient expression of these genes by the autoimmune regulator (AIRE) in thymic medullary epithelial cells (mTECs), with peak expression occurring prior to birth. AIRE is a transcription factor that maintains tolerance to self. To determine whether E7 expression in the transgenic mice followed the same pattern, mTECs from E6/E7 thymi of young mice (3-5 weeks) were examined for E7 expression.

The mTECs expressed E7 message, and also expressed Cathepsin S, which is known to be expressed in mTECs (FIG. 14B). Thus, E7 is expressed in the thymus of the transgenic mice, showing that these mice exhibit tolerance to the E7 antigen.

Example 9

Figure 15:
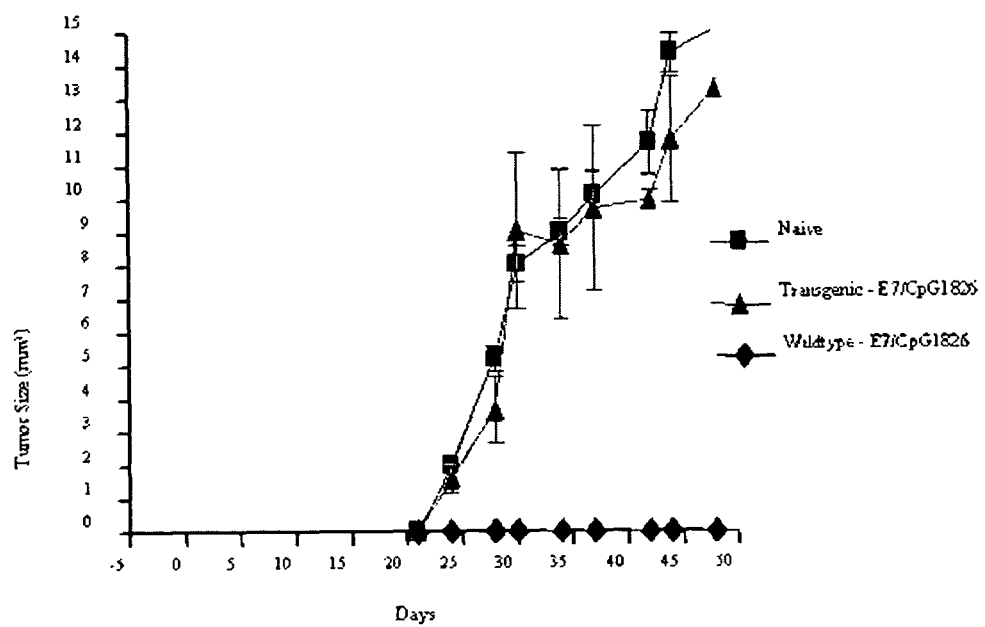
FIG. 15. RAHYNIVTF peptide plus CpG adjuvant does not protect against TC-1 challenge in E6/E7 transgenic mice. Two groups of transgenic mice received either E7 peptide plus adjuvant or PBS. A third group of wild type C57Bl/6 control mice received E7 peptide plus adjuvant. The mice were vaccinated twice intraperitoneally (i.p.), seven days apart and then challenged with 5×10$^4$ TC-1 cells seven days later. Tumors were measured every five days until it was necessary to sacrifice the unimmunized mice. Error bars represent standard deviations from the mean value.

Peptide-Based Vaccines do not Protect Against Tumor Challenge in E6/E7 Transgenic Mice As a measure of the impact of the self-expression of E7 on vaccine efficacy, E6/E7 transgenic mice were tested in a tumor protection experiment using an E7 peptide (RAHYNIVTF)-based vaccine, along with the immunostimulatory CpG sequence 1826 (Krieg, A M et al. 1995. CpG motifs in bacterial DNA trigger direct B-cell activation. Nature 374:546). While the peptide-based vaccine protected all the wild type mice from tumor challenge, it had no impact on tumor challenge in the transgenic mouse (FIG. 15). Thus, the E6/E7 mice exhibit reduced ability to reject tumor challenge, providing further evidence that they are tolerant to E7.

Example 10

Figure 16A:
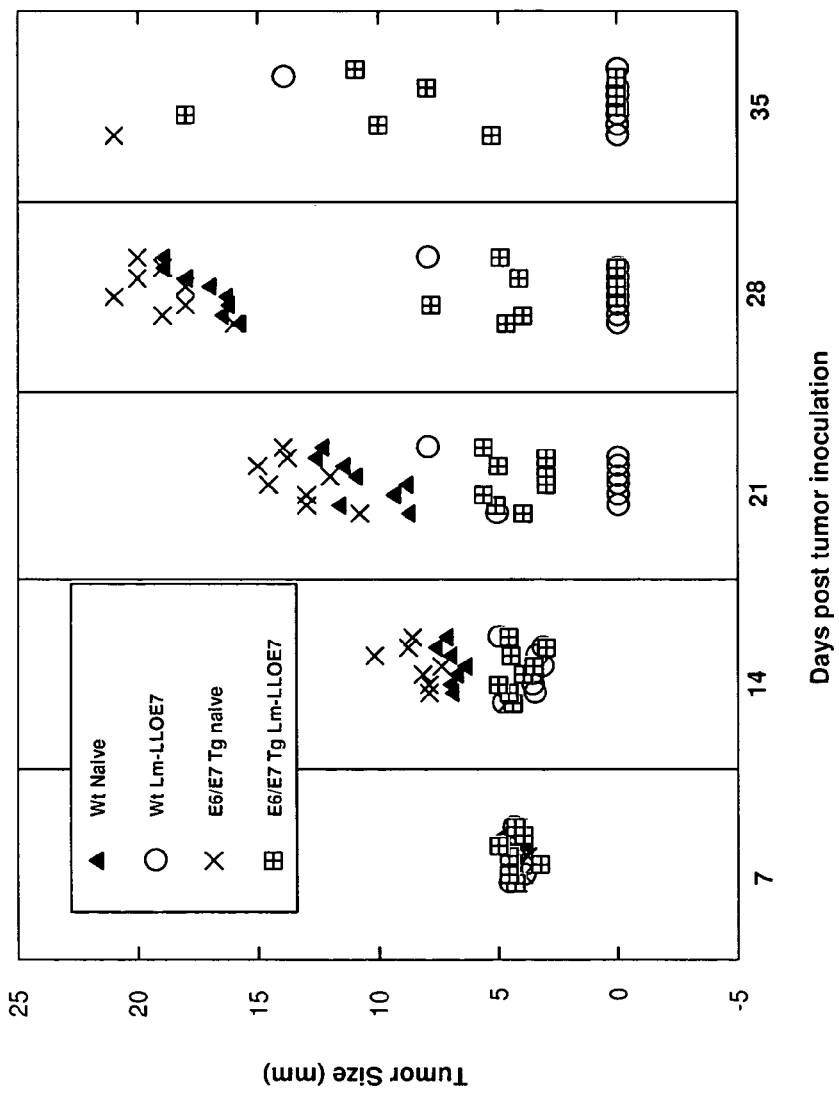
FIG. 16. Vaccines of the present invention induce regression of solid tumors in the E6/E7 transgenic mice in wild-type mice and transgenic mice immunized with LM-LLO-E7 (A), or LM-ActA-E7 (B), left naïve, or treated with LM-NP (control). Similar experiments were performed with 4 immunizations of LM-LLO-E7 (C), or LM-ActA-E7 (D).
Figure 16B:
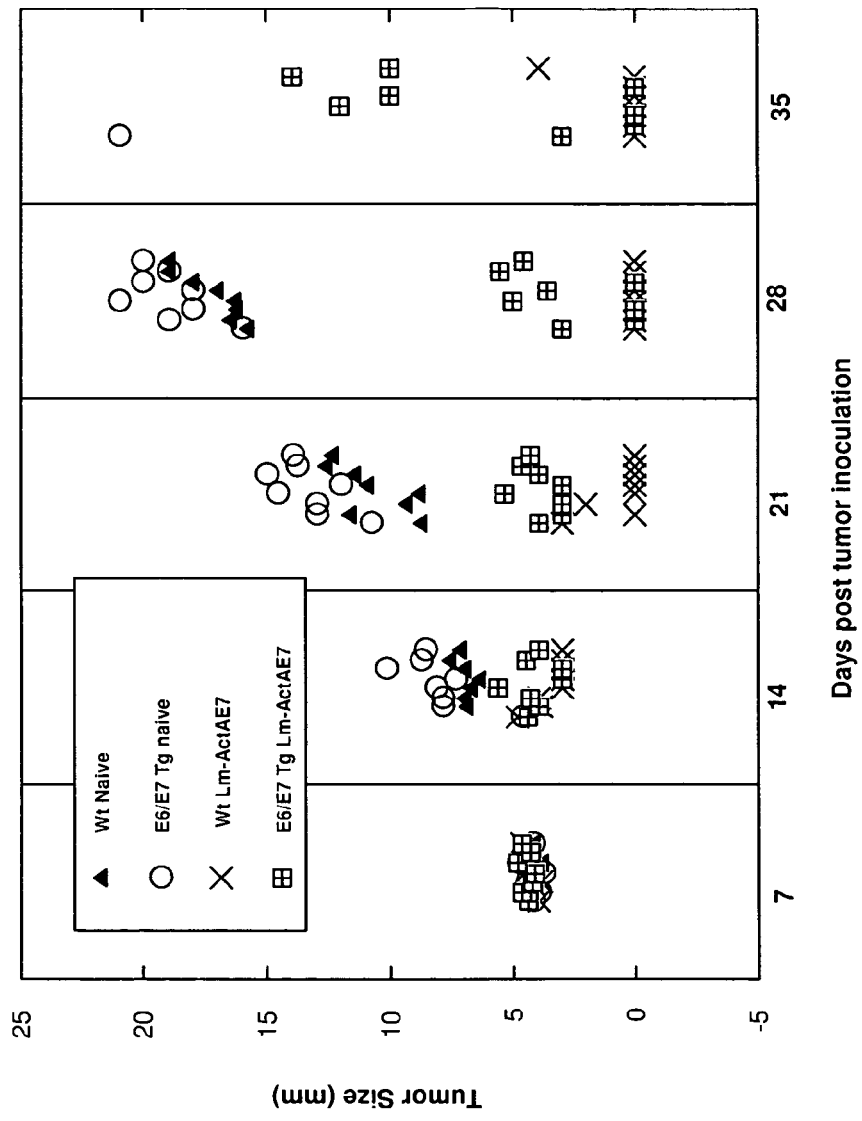
Figure 16C:
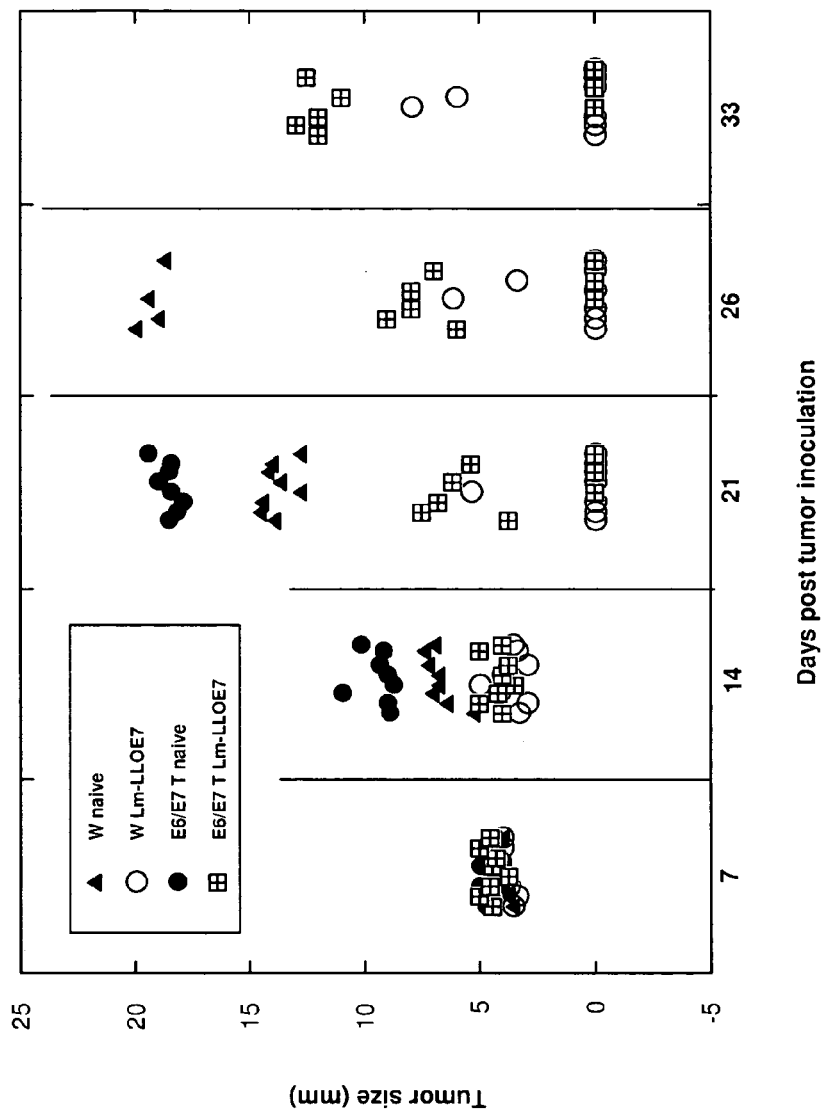
Figure 16D:
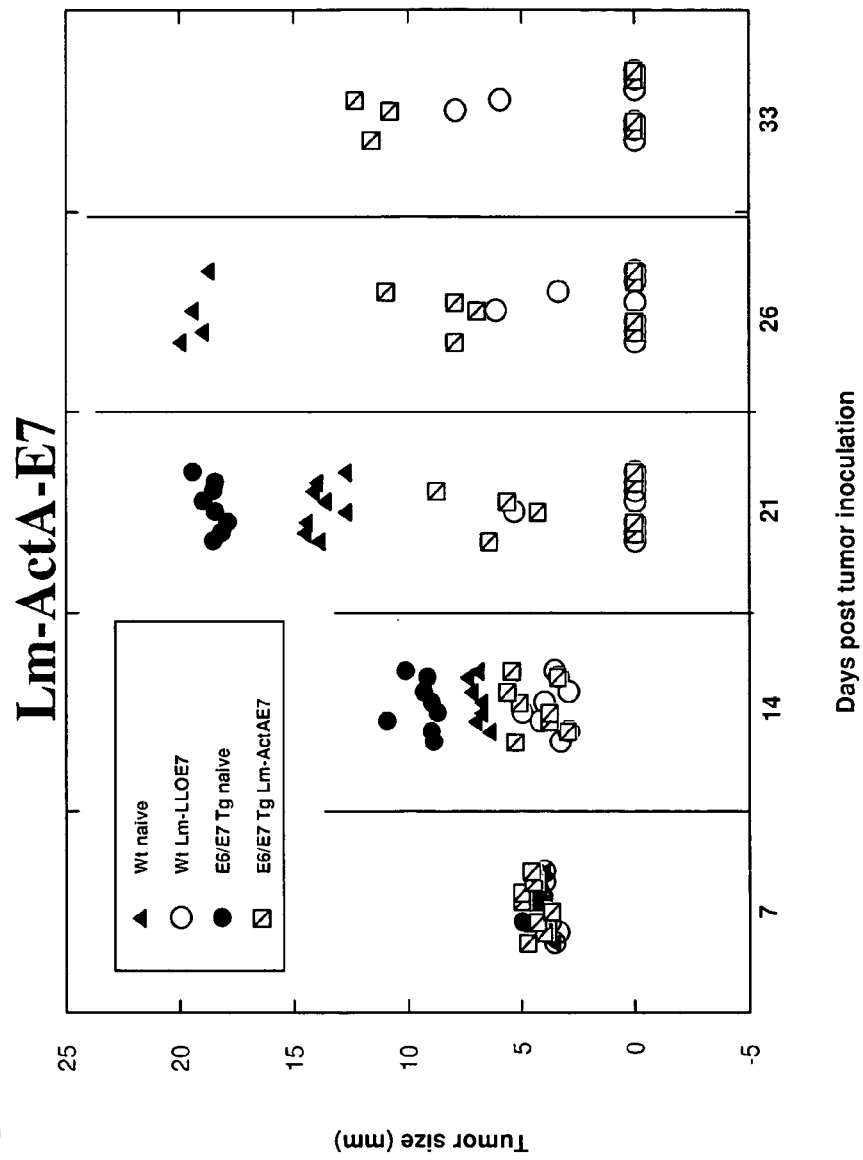

LLO and ActA Fusions Overcome Immune Tolerance of E6/E7 Transgenic Mice to E7-Expressing Tumors To examine the ability of vaccines of the present invention to overcome the immune tolerance of E6/E7 transgenic mice to E7-expressing tumors, $10^5$ TC-1 cells were implanted subcutaneously (s.c.) and allowed to form solid tumors in 6-8 week old wild-type and transgenic mice 7 and 14 days later, mice were left unimmunized or were immunized i.p. with LM-NP (control), 1×10⁸ cfu LM-LLO-E7 (FIG. 16A) or 2.5×10⁸ cfu LM-ActA-E7 (FIG. 16B). The naïve mice had a large tumor burden, as anticipated, and were sacrificed by day 28 or 35 due to tumors of over 2 cm. By contrast, by day 35, administration of either LM-LLO-E7 or LM-ActA-E7 resulted in complete tumor regression in 7/8 or 6/8, respectively, of the wild-type mice and 3/8 of the transgenic mice. In the transgenic mice that did not exhibit complete tumor regression, a marked slowing of tumor growth was observed in the LM-LLO-E7-vaccinated and LM-ActA-E7-vaccinated mice. In other experiments, additional vaccinations were administered on days 21 and 28. As before, LM-LLO-E7 (FIG. 16C) or LM-ActA-E7 (FIG. 16D) induced complete tumor regression in 4/8 and 3/8 transgenic mice, respectively, and slowing of tumor growth in the remaining mice.

The effectiveness of vaccines of the present invention in inducing complete tumor regression and/or slowing of tumor growth in transgenic mice was in marked contrast to the inefficacy of the peptide-based vaccine. Thus, vaccines of the present invention were able to overcome immune tolerance of E6/E7 transgenic mice to E7-expressing tumors.

Example 11

LLO-Her-2 Vaccination Halts and Reverses Growth of Her-2-Expressing Tumors; Fusion to LLO Induces Recognition of Sub-Dominant Epitopes Materials and Experimental Methods Subcloning pGG-55 (Example 1) was the backbone of the *Listeria* Her-2 constructs used in the Examples below.

Figure 17A:
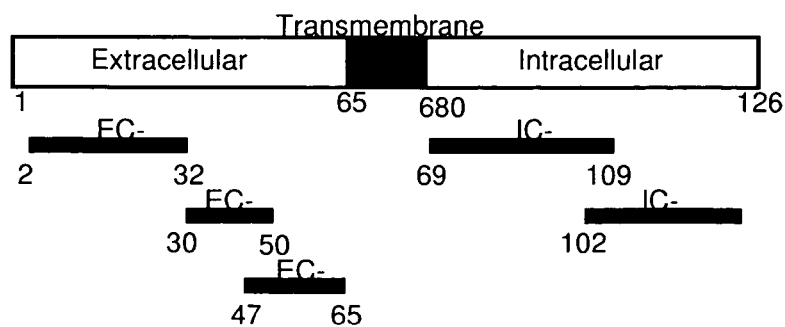
FIG. 17. Recombinant *Listeria monocytogenes* is capable of secreting each of Her-2 fragments as a ΔLLO-fusion protein. (A) Map of rat Her-2 fragments. (B) Western blot confirming secretion of fusion peptides. Marker (lane 1), Lm-ΔLLO-E7 (lane 2), Lm-ΔLLO-EC1 (lane 3), Lm-ΔLLO-EC2 (lane 4), Lm-ΔLLO-EC3 (lane 5), Lm-ΔLLO-IC1 (lane 6), and Lm-ΔLLO-IC2 (lane 7).

*L. monocytogenes* (LM) strains Lm-ΔLLO-EC1, Lm-ΔLLO-EC2, Lm-ΔLLO-EC3, Lm-ΔLLO-IC1, and Lm-ΔLLO-IC2 each contain a plasmid expressing a fragment of rat Her-2 fused to a fragment of the Listerial hly gene (hly encodes LLO). The following overlapping fragments of the extracellular and intracellular domains of Her-2 were cloned into the plasmid pGG-55: base pairs (bp) 74-994, (Lm-ΔLLO-EC1; corresponding to AA 20-326 of Her-2), 923-1519 (Lm-ΔLLO-EC2; corresponding to AA 303-501), 1451-1981 (Lm-ΔLLO-EC3; corresponding to AA 479-655), 2084-3259 (Lm-ΔLLO-IC1; corresponding to AA 690-1081), and 3073-3796 (Lm-ΔLLO-IC2; corresponding to AA 1020-1255). (FIG. 17A). The LD$_{50}$ of EC1, EC2, EC3, IC1, and IC2 were 1×10⁸, 1×10⁹, 5×10⁸, 1×10⁸, and 1×10⁸, respectively.

Each Her-2 fragment was amplified by PCR from the pNINA plasmid, which contains the full-length rat Her-2 gene, using the following primers. Restriction sites (XhoI in the case of EC1, IC1, and IC2 5' primers; SpeI for the 3' primers; and SalI for the EC2 and EC3 5' primers) are underlined, and the FLAG tag sequence in the EC2 and EC3 the 3' primers are indicated by italics:

EC1:
5' primer:
CACGCGGATGAAATCGATAAG<u>CTCGAG</u>CCCCCGGA (SEQ ID No:26)
ATCGCGGGCAC;

3' primer:
CCGG<u>ACTAGT</u>GACCTCTTGGTTATTCGGGGGACACA (SEQ ID No:27)
CC.

EC2:
5' primer:
CCGG<u>GTCGAC</u>TGCCCCTACAACTACCTGTCTACG; (SEQ ID No:28)

3' primer:
CCGG<u>ACTAGT</u>*TTACTTGTCATCGTCGTCCTTGTAGT* (SEQ ID No:29)
CCCCACTGTGGAGCAGGGCCTG;

EC3:
5' primer:
CCGG<u>GTCGAC</u>TGCTTTGTACACACTGTACCTTGG; (SEQ ID No:30)

3' primer:
CCGG<u>ACTAGT</u>*TTACTTGTCATCGTCGTCCTTGTAGT* (SEQ ID No:31)
CCGGGCTGGCTCTCTGCTCTGC;

IC1:
5' primer:
CCGG<u>CTCGAG</u>TATACGATGCGTAGGCTGCTGCAGG; (SEQ ID No:32)

3' primer:
CCGG<u>ACTAGT</u>AGCCAGTGGAGATCTGGGGGCCC; (SEQ ID No:33)

IC2:
5' primer:
CCGG<u>CTCGAG</u>GGTGACCTGGTAGACGCTGAAG (SEQ ID No:34)
and

3' primer:
CCGG<u>ACTAGT</u>TACAGGTACATCCAGGCCTAGG. (SEQ ID No:35)

Fragments were amplified by PCR and cloned into the pCR 2.1 expression system (Invitrogen, Carlsbad, Calif.), then excised with the delineated enzymes. The E7 gene was excised from the pGG-55 plasmid using Xho I and Spe I, then the Her-2 fragment was fusion was ligated into the E7 site (ends digested with Sal I are compatible with XhoI ends). XFL-7, aprfA negative strain of LM, (Gunn G R et al, J Immunol 167: 647, 2001) was transfected with the plasmids by electroporation.

Bacteria

Bacteria were grown in brain heart infusion medium (BD, Sparks, Md.) with 50 μg/ml chloramphenicol and were frozen in 1 ml aliquots at −80° C.

Western Blots

ΔLLO-Her-2 expressing strains were grown overnight at 37° C. in Luria-Bertani (LB) medium with 50 microgram per milliliter (μg/ml) chloramphenicol. Supernatants were TCA precipitated and resuspended in 1×LDS sample buffer (Invitrogen, San Diego, Calif.). 15 microliter (μl) of each sample was loaded on a 4-12% Bis-Tris SDS-PAGE gel (Invitrogen, San Diego, Calif.). Gels were transferred to a Immobilon-P polyvinylidene fluoride membrane (Millipore, Billerica, Mass.) and blotted with a polyclonal rabbit serum recognizing residues 1-30 of LLO, followed by HRP-conjugated anti-rabbit antibody (Amersham Pharmacia Biotech, UK).

Statistical Analyses

Statistical analyses were performed using Student's t-test throughout the Examples below, unless indicated otherwise.

Mice

Six to eight week old female FVB/N mice were purchased from Charles River Laboratories (Wilmington, Mass.).

Cell Lines

The FVB/N syngeneic NT-2 tumor cell line, derived from a spontaneously occurring mammary tumor in an FVB/N Her-2 transgenic mouse (Reilly R T et al, Canc Res 60: 3569, 2000), constitutively expresses low levels of rat Her-2 and is tumorigenic in wild type syngeneic mice. NT-2 cells were grown in RPMI 1640 medium with 20% FCS, 10.2 mM HEPES, 2 millimolar (mM) L-glutamine, 100 micromolar (μM) nonessential amino acids, 1 mM sodium pyruvate, 50 U (units)/ml penicillin G, 50 µg/ml streptomycin, 20 µg/ml insulin, and 2 µg/ml gentamycin at 37° C. with 5% $CO_2$.

Experimental Setup 6-8 week-old FVB/N mice (n=8) were injected subcutaneously in the right flank with $2\times10^6$ NT-2 tumor cells in 200 µl PBS. Seven days post-tumor inoculation, palpable tumors of 4-5 mm were observed, after which mice were injected intraperitoneally with recombinant LM or PBS on days 7, 14, and 21. The shortest and longest surface diameters of the tumors were measured every 2 days with calipers. Mice were sacrificed if they reached a point at which mean tumor diameter reached 20 mm.

Results

Figure 17B:
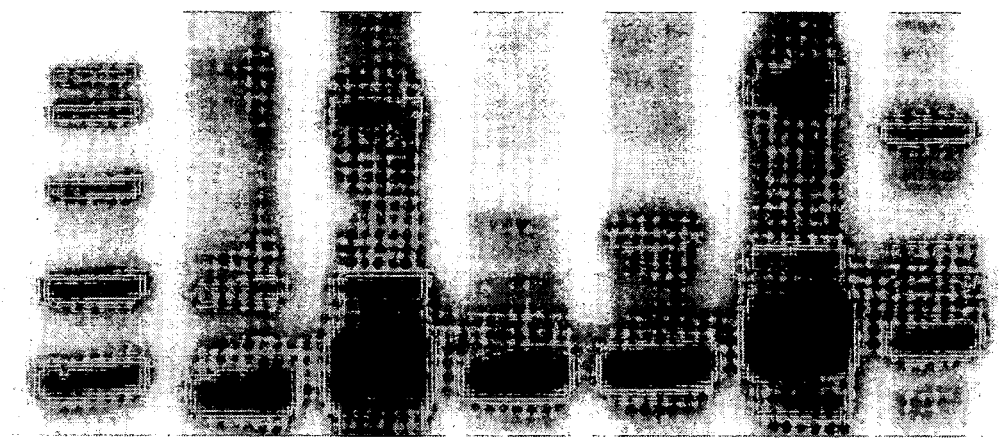

Five recombinant LM strains were constructed that express and secrete overlapping fragments of the rat Her-2 gene fused to the N-terminal portion of L. monocytogenes LLO protein. The signal sequence and transmembrane domain of Her-2 were not included among the fragments. Secretion of each Her-2 fragment was confirmed by Western blot (FIG. 17B). Molecular weights of the proteins Lm-ΔLLO-EC1, Lm-ΔLLO-EC2, Lm-ΔLLO-EC3, Lm-ΔLLO-IC1, and Lm-ΔLLO-IC2 were 83, 70, 68, 92.5, and 74-kDa (kilodalton), respectively. The strains were attenuated relative to the wild-type 10403S strain, exhibiting virulences comparable to Lm-ΔLLO-E7; namely $1\times10^8$, $5\times10^8$, $1\times10^9$, $1\times10^8$, and $1\times10^8$ colony forming units (CFU), respectively.

Figure 18:
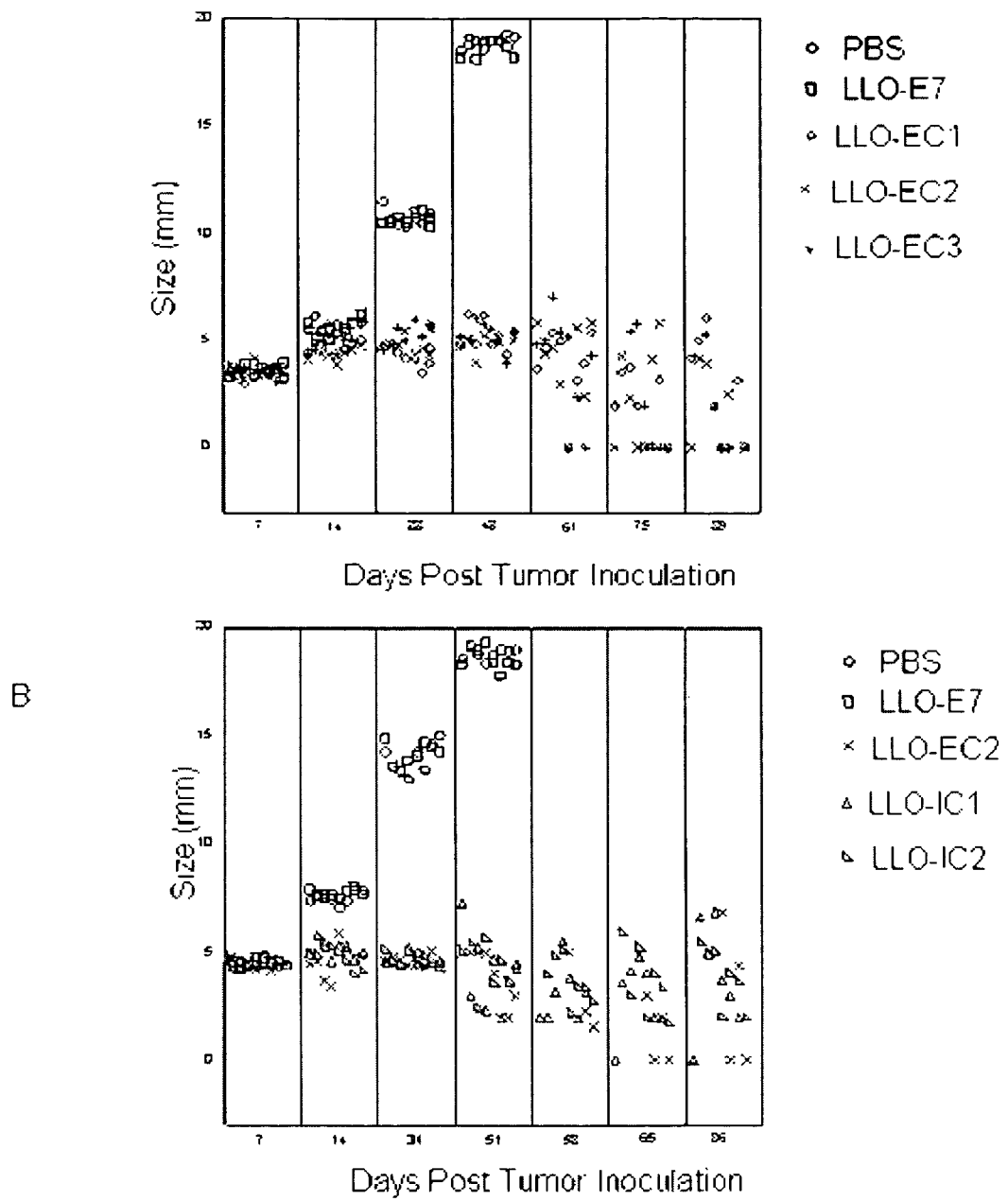
FIG. 18. Lm-ΔLLO-Her-2 vaccines each induce a halt in tumor growth of established NT-2 tumors in wild-type FVB mice. Each data point represents the average of shortest and longest surface tumor diameter of one mouse at a given time point. Mice were sacrificed when the average tumor diameter reached 2.0 cm; tumor measurements are only shown for the surviving mice at a given time point. Representative results of 2 experiments are depicted. (A) Lm-ΔLLO-EC1, Lm-ΔLLO-EC2, and Lm-ΔLLO-EC3; (B) Lm-ΔLLO-IC1, and Lm-ΔLLO-IC2.

LM strains expressing ΔLLO-Her-2 fusions were compared to PBS and Lm-ΔLLO-E7 (negative controls) for their ability to induce immunity against and reduction of tumors composed of the rat Her-2 expressing tumor line, NT-2. FVB/N mice were injected with NT-2 tumors, then, on days 7, 14, and 21 following tumor inoculation, were administered 0.1 $LD_{50}$ of recombinant LM or PBS. Injection of LM expressing the ΔLLO-Her-2 fusions halted tumor growth after the first injection (FIGS. 18A-B); the cessation in tumor growth continued through the last timepoint, more than nine weeks after the last Her-2 vaccination. Moreover, a complete regression of tumors was subsequently observed in 3/8 of the Lm-ΔLLO-EC2 and Lm-ΔLLO-EC3 mice and 1/8 of the Lm-ΔLLO-EC1 and Lm-ΔLLO-IC1 mice. Additional mice from all five of the ΔLLO-Her-2 groups exhibited a reduction in tumor size. As expected, tumors grew continually in mice injected with PBS and Lm-ΔLLO-E7.

In addition, elicitation of a response to each of the 5 segments of Her-2 show that fusion of an antigen to LLO imparts to the resulting vaccine the ability to induce immunity against subdominant T cell epitopes of the antigen.

These findings demonstrate that LLO-Her-2 fusions are capable of eliciting immunity against Her-2-expressing tumors, and that the elicited immunity (a) is strong enough to induces the regression and/or complete cessation of growth of greater than 75% of established Her-2-expressing tumors; and (b) lasts over the course of over at least several months.

Thus, vaccines of the present invention are efficacious for induction of regression of tumors and inhibition of tumor growth with a variety of antigens (E7, OVA, NP, and Her-2), showing that findings of the present invention are generalizable to all antigens. In addition, a number of different PEST-like sequences can be used (either LLO or ActA), showing that findings of the present invention are generalizable to all PEST-like sequences. Moreover, tumor protection was demonstrated in a variety of tumor types, showing that that findings of the present invention are generalizable to all tumor types.

Example 12

Immune Responses Induced by Lm-LLO-Her-2 Include $CD8^+$ T Cells

Materials and Experimental Methods $CD8^+$ T Cell Depletion $CD8^+$ T cells were depleted by injection with 0.5 mg of the anti-CD8 antibody 2.43 (Sarmiento M et al, J Immunol 125 (6): 2665-72, 1980) on days 6, 7, 8, 11, 14, 17, 20, and 23 post-tumor injection. $CD8^+$ T cell populations were reduced by greater than 95%, as measured by flow cytometric analysis on day 24.

Flow Cytometric Analysis

Three color flow cytometry for CD8 (53-6.7, FITC conjugated), CD62 ligand (Mel-14, APC conjugated) (BD Biosciences Pharmingen, San Diego, Calif.), and Her-2H-$2^q$ tetramer (PE conjugated) was performed using a FACSCalibur flow cytometer with CellQuest software (Becton Dickinson, San Jose, Calif.). Tetramers, provided by the NIAID Tetramer Core Facility of Emory University and the NIH AIDS Research and Reference Reagent Program, were loaded with an H-2q specific PDSLRDLSVF peptide. Splenocytes were stained at room temperature (rt) with the tetramer for one hour (hr) at 1:200 dilution, then at 4° C. with anti-CD8 and anti-CD62L antibodies for 30 minutes (min). The $CD8^+$, $CD62L^{low}$ subset was selected ("gated on"), and percentages of tetramer$^+$ cells were compared using FlowJo software (Tree Star, Inc, Ashland, Oreg.).

Results

Figure 19:
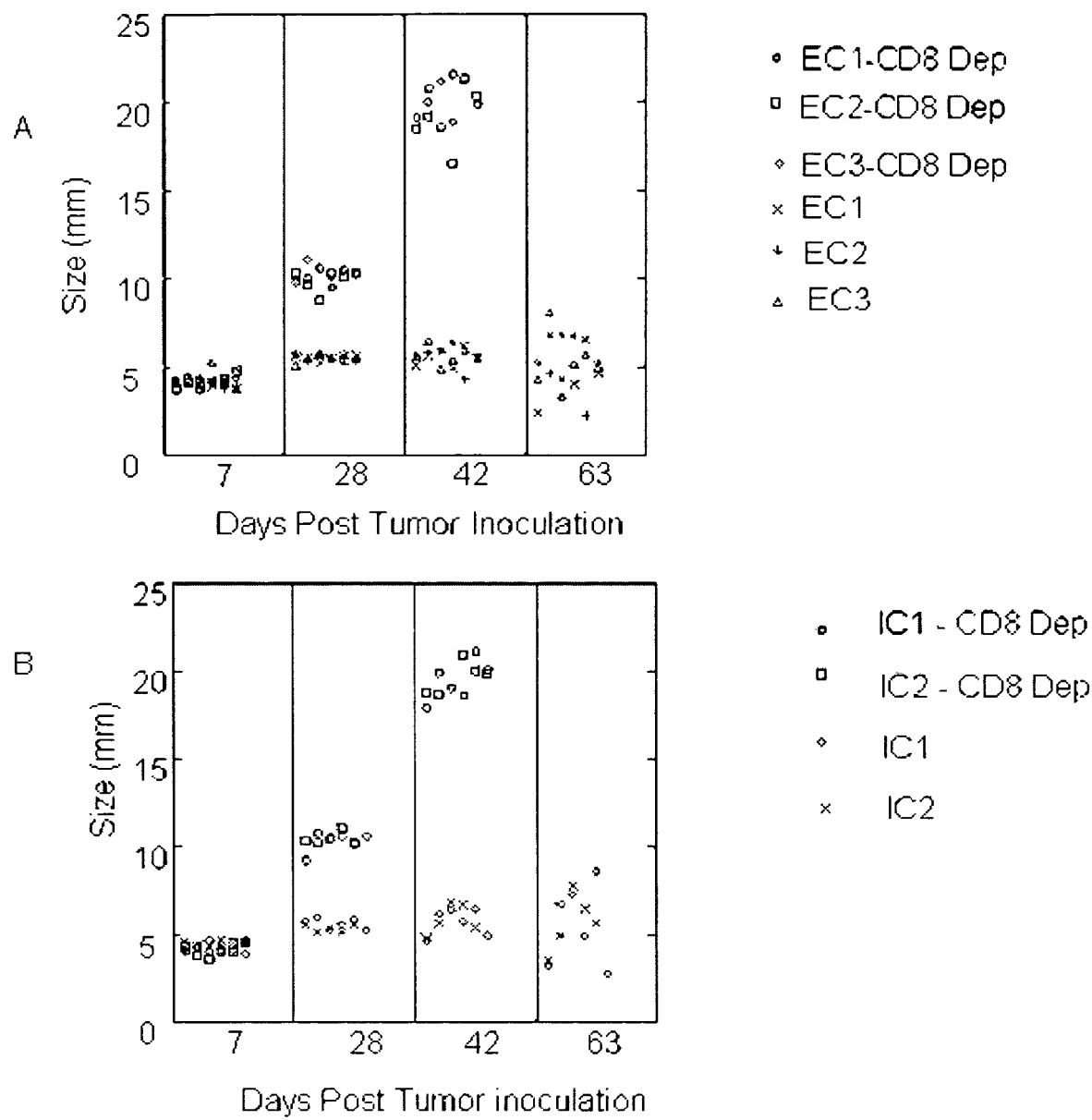
FIG. 19. CD8+ T cells participate in Lm-LLO-Her-2 induced tumor stasis. Tumor measurements are shown only for the surviving mice at a given time point. (A) Lm-ΔLLO-EC1, Lm-ΔLLO-EC2, and Lm-ΔLLO-EC3 both depleted and not depleted for CD8+ T cells. (B) Lm-ΔLLO-IC1 and Lm-ΔLLO-IC2 both depleted and not depleted for CD8+ T cells.

To determine the type of T cells that were mediating the observed anti-Her-2 immune responses, FVB/N mice with NT-2 tumors were depleted of $CD8^+$ T cells, beginning 1 day prior to vaccination with Lm-ΔLLO-Her-2 vaccines, then vaccinated as described in Example 11. In the anti-$CD8^+$-injected mice, each of the Lm-ΔLLO-Her-2 vaccines lost effectiveness (FIG. 19A-B); while in the non-depleted mice, tumor growth was controlled, as observed in Example 11.

Figure 20:
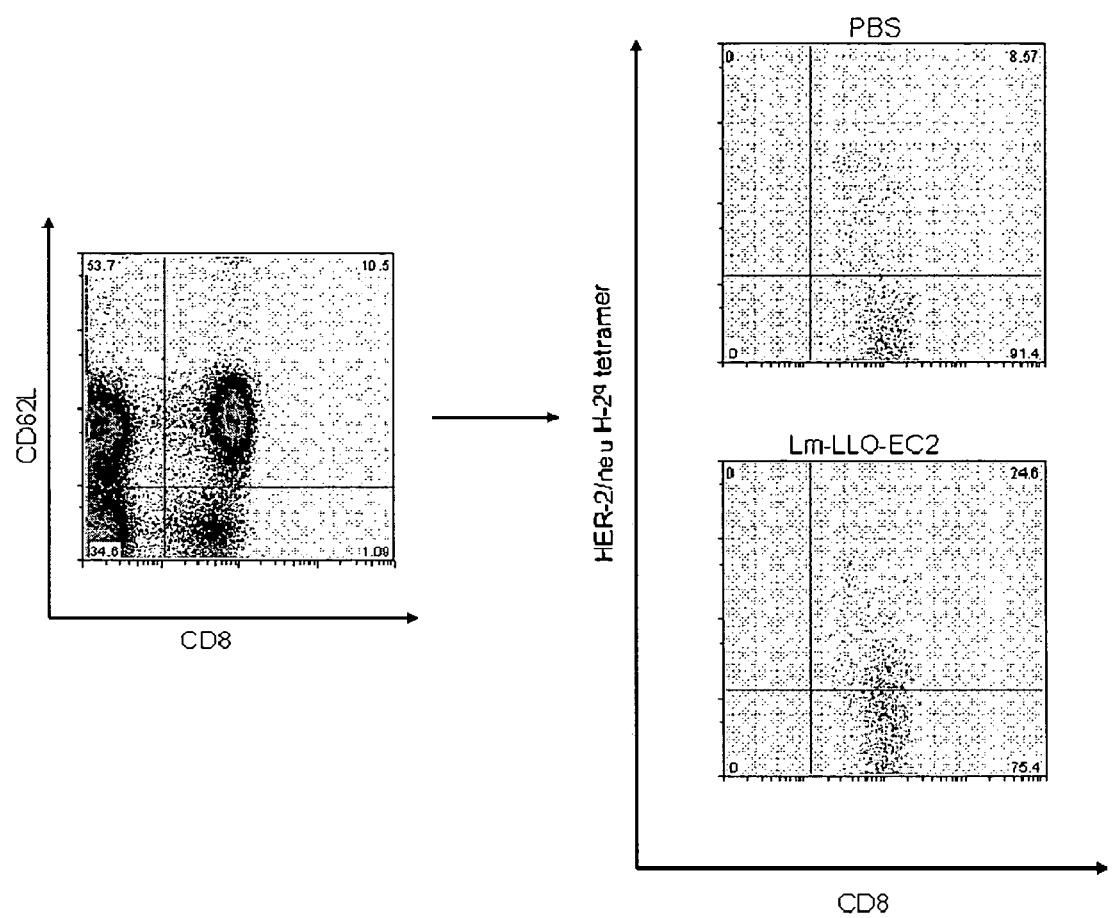
FIG. 20. Lm-ΔLLO-EC2 induces a 3-fold increase in tetramer+, CD8+ T cells. FVB/N mice were immunized with Lm-ΔLLO-EC2 or PBS. Subsequently, splenocytes were stained with an H-2$^q$ Her-2 tetramer, anti-CD8, and anti-CD62L.

Tetramer analysis was next used to confirm the above results. Non-tumor bearing, 6-8 week-old FVB/N mice were immunized with either PBS or 0.1 $LD_{50}$ Lm-ΔLLO-EC2 and boosted 21 days later. Splenocytes were harvested 5 days after the boost and were stained with an H-$2^q$ tetramer specific for the epitope defined by AA 420-429 (PDSLRDLVF; SEQ ID No: 36). A 3-fold increase in tetramer positive cells was observed in the Lm-ΔLLO-EC2-vaccinated mice (FIG. 20).

These results show that $CD8^+$ T cells are featured in the immunity elicited by fusion vaccines of the present invention.

Example 13

Fusion to LLO Enhances Immunogenicity of Her-2 Independently of LM

Materials and Experimental Methods

DNA Vaccines

DNA vaccines were constructed using pcDNA 3.1. Her-2 and the EC1 fragment were amplified by PCR using the following primers:
Full length, unfused Her-2: 5' CCGG<u>GCTAGC</u>ATGGTCATCATGGAGCTGGCCGG (Nhe I site underlined; SEQ ID No: 37) and 3' CCGG<u>GATATC</u>TTACTTGTCATCGTCGTCCTTGTAGTCTCAT- ACAGGTACATCCAGGCC (EcoRV site underlined, FLAG tag in italics, stop codon in bold; SEQ ID No: 38). The above 5' primer was also used for amplifying unfused EC1, and the 3' primer for amplifying ΔLLO—full length Her-2.

ΔLLO-full length Her-2: 5' CCGG GTCGACATGGTCATCATGGAGCTGGCCGG (Sal I site underlined; SEQ ID No: 39). This primer was also used for amplifying ΔLLO-EC 1.

Unfused EC1: 3' CCGGGATATCTTACTT- GTCATCGTCGTCCTTGTAGTCTCAGAC- CTCTTGGTTATTCGGG GG (EcoRV site underlined, FLAG tag in italics, stop codon in bold; SEQ ID No: 40). This primer was also used for amplifying unfused EC1 fused to ΔLLO.

Fragments were cloned into the multicloning site of pcDNA3.1, and used to transform *Escherichia coli*. Bacteria were grown in Luria-Bertani media (BD, Sparks, Md.) with 50 micrograms per milliliter (μg/ml) ampicillin.

Tumor Regression Experiments

Tumor regression experiments were performed as described in Example 11, except that $7 \times 10^5$ NT-2 cells were utilized, and vaccinations were administered on days 3, 10, and 18. DNA vaccines (50 μg each of the recombinant pcDNA plasmid+the GM-CSF plasmid; or GM-CSF alone) were administered intra-muscularly and Lm administered intraperitoneally.

Results

Several factors were present in the Lm-ΔLLO-Her-2 vaccines that may have contributed to the enhancement of immunity and recognition of sub-dominant epitopes: (a) delivery by LM; (b) fusion of the target antigen to ΔLLO; (c) breaking Her-2 into fragments. To determine which 1 or more of these factors contributed to these effects, mice were vaccinated with the following DNA vaccines (a) pcDNA 3.1-full length Her-2 ("pcDNA neu"); (b) pcDNA 3.1 ΔLLO-full length Her-2 (pcDNA LLO-neu); (c) pcDNA 3.1-EC1 (pcDNA EC1); (d) pcDNA 3.1-ΔLLO-EC1 (pcDNA LLO-EC1); or (e) Lm-ΔLLO-EC1, and a tumor regression experiment was performed. GM-CSF was included with the DNA vaccines because of its ability to enhance the efficacy of DNA vaccines (McKay P F, Barouch D H et al, Eur J Immunol 2004 April; 34(4): 1011-20.).

Figure 21A:
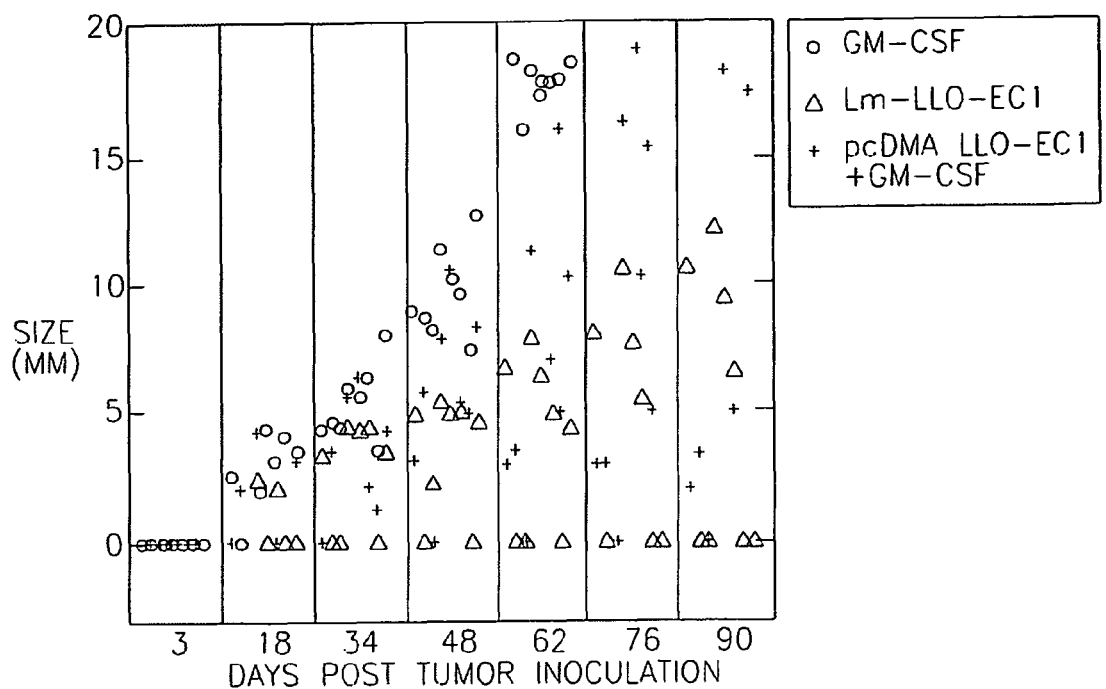
FIG. 21. Delivery by LM and fusion to ΔLLO increases the anti-tumor immune response of Her-2 vaccines using DNA plasmids for delivery. Average tumor diameter for each mouse is depicted. Tumor measurements are shown only for the surviving mice at a given time point. (A) Lm-ΔLLO-EC1 vs. pcDNA ΔLLO-EC1+GM-CSF, (B) pcDNA EC1+GM-CSF vs. pcDNA ΔLLO-EC1+GM-CSF, (C) pcDNA neu+ GM-CSF vs. pcDNA ΔLLO-neu+GM-CSF, (D) pcDNA ΔLLO-neu+GM-CSF vs. pcDNA ΔLLO-EC1+GM-CSF, and (E) pcDNA neu+GM-CSF vs. pcDNA EC1+GM-CSF.
Figure 21B:
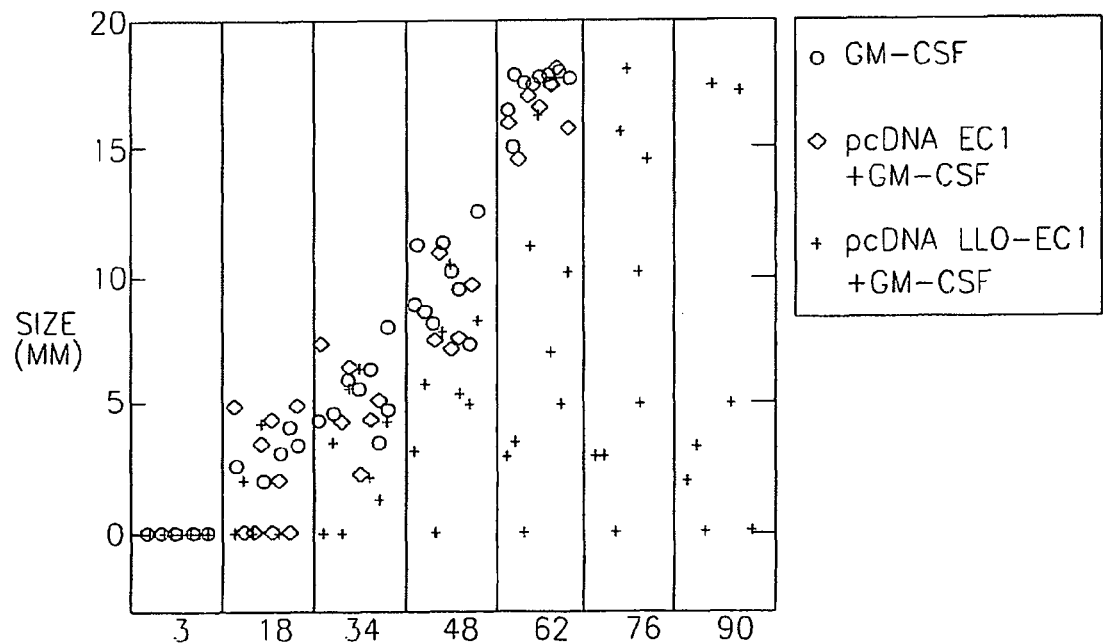
Figure 21C:
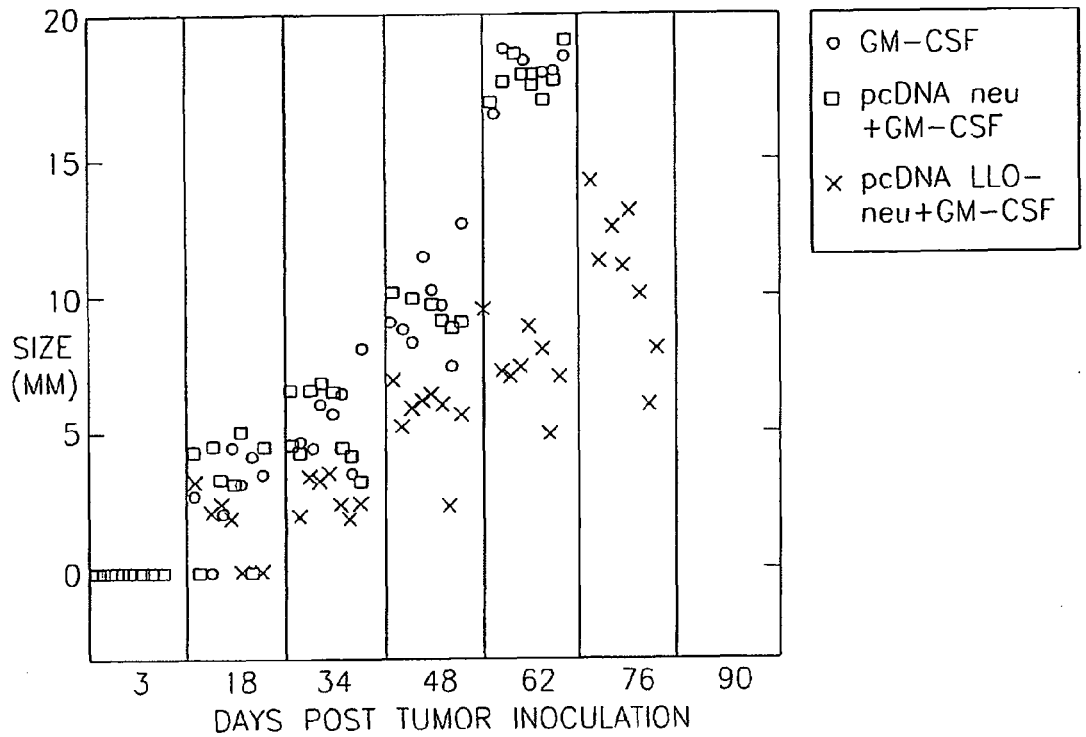
Figure 21D:
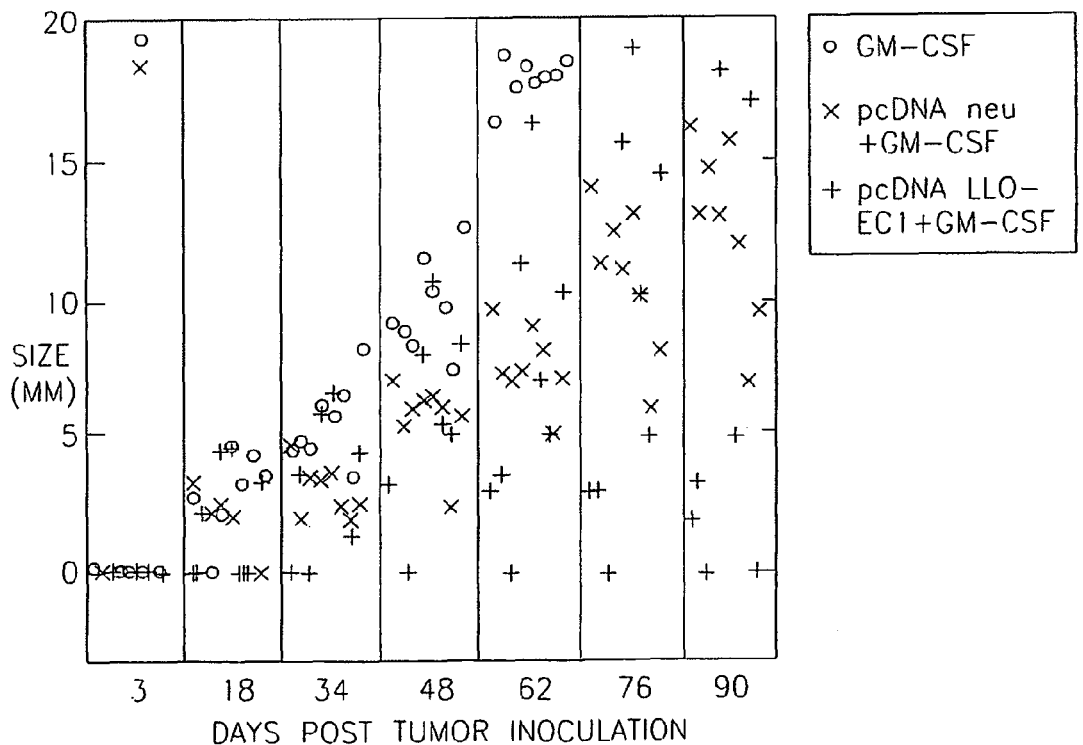
Figure 21E:
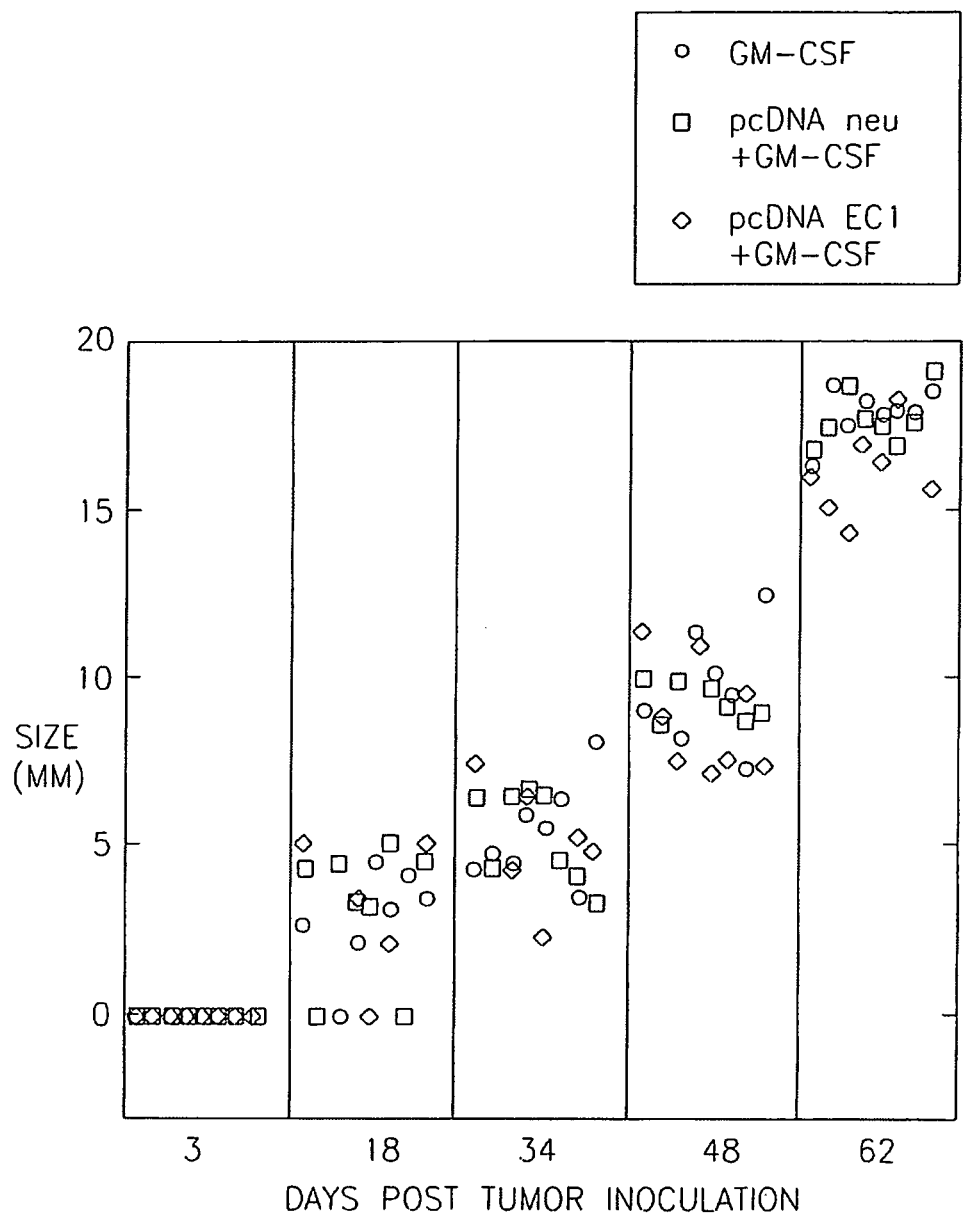

Fusion to ΔLLO enhanced immunogenicity of EC1, as seen by comparison of pcDNA EC1 vs. pcDNA ΔLLO-EC1 and pcDNA neu vs. pcDNA ΔLLO-neu (FIG. 21B-C); vaccines containing unfused antigen did not control tumor growth significantly more than the negative control (FIGS. 21A and E). In addition, effective tumor growth was observed with Lm-ΔLLO-EC1. In the case of pcDNA ΔLLO-EC1, 1 mouse never developed a tumor, and tumor growth was retarded in several other mice. Dividing Her-2 into smaller fragments also enhanced immunogencity, as seen from a comparison of pcDNA ΔLLO-neu vs. pcDNA ΔLLO-EC1, in which the latter group exhibited superior tumor control (FIG. 21D).

In separate experiments, fusion to ΔLLO enhanced immunogenicity of E7 in the context of a DNA vaccine. Thus, fusion to ΔLLO enhances the immunogenicity of antigens in the context of a DNA vaccine.

In separate experiments, administration of a plasmid encoding ΔLLO enhanced immunogenicity of antigen encoded on a separate plasmid.

Example 14

LLO-Her-2 Overcomes Immune Tolerance to a Self Antigen

Materials and Experimental Methods

Rat Her-2/neu transgenic mice were purchased form Jackson laboratories and bred in the University of Pennsylvania vivarium. Young, virgin HER-2/neu transgenic mice that had not spontaneously developed tumors were injected with $5 \times 10^4$ NT-2 cells. Because the transgenic mouse is profoundly tolerant to HER-2/neu, the minimum dose required for tumor growth in 100% of animals is much lower than wild-type mice (Reilly R T, Gottlieb M B et al, Cancer Res. 2000 Jul. 1; 60(13): 3569-76). NT-2 cells were injected into the subcutaneous space of the flank. Mice received 0.1 $LD_{50}$ of the *Listeria* vaccine on day 7 after tumor implantation (the time when 4-5 mm palpable tumors were detected) and weekly thereafter, for an additional 4 weeks.

Results

The rat Her-2/neu gene differs from the mouse neu by 5-6% of AA residues, and thus is immunogenic in the mouse (Nagata Y, Furugen R et al, J Immunol. 159: 1336-43). A transgenic mouse that over-expresses rat Her-2/neu under the transcriptional control of the Mouse Mammary Tumor Virus (MMTV) promoter and enhancer is immunologically tolerant to rat Her-2/neu. These mice spontaneously develop breast cancer. The MMTV promoter also operates in hematopoietic cells, rendering the mice profoundly tolerant to HER-2/neu. This, this mouse is a stringent model for human breast cancer and in general for tumors expressing antigens, such as Her-2/neu, that are expressed at low levels in normal tissue (Muller W. J. (1991) Expression of activated oncogenes in the murine mammary gland: transgenic models for human breast cancer. Canc Metastasis Rev 10: 217-27).

Figure 22:
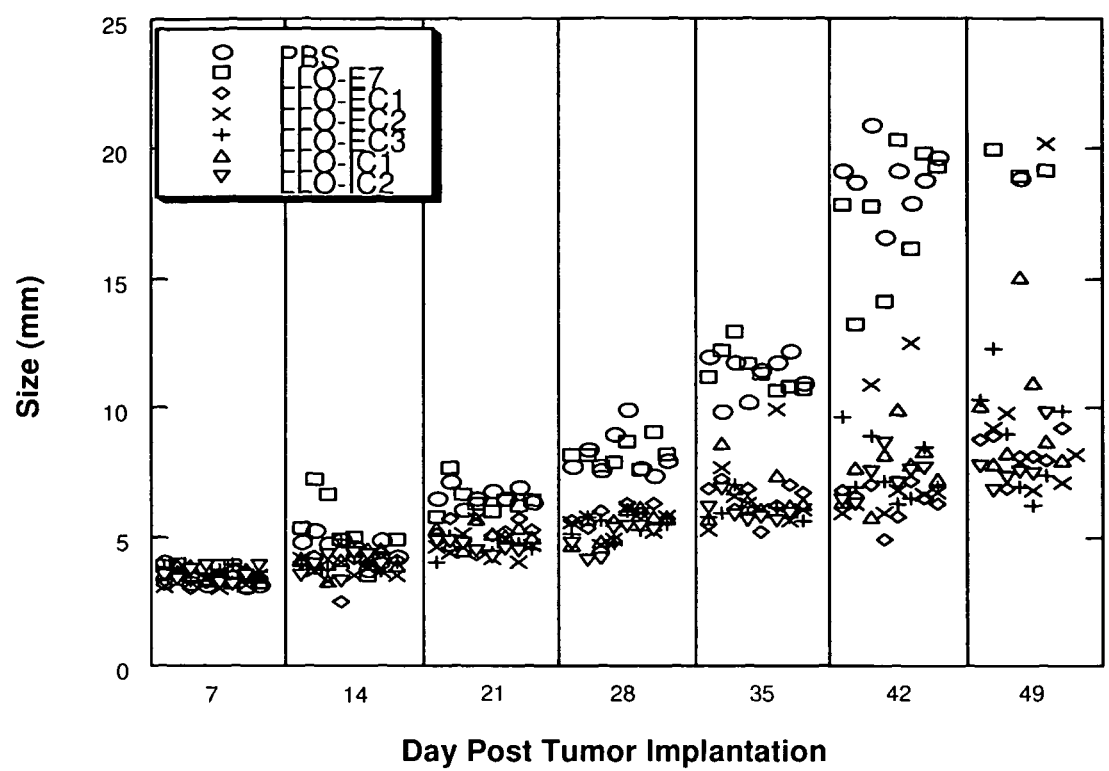
FIG. 22. Lm-ΔLLO-Her-2 vaccines slow the growth of established rat Her-2 expressing tumors in rat Her-2/neu transgenic mice, in which rat Her-2 is expressed as a self-antigen.

6-8 week-old HER-2/neu transgenic mice were injected with NT-2 cells, then immunized with each of the LM-ΔLLO-Her-2 vaccines, or with PBS or ΔLLO-E7 (negative controls). While most control mice had to be sacrificed by day 42 because of their tumor burden, tumor growth was controlled in all of the vaccinated mice (FIG. 22).

Thus, the ΔLM-LLO-Her-2 vaccines are able to break tolerance to self antigen expressed on a tumor cell, as evidenced by their ability to induce the regression of established NT-2 tumors. Accordingly, vaccines comprising LLO-antigen and ActA-antigen fusions are efficacious for breaking tolerance to self antigen with either Her-2 or E7, showing that findings of the present invention are generalizable to all antigens.

Example 15

LLO-Her-2 Vaccines Control Spontaneous Tumor Growth in Her-2/Neu Transgenic Mice Materials and Experimental Methods ΔLM-LLO-Her-2 vaccines were administered in the following amounts (cfu): Lm-LLO-EC1: $1 \times 10^7$; Lm-Lm-LLO-EC2: $5 \times 10^7$; LLO-EC3: $1 \times 10^8$; Lm-LLO-IC2: $1 \times 10^7$; Lm-LLO-IC1: $1 \times 10^7$.

Results

Figure 23:
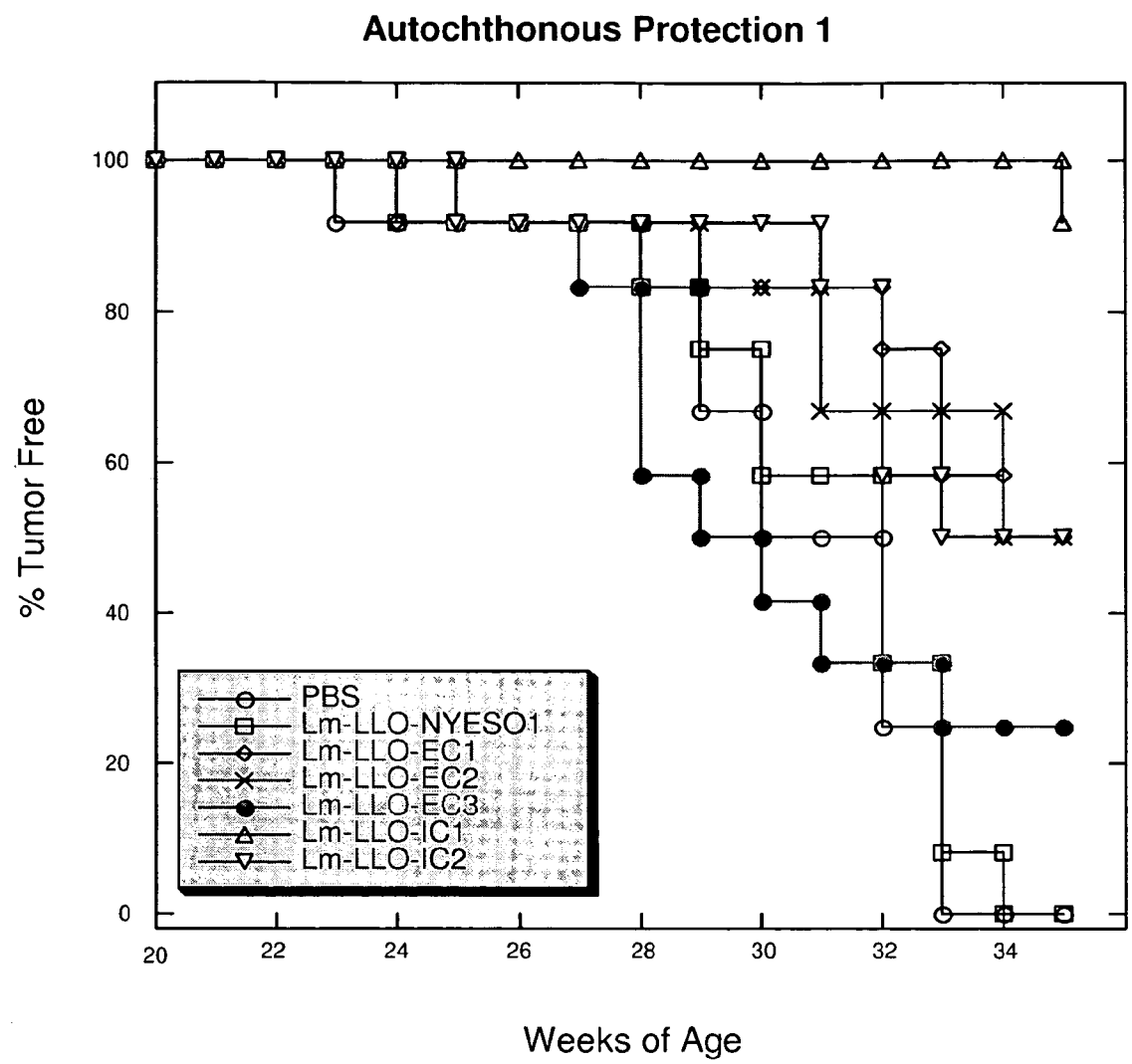
FIG. 23. LLO-Her-2 vaccines control spontaneous tumor growth in Her-2/neu transgenic mice.

ΔLM-LLO-Her-2 vaccines were also evaluated for ability to prevent spontaneous tumor growth in the Her-2/neu transgenic mice. The transgenic mice (n=12 per vaccine group) were immunized 5 times with 0.1 $LD_{50}$ of one of the vaccine strains, beginning at age 6 weeks and continuing once every three weeks. Mice were monitored for tumor formation in the mammary glands. By week 35, all of the control mice (PBS or Lm-LLO-NY-ESO-1-immunized) had developed tumors. By contrast, 92% of the Lm-LLO-IC1 group were tumor free, as were 50% of the mice Lm-LLO-EC2, Lm-LLO-EC1, and Lm-LLO-IC2, and 25% of the mice immunized with Lm-LLO-EC3 (FIG. 23).

These findings confirm the results of the previous Examples, showing that vaccines of the present invention are able to break tolerance to self antigens and prevent spontaneous tumor growth.

Example 16

LLO and ActA Fusions Reduce Autochthonous (Spontaneous) Tumors in E6/E7 Transgenic Mice To determine the impact of the Lm-LLO-E7 and Lm-ActA-E7 vaccines on autochthonous tumors in the E6/E7 transgenic mouse, 6 to 8 week old mice were immunized with $1 \times 10^8$ Lm-LLO-E7 or $2.5 \times 10^8$ Lm-ActA-E7 once per month for 8 months. Mice were sacrificed 20 days after the last immunization and their thyroids removed and weighed. The average weight of the thyroids in the vaccinated groups was significantly less than the unvaccinated or mock vaccinated groups (Table 1), showing that the Lm-LLO-E7 and Lm-ActA-E7 vaccines controlled spontaneous tumor growth.

TABLE 1

Thyroid weight (mg) in unvaccinated and vaccinated transgenic mice at 8 months of age.

| Untreated | ±S.D. | Lm-LLO-NP | ±S.D. | Lm-LLO-E7 | ±S.D. | Lm-ActA-E7 | ±S.D. |
|---|---|---|---|---|---|---|---|
| 408 | 123 | 385 | 130 | 225 | 54 | 305 | 92 |

The difference in thyroid weight between Lm-LLO-E7 treated mice and untreated mice and between Lm-LLO-ActA treated mice and untreated mice was significant ($p<0.001$ and $p<0.05$, respectively), while the difference between Lm-LLO-NP treated mice (irrelevant antigen control) and untreated mice was not significant (Student's t test). Thus, vaccines of the present invention are able to prevent formation of new tumors with either Her-2 or E7.

To summarize the findings presented thus far, LLO-antigen and ActA-antigen fusions (a) induce tumor-specific immune response that include tumor-infiltrating antigen-specific T cells; and are capable of inducing tumor regression and controlling tumor growth of both normal and particularly aggressive tumors; (b) overcome tolerance to self antigens; and (c) prevent spontaneous tumor growth. These findings are generalizable to a large number of antigens, PEST-like sequences, and tumor types, as evidenced by their successful implementation with a variety of different antigens, PEST-like sequences, and tumor types.

Example 17

Figure 24A:
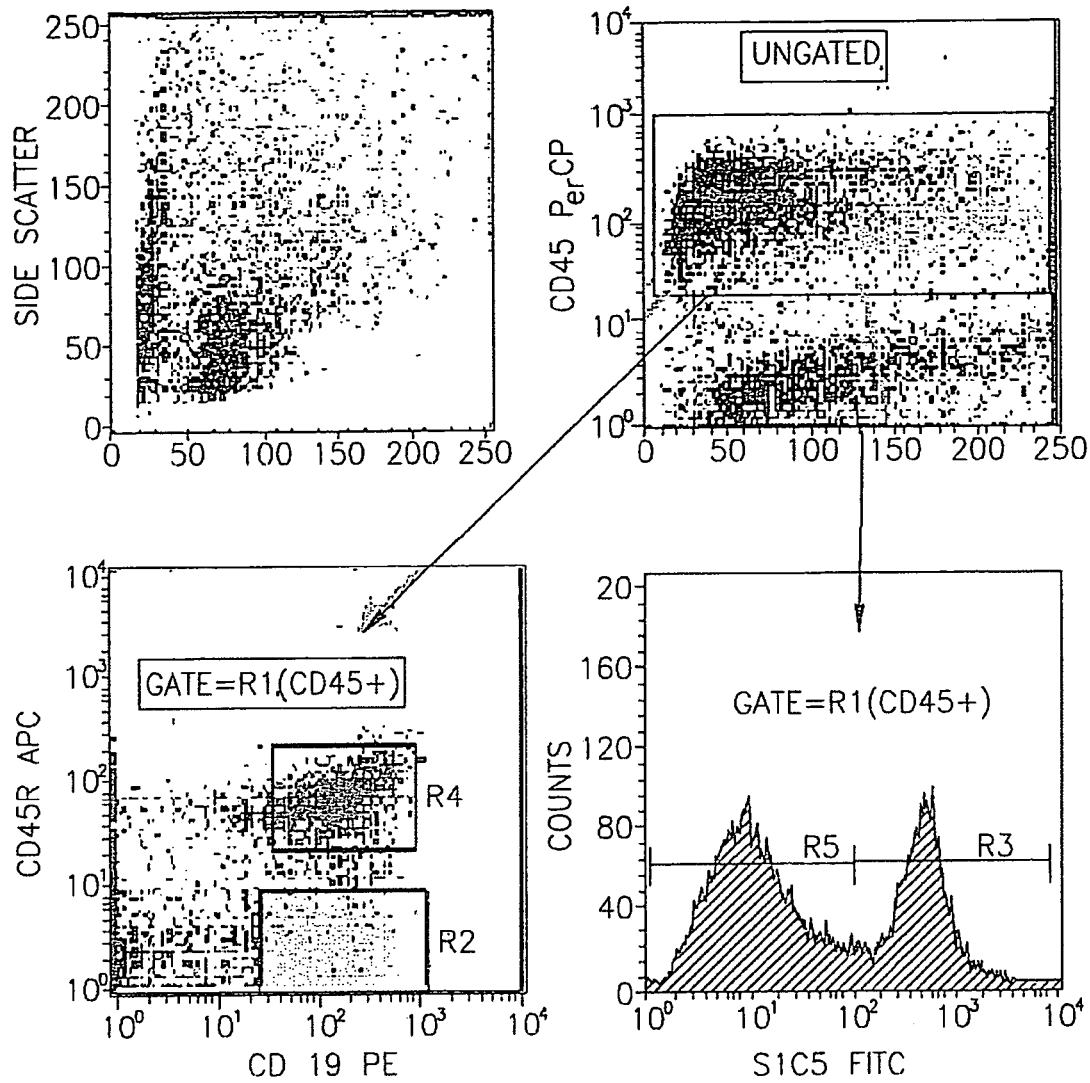
FIG. 24. A mixture of 38C13 (25%) and splenocytes (75%) were stained with the cocktail of antibodies and analyzed on the FACS by the MPFC assay. Gray dots represent 38C13 cells defined by cells that satisfy the gating criteria G3. Black dots represent normal B cells in the spleen, defined by G5. [B] In an in vitro seeding experiment, 38C13 or 38C13-V2 cells were mixed with normal splenocytes and the MPFC assay performed. Results are depicted for both cell lines and the regression analysis comparing the expected versus actual MPFC.
Figure 24B:
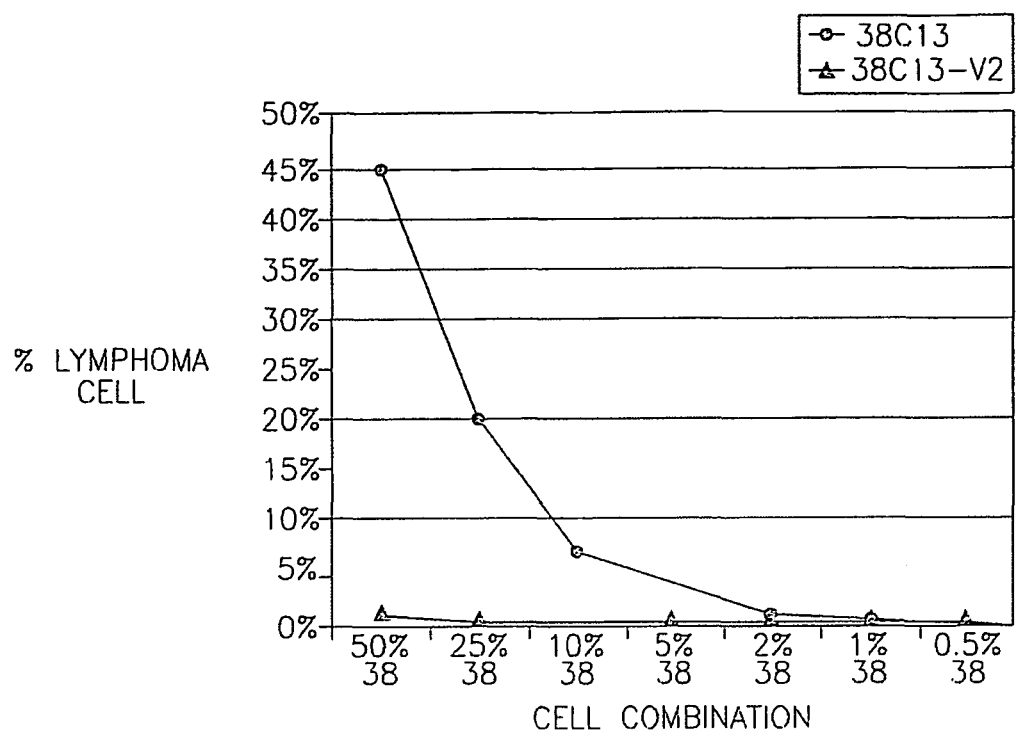
Figure 24B:
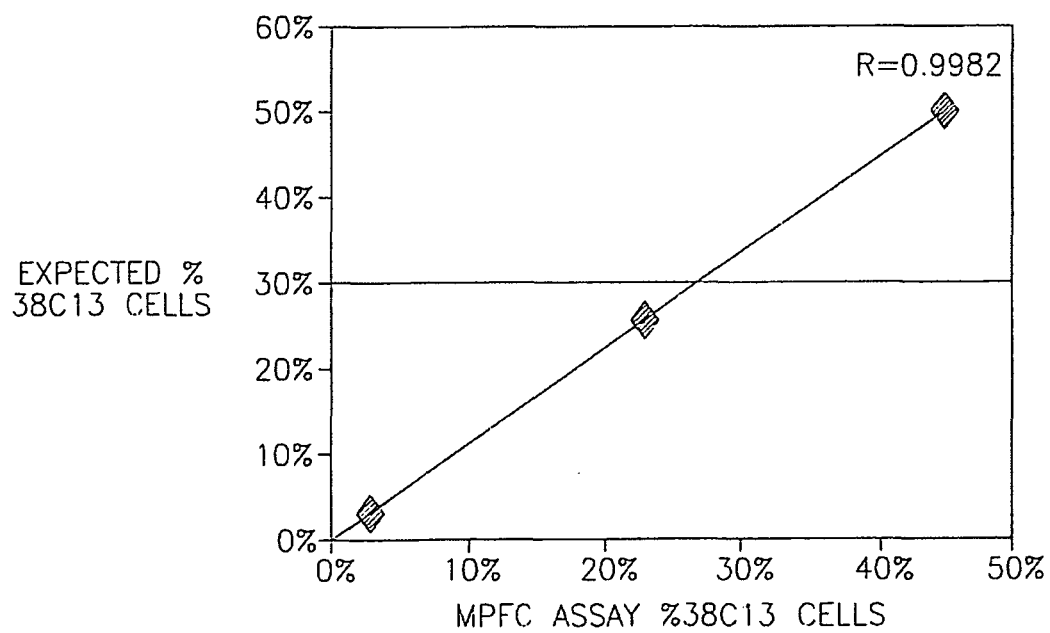

Development of a Multi-Parameter Flow Cytometric Assay to Monitor 38C13 Tumor Growth Kinetics The 38C13 carcinogen-induced B cell tumor from the C3H/HeN mouse was utilized as a mouse model for B cell lymphoma. To model 38C13 lymphoma growth kinetics in the C3H/HeN mouse, a multi-parameter flow cytometry (MPFC) assay was developed, based on the aberrant pattern of antigen expression of the 38C13 cells compared to normal lymphoid cells. The MPFC assay employs a mixture of conjugated antibodies, including monoclonal antibody (MAb) S1C5, specific for the B cell idiotype of 38C13, and a sequential gating technique to distinguish the 38C13 cells from normal cells. The MPFC assay defines 38C13 cells as $CD45^+/SSC^{hi}/CD19^+/CD45R^-/S1C5^+$ that are readily distinguished from normal B cells (FIG. 24A). It is a sensitive and specific method to identify 38C13 lymphoma cells and correlated closely with expected % 38C13 values in seeding experiments (FIG. 24B).

To test the lymphoma detection assay in vivo, C3H/HeN mice were inoculated, in two separate experiments, with 38C13 cells ($2 \times 10^3$ s.c.), and tumor growth kinetics were monitored at different time points between experiments. In addition, tumors and potential metastatic organs for B cell lymphoma were removed and analyzed by the MPFC assay. A subset of the lymphoid organs and tumors were also examined by histology and immuno-histochemistry to confirm the presence of 38C13 lymphoma metastases. The results for mean diameter of the s.c. tumors from days 0 to day 17 indicate different growth kinetics of the 38C13 cells between parts one and two of the study. Once the s.c. tumors reached a mean diameter size of 1 cm, all tumors consisted largely of 38C13 cells. Tumors excised from the s.c. inoculation site at day 6 were not palpable (n=4), but were clearly demonstrated to contain substantial numbers of 38C13 lymphoma cells (n=3/4). In addition, at day 6 in the s.c. tumors, a cluster of cells were frequently present that were $CD45^{hi}/SSC^{lo}$. These cells were later demonstrated to be tumor-infiltrating lymphocytes. This $CD45^{hi}/SSC^{lo}$ cluster of cells was not a significant presence in the s.c. tumors, once they reached a mean diameter of 1 cm.

Example 18

Ability of the MPFC Assay to Detect Lymphoma Metastases is Confirmed by Histology and Immunohistochemistry The MPFC assay was used to examine 38C13 lymphoma spread from i.p. and s.c. inoculation sites. Following i.p. inoculation, the MPFC assay detected 38C13 cell spread to the spleen, mesenteric and inguinal lymph nodes by day 6, and the organ involvement with lymphoma increased until day 17 post-inoculation. Bone marrow metastases were detectable three days later than in the spleen and lymph nodes, and exhibit the same gradual increase from day 9 onwards. Similarly, following s.c. inoculation of 38C13 cells into the right flank, the lymphoma cells rapidly established a tumor by day 6; at this stage the 38C13 cells had already migrated to the draining brachial lymph nodes and were detectable in the spleen. Subsequently, the 38C13 cells migrated to the bone marrow by day 9. Lymphoma involvement in these three organs increased until day 17, at which stage the primary tumors had grown to a substantial size, requiring the mice to be sacrificed.

Histology and immunohistochemistry were then used to confirm the 38C13 lymphoma metastases in the spleen. Tumors excised following s.c. or i.p. inoculation were defined by the pathologist as a large cell lymphoma (LCL), immunoblastic type. As demonstrated by IHC, the 38C13 cells in these tumors were $B220^-/S1C5^+$, and these results correlated with flow cytometry results. Also, a set of spleen sections were examined by histology and IHC to test correlation of the data with the MPFC assay (Table 2). Spleens from mice inoculated with 38C13 cells exhibited 3 distinct patterns of lymphoma involvement, diffuse, focal or negative by histology and IHC. Furthermore, the MPFC assay result for these distinct patterns of involvement fell into three ranges, (20-30)% for diffuse involvement, (5-15)% for focal involvement and <5% for spleen sections interpreted as negative by histology.

TABLE 2

Confirmation of MPFC assay results of 38C13 tumor metastatic spread by histology and immuno-histochemistry.

| Specimen | H&E | B220 | S1C5 | MPFC assay |
|---|---|---|---|---|
| s.c. day 6 | Neg | +++ normal B cell | Neg | 3.7% |
| s.c. day 6 | " | +++ normal B cell | Neg | 2.3% |
| s.c. day 11 | Focal involvement | ND | ND | 12.6% |
| s.c. day 17 | " | ++ normal B | ++ LCL in PALS and red pulp | 13.25% |
| s.c. day 17 | " | ++ normal B | ++ LCL in PALS and red pulp | 14.7% |
| i.p. day 11 | Diffuse involvement | + normal B | ++++ LCL in PALS and red pulp | 25.6% |
| i.p. day 17 | " | " | ++++ LCL in PALS and red pulp | 24.7% |
| Control day 0 | Neg | +++ normal B | Neg | 0.8% |
| Control day 6 | " | " | " | 1.9% |
| Control day 9 | " | " | " | 1.5% |
| Control day 12 | " | " | " | 0.2% |

Example 19

Expression of the 38C13 BCR as an scFv Protein

A modified pUC119 plasmid was utilized to express the scfv protein in *E. coli* (Sure® strain, Statagene, La Jolla, Calif.). The plasmid contained the 38C13 scFv DNA (provided by Dr. Levy), sequences coding for the bacterial leader pelB (facilitates secretion of the protein into the periplasmic space) and the human c-myc peptide tag, which aids detection of protein expression in *E. coli* and purification of the tumor antigen. The 38C13 VH sequence starts with the Gly residue encoded by residues 133-135 and ends with the Val residue encoded by residues 478-480. The 38C13 VK sequence starts with the Glu residue encoded by residues 538-540). The 38C13 VK has a myc tag on the end; the VK ends with a Lys (encoded by residues 848-850)

The relevant fragment of the plasmid had the following sequence:

```
GCCCAGCCGCCATGCCAGGTGAAGCTGCAGGAGTCA (SEQ ID No:47)
GGAGGAGGCTTGGTCCAGCCTGGGGGTTCTCTGAGT
CTCTCCTGTGCAGCTTCTGGATTCACCTTCACTGAT
TACTACATGAGCTGGGTCCGCCAGCCTCCAGGGAAG
GCACTTGAGTGGTTTGGCTTTGATTAGAAACAAAGC
TAATGGTTACACAGAGTACAGTGCATCTGTGAAGGG
TCGGTTCACCATCTCCAGAGATAATTCCCAAAGCAT
CCTCTATCTTCAAATGAATGCCCTGAGAGCTGAGGA
CAGTGCCACTTATTACTGTGCAAGAGATCCCAATTA
CTACGATGGTAGCTACGAAGGGTACTTTGACTACTG
GGGCCAAGGGACCACGGTCACCGTCTCCTCAGGCGG
AGGCGGTTCAGGCGGAGGTGGCTCTGGCGGTGGCGG
ATCGGACATTGAGCTCACCCAGTCTCCATCCTCACT
GTCTGCATCTCTGGGAGGCAAAGTCACCATCACTTG
CAAGGCAAGCCAAGACATTAACAAGTATATAGCTTG
GTACCAACACAAGCCTGGAAAAGGTCCTAGGCTGCT
CATACATTACACATCTACATTACAGCCAGGCATCCC
ATCAAGGTTCAGTGGAAGTGGGTCTGGGAGAGATTA
TTCCTTCAGCATCAGCAACCTGGAGCCTGAAGATAT
TGCAACTTATTATTGTCTACAGTATGATAATCTGTA
CACGTTCGGCTCGGGGACCAAGCTGGAAATAAAACG
GGCGGCCGCAGAACAAAACTCATCTCAGAAGAGGA
TCTGAATTAATAAGAATTC.
```

The encoded protein had the sequence:

```
MKYLLPTAAAGLLLLAAQPAQPPCQVKLQESGGGLV (SEQ ID No:48)
QPGGSLSLSCAASGFTFTDYYMSWVRQPPGKALEWL
ALIRNKANGYTEYSASVKGRFTISRDNSQSILYLQM
NALRAEDSATYYCARDPNYYDGSYEGYFDYWGQGTT
VTVSSGGGGSGGGGSGGGGSDIELTQSPSSLSASLG
GKVTITCKASQDINKYIAWYQHKPGKGPRLLIHYTS
TLQPGIPSRFSGSGSGRDYSFSISNLEPEDIATYYC
LQYDNLYTFGSGTKLEIKRAAAEQKLISEEDLN.
```

Initially, the 38C13 plasmid was transformed in to the *E. coli* strain BL21*. Following IPTG-induction, the BL21* cells expressed the recombinant protein, with a minor fraction present in the periplasmic space, and the majority present in the *E. coli* inclusion bodies. The inclusion bodies were solubilized (at <80 ug/ml total protein) in 6M guanidine; the solubilized proteins were refolded in the presence of L-arginine, oxidized glutathione, and EDTA at 10° C. for 3-5 days. The refolded 38scFv protein was then purified from other proteins on an immuno-affinity column containing the S1C5 antibody (anti-38C13 BCR clone) linked to CNBr sepharose using the Amino-link® kit (Pierce Endogen).

Figure 25:
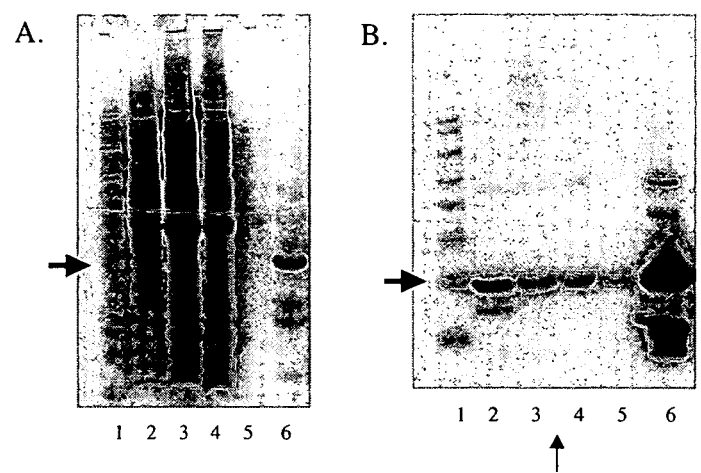
FIG. 25. Expression of 38C13 soluble protein yields 2.34 mg soluble protein from the cell pellet per liter of induction medium. Induction of 38C13scFv protein expression in BL21* was performed using 1 mM IPTG in Superbroth containing 0.5% glycine and 1% triton X-100 at 20° C. for 16 hours. Soluble proteins were extracted from the cell pellet using a protocol including freeze/thaw in nonionic detergent, lysozyme and sonication. 38scFv proteins were purified from the extracted soluble proteins in the anti-idiotype sepharose column. Samples from the affinity chromatography study were electophoresed on SDS-PAGE gels and Coumassie staining (A) or myc tag Western (B). The flow through (ft) and wash fractions contained the 38scFv protein, indicating the Id-Sepharose® column was overloaded with the protein. These fractions were re-loaded onto the Id-Sepharose® slurry and further recombinant protein recovered. Lanes: 1—M Wt; 2—soluble fraction; 3—ft; 4—wash at 1 ml; 5—wash at 100 ml; 6—pooled elution fraction.
Figure 26:
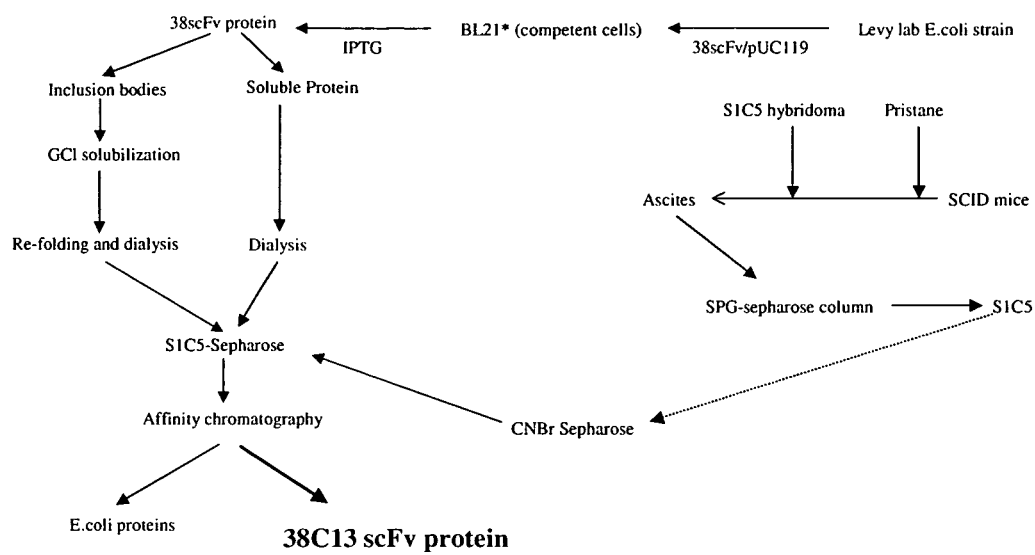
FIG. 26. Strategy for 38scFv protein expression in E. coli and subsequent purification by affinity chromatography. Diagram shows the pathway for production of purified 38C13scFv and subsequent purification on an immunoaffinity column with the anti-Id antibody S1C5.

To increase the yield, recombinant protein was recovered from soluble protein extracts. Induction of 38C13scFv expression and recovery of soluble versus insoluble protein at 20° C. and 30° C. were compared. Greater yields of soluble 38C13scFv were recovered by induction at 20° C. Furthermore, maximal yield of soluble protein in the culture supernatant (SN) or from cells was achieved when 0.5% glycine or 1% TX-100 was included in the induction medium. Finally, a 1-liter induction culture performed in medium containing 0.5% glycine and 1% TX-100 yielded 2.34 mg pure soluble 38C13scFv following affinity chromatography (FIG. 25). The overall strategy for production of scFV tumor antigen is summarized in FIG. 26.

Example 20

Verification of 38C13 scFV Conformational Integrity by ELISA

Figure 27:
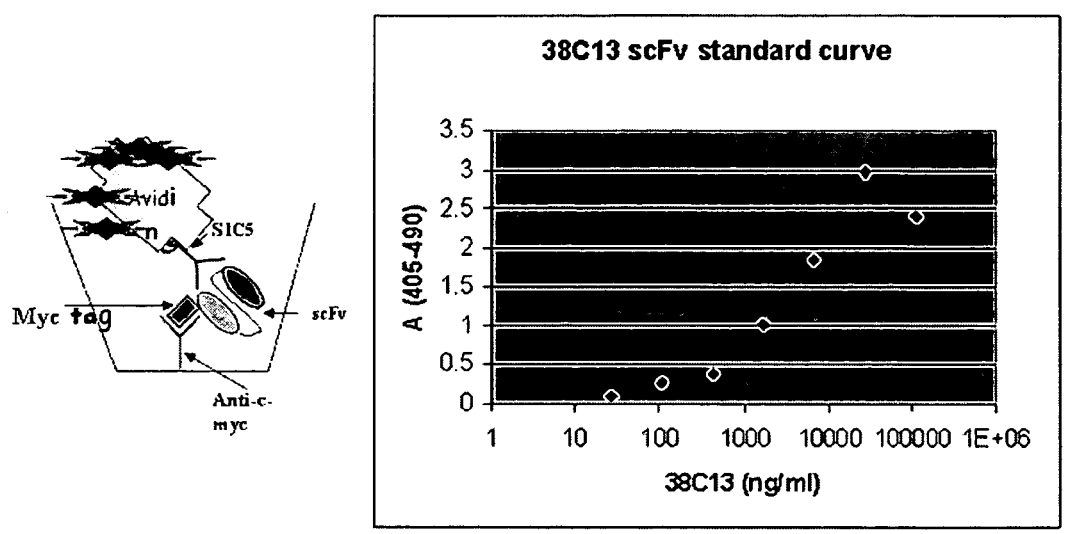
FIG. 27. ELISA assay to quantitate 38C13scFv production in induction cultures, to test correct folding of the protein after conjugation to immunogens, and to monitor the humoral immune response. The principle of the ELISA assay is depicted in (a). A standard curve (b) shows the change in A(405-490) for serial dilutions of purified 38scFv.

To verify that correctly folded 38C13scFv protein was produced by the above method, an ELISA assay was developed. Using serial dilutions of purified 38C13scFv protein, a standard curve was established. This assay showed that correctly folded 38C13scFv protein was produced (FIG. 27). This ELISA assay can also be used to quantitate correctly folded soluble protein in induction media as well as cell protein extracts, for further optimization of conditions for producing 38C13scFv protein.

Production of LLOdetox:

The gene encoding LLOdetox (AA sequence 20 to 442 of LLO, excluding the signal sequence) was cloned from pGG55 and inserted into the multi-cloning site of pET29b, which has a $(HIS)_6$ tag at the 3' end. The resulting plasmid was restriction digested to verify the correct orientation of the gene for expression, then used to transform *E. coli* strain BL21 (DE3) (Novagen). A log phase culture was induced with 500 mcM IPTG (final concentration) overnight, and cells were pelleted, lysed with BugBuster® (Novagen)+Benzonase+0.5 mg/ml Lysozyme+Complete Protease Inhibitor Mix, and incubated at 4° C. for 15 min. Insoluble material was pelleted by centrifugation, the soluble fraction was allowed to bind to a $Ni^{++}$ column, then purified protein was eluted as described in Glomski, I J, Gedde M M et al. (J. Cell Biol. 156:1029-38, 2002). The size and purity of the protein product was verified on Coomassie stained gels, followed by Western blot using an LLO-specific MAb. Endotoxin purification was then performed using a Polymixin B agarose column, and endotoxin removal confirmed by a functional assay (*Limelus Amebocyte* lysis test).

Example 21

Construction of the 38C13 BCR-LLO Vaccine

Purification of Idiotype Proteins.

Figure 28:
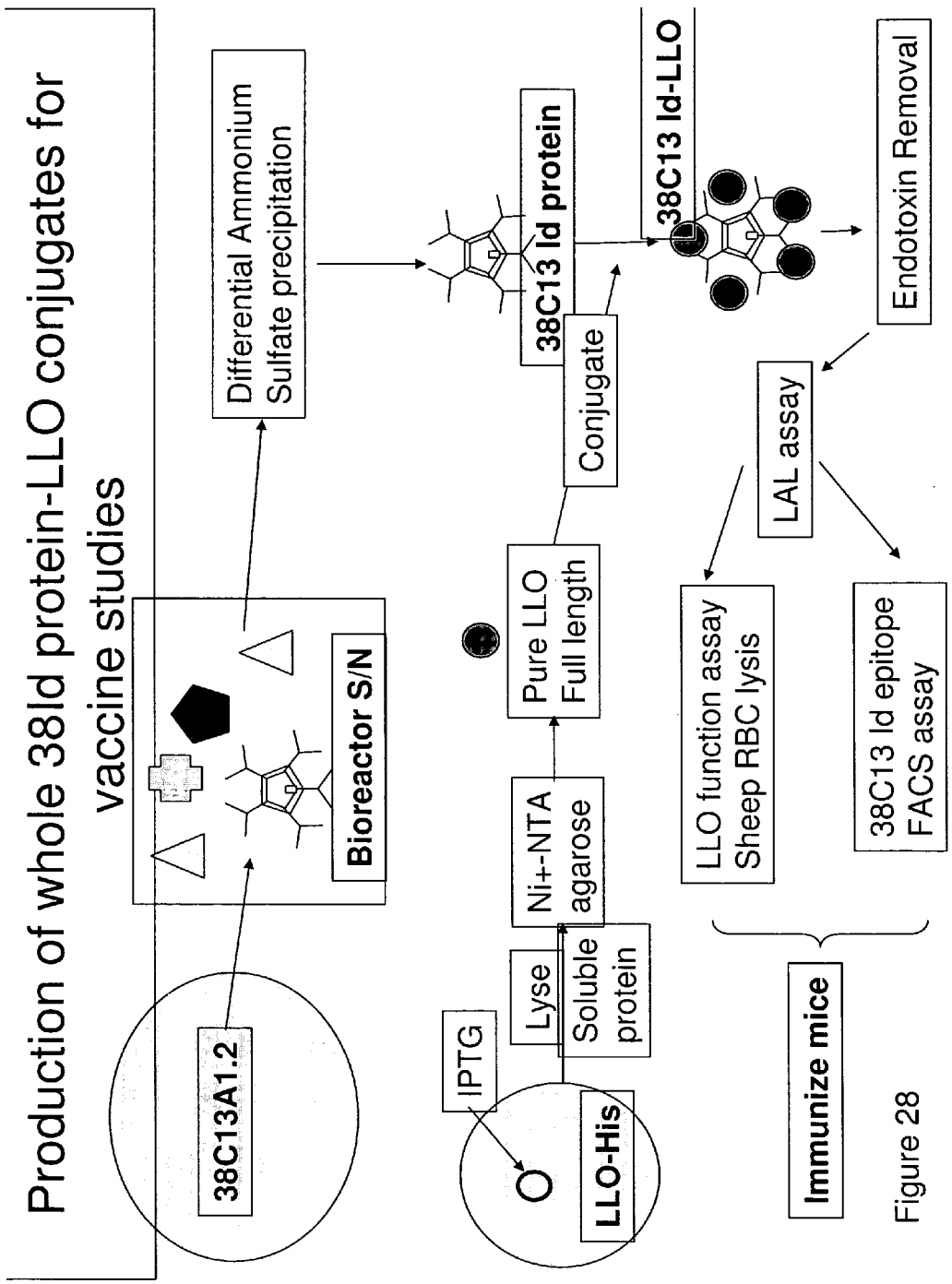
FIG. 28. The 38C13 IgM protein was secreted by the 38C13A1.2 hybridoma into the bioreactor culture supernatent. The 38C13 IgM protein was purified from the culture supernatant using differential ammonium sulfate precipitation. In addition, soluble LLO-His protein was expressed in E. coli following induction by IPTG, the soluble protein was then purified on a Ni+-NTA column and purity confirmed by Coumassie and Western blot using the LLO antobody B3-19. The 38C13 Id protein was conjugated to glutaraldehyde, dialyzed against PBS and passed through a Polymixin B column to remove endotoxin; endotoxin removal was confirmed by the LAL assay. The hemolytic activity of the 38Id-LLO conjugate was then tested using sheep red cells and compared to purified LLO, the 38Id-LLO was found to be non-hemolytic.
Figure 29:
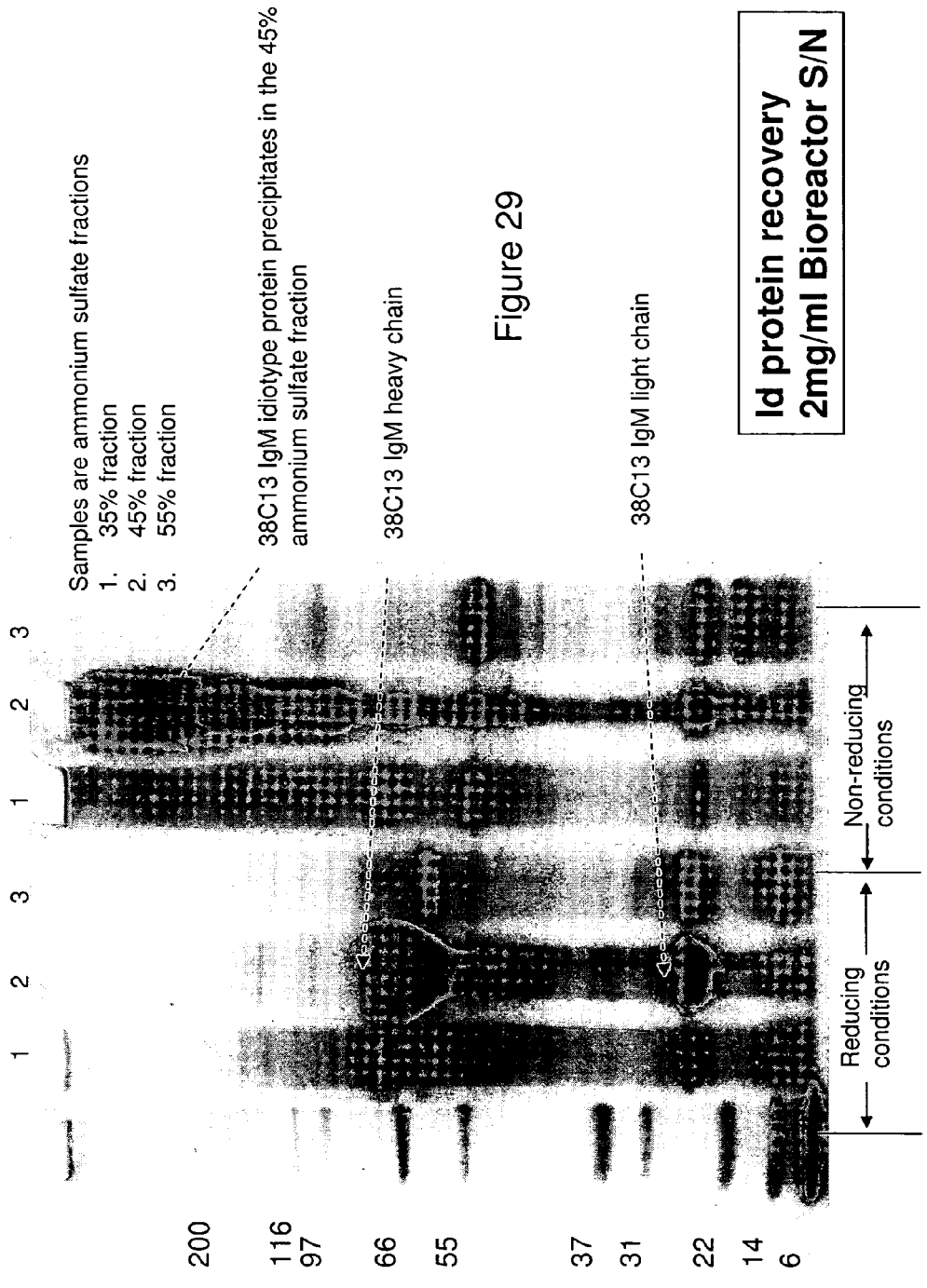
FIG. 29. Samples from differential ammonium sulfate precipitation of bioreactor supernatent following culture of the hybridoma 38C13A1.2 were run by SDS PAGE gel and stained by Coumassie. The 38C13 idiotype protein was recovered from the 45% fraction and characterized in both reducing and non-reducing conditions.

B-cell lymphoma idiotype proteins were purified from hybridoma supernatant via differential ammonium sulfate precipitation. The process for production of the 38C13 lymphoma idiotype protein is outlined in FIG. 28. The 38C13A1.2 hybridoma secreted the IgM protein into the Bioreactor (BD Celline) supernatant. The IgM protein was recovered from the bioreactor supernatant following differential ammonium sulfate precipitation. Samples from each fraction were run by SDS-PAGE under reducing and non-reducing conditions and characterized by Coumassie stain (see FIG. 29). The 45% fraction from the bioreactor supernatant contained the 38C13 IgM protein; recovery was 2 mg/ml supernatant.

Figure 30:
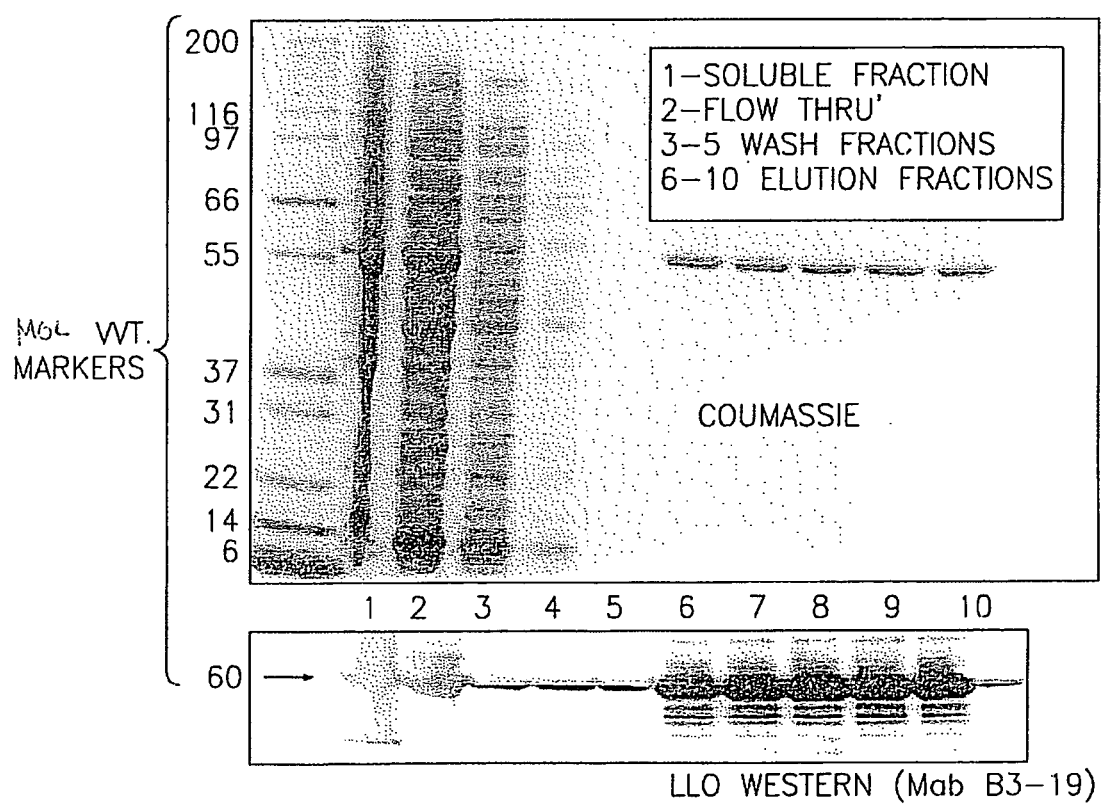
FIG. 30. Soluble proteins were recovered from E. coli strain BL21* following an induction expression culture in LB medium and 1 mM IPTG for 18 hours at 30 C. Recombinant LLO-His was then purified on a Ni+-NTA column; the purity of the elution fractions were confirmed by SDS PAGE followed by a Coumassie stain or a Western blot performed using Mab B3-19.

Recombinant LLO was recovered from soluble proteins from BL21* following IPTG-induced expression induction for 18 hours at 30° C. The soluble proteins were incubated in batch form with $Ni^+$-NTA agarose for 30 minutes at room temperature. Non-specifically bound proteins were removed following a washing step in phosphate buffer, pH 8 containing 20 mM imidazole. The recombinant LLO-His was then eluted from the column using phosphate buffer pH 8 plus 500 mM imidazole. The purity of the elution fractions was confirmed by SDS PAGE followed by Coumassie stain or Western blot using the Mab B3-19. Results show (FIG. 30) that a single band of molecular weight 58 kD was eluted from the $Ni^+$-NTA column and its identity as confirmed as LLO by the Mab B3-19.

Figure 31:
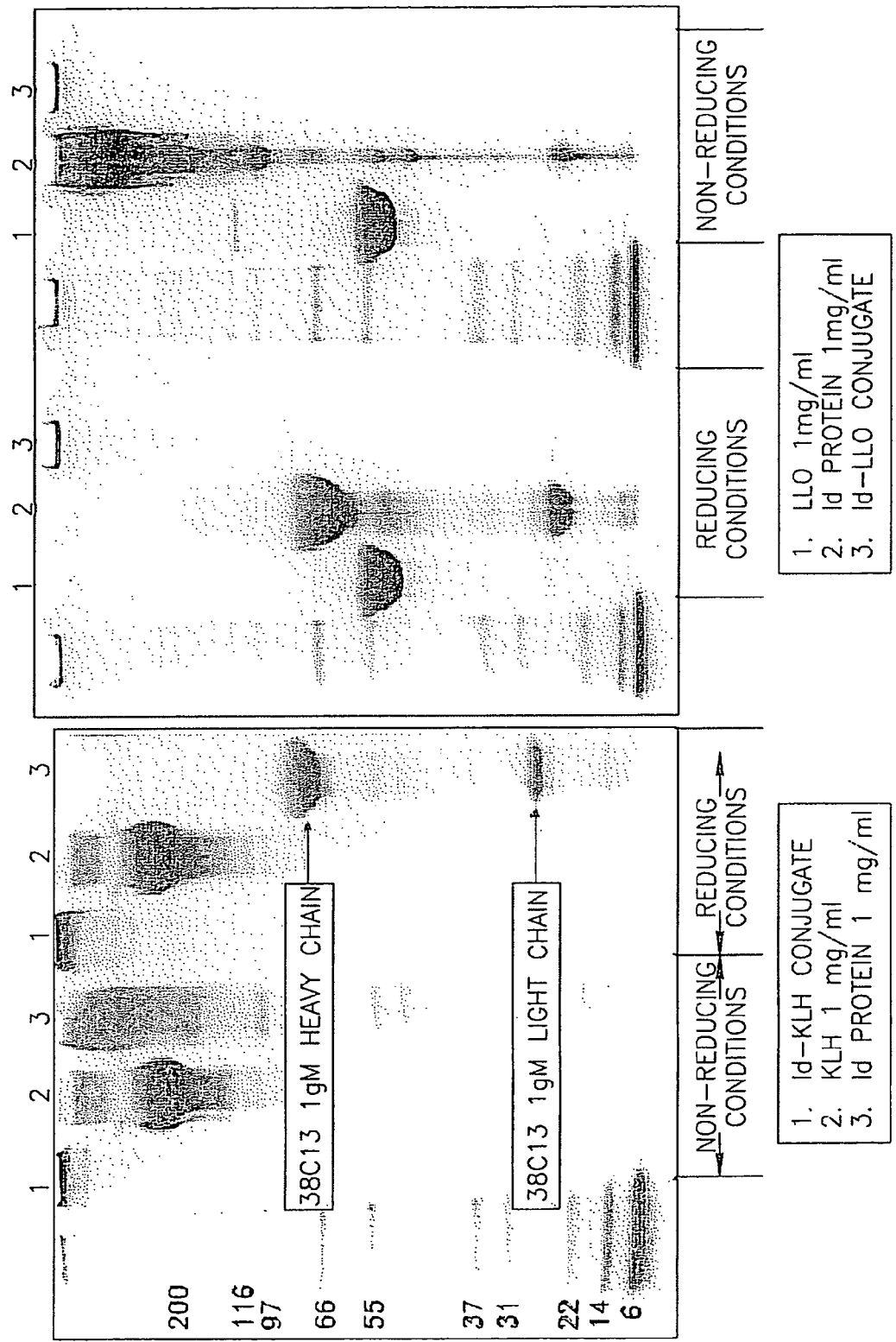
FIG. 31. 38C13 idiotype (Id) protein was conjugated to either KLH (left panel) or LLO (right panel). The conjugation of the 38Id was confirmed by Coumassie stain on a SDS PAGE gel run under reducing and non-reducing conditions; both 38Id-KLH and 38Id-LLO conjugates show no evidence of free 38Id or the immunogenic proteins.
Figure 32:
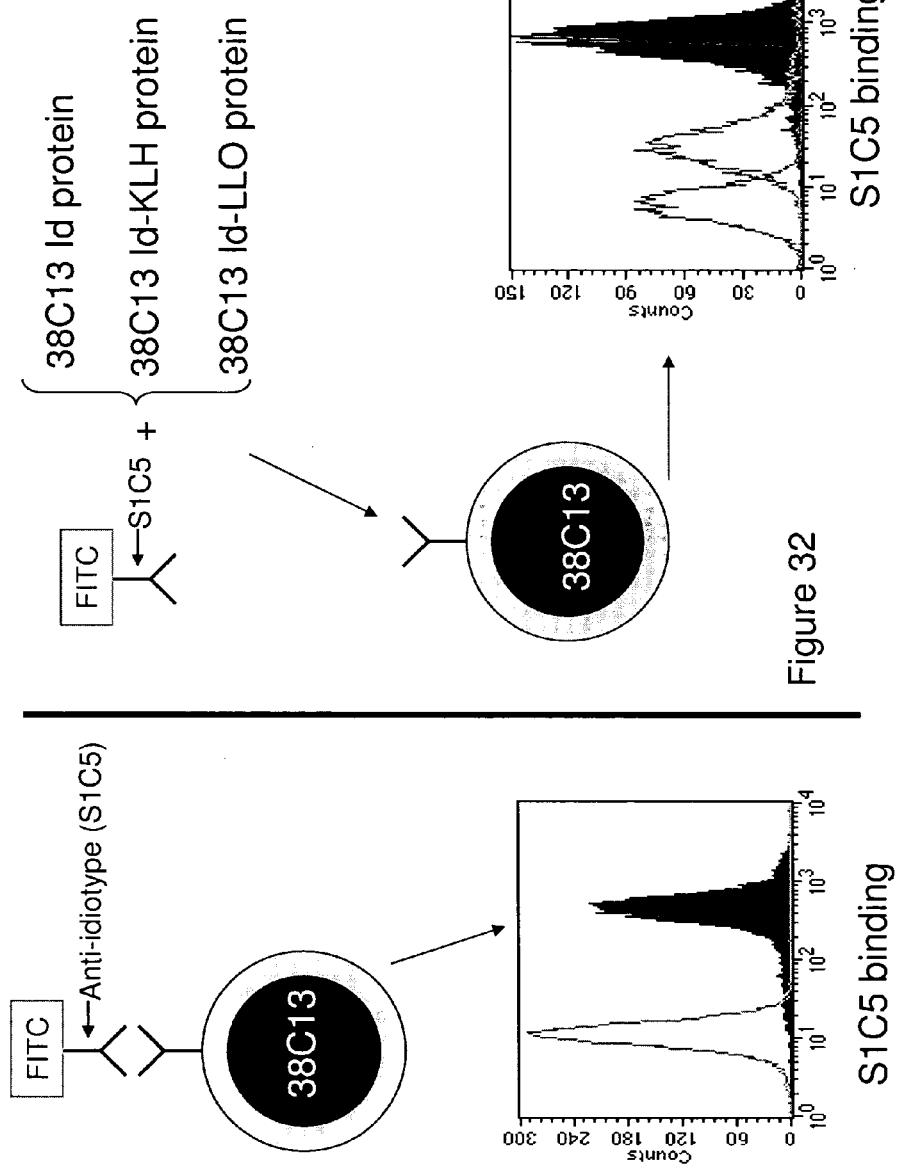
FIG. 32. Principle of the assay system designed to demonstrate the presence of the 38C13 idiotype epitope. The presence of the 38C13 idiotype epitope was confirmed using a blocking assay, in this system the anti-38C13 idiotype antibody S1C5-FITC is incubated with the Id protein or the conjugates 38Id-KLH or 38Id-LLO. Subsequently the binding of the S1C5-FITC to the 38C13 cell line BCR is assessed by flow cytometry. In the presence of 38Id protein, the binding of S1C5-FITC to 38C13 lymphoma is impaired.
Figure 33:
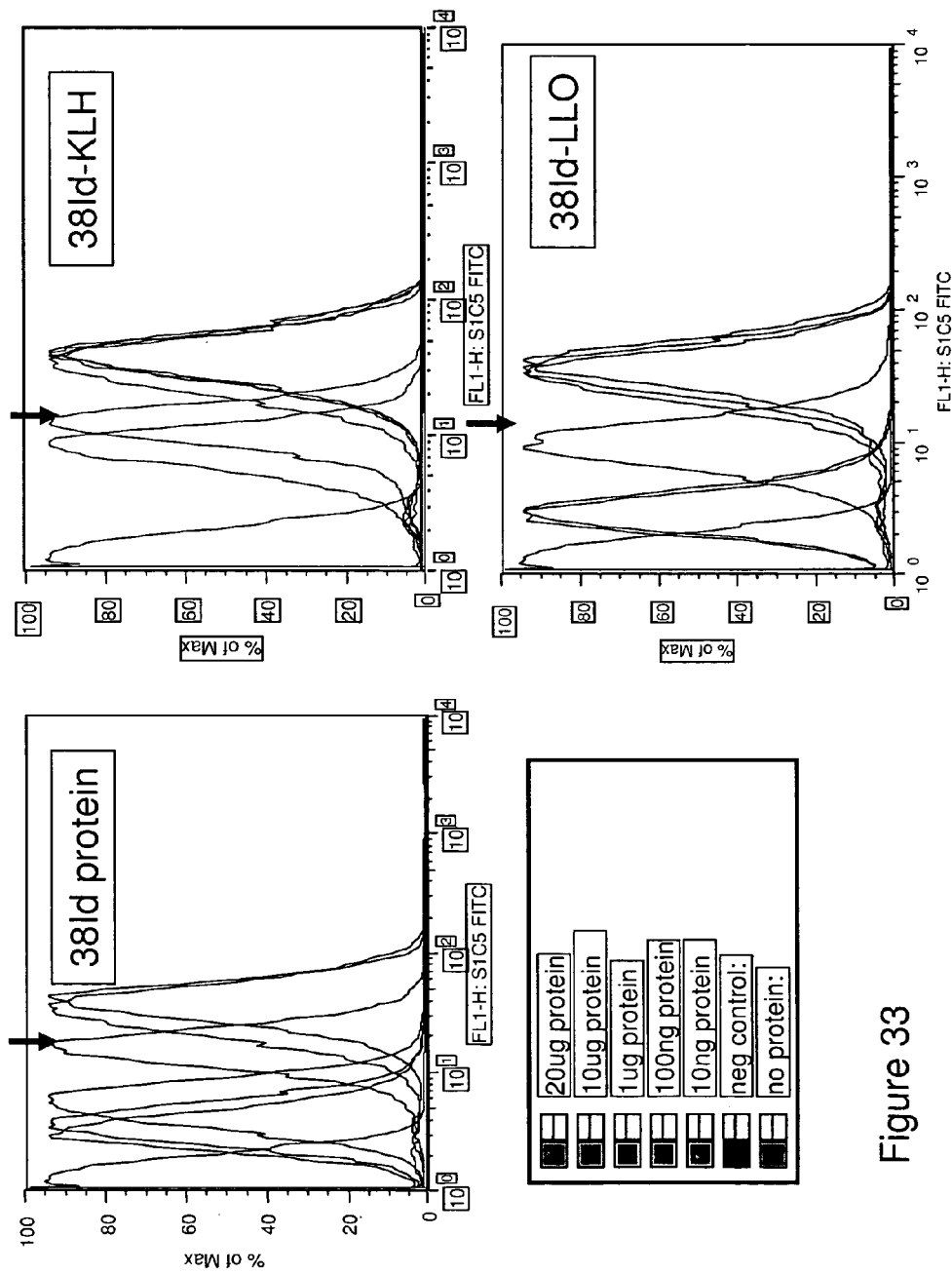
FIG. 33. 38C13 Id protein conjugated to LLO or KLH retains the binding site for the S1C5 MAb and inhibits binding of S1C5-FITC to 38C13 lymphoma cells.

Subsequently, the 38C13 idiotype protein was conjugated to recombinant LLO or KLH using 0.1% glutaraldehyde for 10 minutes at room temperature. The glutaraldehyde was removed following dialysis against 0.1M PBS at 4° C. overnight. The 38Id-LLO and 38Id-KLH conjugates were then characterized by SDS-PAGE under reducing and non-reducing conditions followed by Coumassie stain (see FIG. 31). Results showed the conjugation was successful with no free 38Id protein nor immunogenic protein in either conjugate. To identify the 38C13 idiotype epitope was still present following conjugation, a FACS-based competitive binding assay was developed (see FIG. 32). This assay detects the ability of the 38Id conjugate to block the specific binding of FITC conjugated S1C5 Mab to the 38C13 lymphoma BCR. The presence of 100 ng 38Id protein was sufficient to block binding of the 0.1 ug S1C5 Mab to 38C13 lymphoma cells (FIG. 33). In contrast, 1 mcg 38Id-LLO or 10 mcg 38Id-KLH were required to block binding of 0.1 mcg S1C5 Mab to 38C13 lymphoma cells.

Example 22

Figure 34:
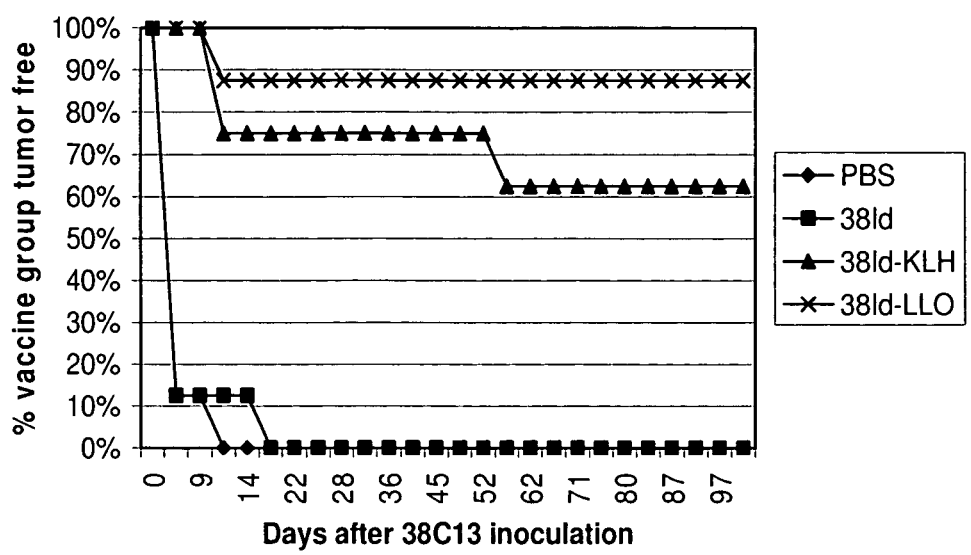
FIG. 34. 38C13 lymphoma protection study.
Figure 35:
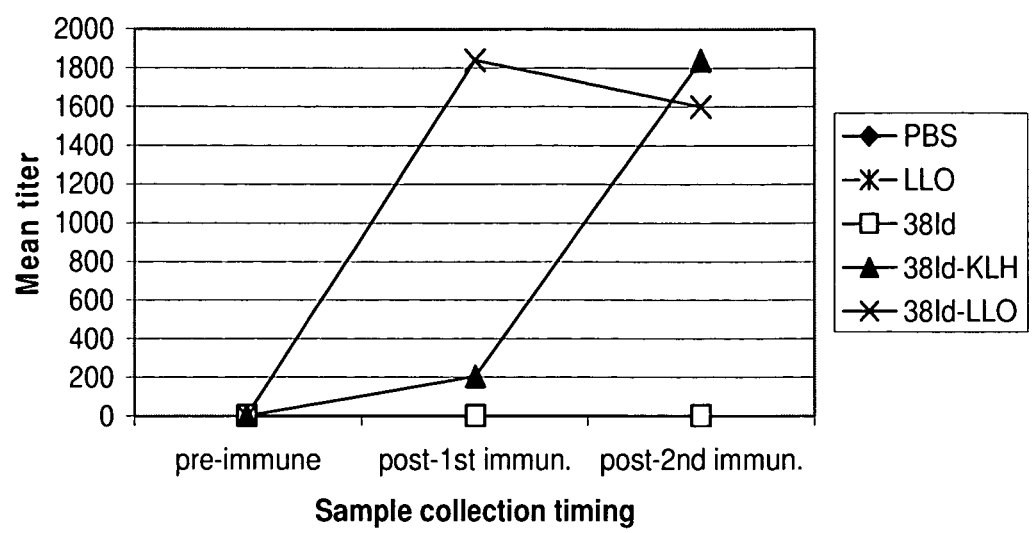
FIG. 35. Anti-Id antibody responses to LLO-Id vaccines.

Comparison of Efficacy of 38C13-LLO and 38C13/KLH in a Mouse Non-Hodgkin's Lymphoma Tumor Protection Model C3H/HeN mice (n=8) were vaccinated with (a) 38C13 idiotype protein (38-Id), (b) 38Id coupled to Keyhole Limpet Hemocyanin (38Id-KLH); (c) 38Id-LLO; or (d) PBS (negative control). Vaccines were administered as two 50 mcg s.c. doses on days 0 and 14 days, with 10,000 U murine GMCSF (mGMCSF). In addition, 10,000 U mGMCSF was administered on the same flank for three consecutive days. On day 28, mice were challenged with $10^3$ 38C13 cells on the flank used for immunization and tumor formation was monitored for 100 days. Mice that received 38Id-LLO formed tumors with significantly lower frequency (1/8; p=<0.05) versus the control groups, which developed tumors within 10 days of 38C13 inoculation 7/8 for 38Id and 8/8 for PBS (FIG. 34). 38Id-LLO immunization was also associated with high titer anti-38Id antibodies (FIG. 35) and cell-mediated immunity. Surviving mice from the 38Id-LLO group were also protected from 38C13 tumor challenge on the flank opposite the immunization site, showing that the protective immunity was systemic. Mice that received 38Id-KLH were also protected from tumor formation, but with lower frequency (3/8 formed tumors) than 38Id-LLO.

Additional Studies

Study #1:

C3H mice, 10 mice per group, are immunized with 50 mcg of the antigens listed in Table 3, together with 67 mcl SBAS2 (saponin QS21 and monophosphoryl lipid A in an oil and water emulsion). Vaccines are administered s.c., in 4 sites along the back, in a volume of 50 mcl. Mice are administered 2 immunizations on days 0 and 14, and then challenged with 38C13 or 38C13V2 (an antigen loss variant) tumors by injecting $2 \times 10^3$ cells s.c. After tumor challenge the growth of the primary tumor is measured using electronic calipers. Animals that develop a primary tumor that reaches 2.0 cm, (for naive animals, around day 15), are sacrificed and residual disease in the spleen, inguinal and mesenteric lymph nodes is measured using the MPFC assay. Statistical analysis (log-ranked Kaplan Meier test) is performed to determine whether reduction in tumor size and cure rate are statistically significant.

TABLE 3

Immunization groups for study #1.

| Group | Immunization |
| --- | --- |
| 1 | 38C13 BCR-KLH- challenge with 38C13 |
| 2 | 38C13 BCR-LLO- challenge with 38C13 |
| 3 | LLO mixed with 38C13 BCR- challenge with 38C13 |
| 4 | KLH mixed with 38C13 BCR- challenge with 38C13 |
| 5 | 38C13 BCR alone- challenge with 38C13 |
| 6 | Adjuvant (SBAS2) alone- challenge with 38C13 |
| 7 | Mock vaccinated- challenge with 38C13 |
| 8 | 38C13 BCR-KLH - challenge with 38C13V2 |
| 9 | 38C13 BCR-LLO - challenge with 38C13V2 |

Study #2:

Instead of SBAS2, the unmethylated CpG oligonucleotide TCCATGACGTTCCTGACGTT (1826; SEQ ID No: 45) is utilized. As a negative control, oligonucleotide TCCAG-GACTTCTCTCAGGTT (1982; SEQ ID No: 46), a control oligodeoxynucleotide that does not contain CpG sequences, is utilized (Table 4).

Study #3.

Instead of SBAS2, 10,000 units of GM-CSF is utilized. Otherwise design is as in Table 4, minus the 2 groups administered oligonucleotide 1982.

TABLE 4

Immunization groups for study #2.

| Group | Immunization |
|---|---|
| 1 | 38C13 BCR-KLH + 1826- challenge with 38C13 |
| 2 | 38C13 BCR-KLH + 1982 - challenge with 38C13 |
| 3 | 38C13 BCR-LLO + 1826- challenge with 38C13 |
| 4 | 38C13 BCR-KLH + 1982 - challenge with 38C13 |
| 5 | LLO mixed with 38C13 BCR + 1826- challenge with 38C13 |
| 6 | KLH mixed with 38C13 BCR + 1826- challenge with 38C13 |
| 7 | 38C13 BCR alone + 1826- challenge with 38C13 |
| 8 | Adjuvant (1826) alone- challenge with 38C13 |
| 9 | Mock vaccinated- challenge with 38C13 |
| 10 | 38C13 BCR-KLH + 1826 - challenge with 38C13V2 |
| 11 | 38C13 BCR-LLO - challenge with 38C13V2 |

Study #3:

Dose optimization. Four different doses of the vaccine are used (from 20-100 mcg) with either SBAS2, oligonucleotide 1826, or GM-CSF. (Table 5)

TABLE 5

Immunization groups for study #3.

| Group | Immunization |
|---|---|
| 1 | 20 mcg 38C13 BCR-KLH + 1826 - challenge with 38C13 |
| 2 | 40 mcg 38C13 BCR-KLH + 1826 - challenge with 38C13 |
| 3 | 70 mcg 38C13 BCR-KLH + 1826 - challenge with 38C13 |
| 4 | 100 mcg 38C13 BCR-KLH + 1826 - challenge with 38C13 |
| 5 | 20 mcg 38C13 BCR-LLO + 1826 - challenge with 38C13 |
| 6 | 40 mcg 38C13 BCR-LLO + 1826 - challenge with 38C13 |
| 7 | 70 mcg 38C13 BCR-LLO + 1826 - challenge with 38C13 |
| 8 | 100 mcg 38C13 BCR-LLO + 1826 - challenge with 38C13 |
| 9 | 100 mcg 38C13 BCR alone + 1826- challenge with 38C13 |
| 10 | Adjuvant (1826) alone- challenge with 38C13 |
| 11 | Mock vaccinated- challenge with 38C13 |
| 12 | 100 mcg 38C13 BCR-KLH + 1826 - challenge with 38C13V2 |
| 13 | 100 mcg 38C13 BCR-LLO + 1826 - challenge with 38C13V2 |

Example 23

Comparison of Efficacy of 38C13scFv-LLO and 38C13scFv/KLH in a Mouse Non-Hodgkin's Lymphoma Tumor Therapy Model Successful vaccine strategies from Example 22 are next tested in a tumor therapy model. 38C13 or 38C13V2 tumors are established as described in Example 22, then mice (n=10) receive either (a) 38C13 BCR-KLH; (b) 38C13 BCR-LLO; (c) LLO mixed with 38C13 BCR; (d) KLH mixed with 38C13 BCR; or (e) 38C13 BCR alone. After immunization, growth of the primary tumors is measured as described in Example 22. Animals in which the primary tumor regresses or growth is arrested are kept until day 45, then are sacrificed and examined for metastatic disease using the MPFC assay.

Example 24

Further Measurement of Immunity Induced by 38C13 BCR Vaccines

Anti-idiotypic immunity is measured in peripheral lymphoid organs, using the most effective immunization protocol/adjuvant system identified in the previous 2 Examples for 38C13 BCR-LLO and 39C13scFv-KLH.

Humoral Immunity:

Anti-scFv serum titers induced by 38C13 BCR-LLO and 39C13scFv-KLH vaccines are measured using ELISA with recombinant 38C13 BCR as antigen. 4 mice per group are immunized with 38C13 BCR-LLO and 39C13scFv-KLH vaccines, and blood is collected at days 0, 7 and 14. Serum from each mouse is titered against 38C13 BCR using a sandwich ELISA as described in FIG. 27, except that titered sera is used in lieu of biotinylated S1C5, and horseradish peroxidase conjugated anti-mouse antibody is used for developing.

In addition, humoral responses are measured by FACS analysis. 38C13 tumor cells are incubated with sera from vaccinated mice, using FITC-conjugated goat anti-mouse (Vector Laboratories, Inc., Burlingame, Calif.) as a secondary antibody. 38C13 tumor cells will be stained using mouse serum as the primary antibody. 38C13 BCR-specific serum IgG titers are determined based on the greatest dilution of serum that confers a significant shift when staining 38C13 cells relative to background staining of 38C13V2 cells.

Cellular Immunity:

Vaccination-induced induction of $CD4^+$ and $CD8^+$ T cells is measured in peripheral lymphoid organs. Splenocytes are harvested at day 10 and $CD4^+$ and $CD8^+$ T cells isolated using Milenyi magnetic bead separation with either anti-CD8 or anti-CD4 and anti-I-Ab monoclonal antibodies, followed by anti-rat IgG-, anti-mouse IgG-, and anti-mouse IgM-coupled magnetic beads (Perseptive Biosystems, Cambridge, Mass.), and subsequently separated into $CD4^+$ and $CD8^+$ populations through a magnetic separation column fitted between a MACS magnet (Miltenyi Biotec). The resultant populations (more than 90% pure by FACS analysis) are analyzed for ability to secrete FN-gamma in response to a pool of 15-mer peptides overlapping by 11 AA (100 mcg/ml) peptides representing the full length of the 38C13 Fv sequence ($CD8^+$) or recombinant 38C13 BCR not coupled to carrier protein ($CD4^+$).

What is claimed:

1. A fusion peptide comprising a listeriolysin O (LLO) protein or a fragment thereof and an antigen, wherein said LLO protein or fragment thereof is chemically conjugated to said antigen, wherein said chemical conjugation to said antigen enables both a cell-mediated response and a humoral response to said antigen, wherein said antigen is a fragment of a B cell receptor (BCR), and wherein said fragment comprises the idiotype of said BCR.

2. The peptide of claim 1, wherein said fragment of a BCR is a single chain fragment of the variable regions (scFV) of said BCR.

3. An isolated peptide vaccine mixture, comprising an LLO protein or fragment thereof, and an antigen, wherein said antigen is either
   a. a B cell receptor (BCR); or
   b. a fragment of a BCR, wherein said fragment comprises the idiotype of said BCR.

4. The peptide vaccine mixture of claim 3, wherein said fragment of a BCR is a single chain fragment of the variable regions (scFV) of said BCR.

5. The peptide of claim 1, wherein said fragment of a BCR is a 38C13 idiotype of said BCR.

6. The peptide of claim 3, wherein said fragment of a BCR is a 38C13 idiotype of said BCR.

7. The peptide of claim 5, wherein said 38C13 idiotype comprises SEQ ID NO: 48.

8. The peptide of claim 6, wherein said 38C13 idiotype comprises SEQ ID NO: 48.

9. The peptide of claim 1, wherein said fragment of an LLO protein is an N-terminal fragment.

10. The peptide of claim 3, wherein said fragment of an LLO protein is an N-terminal fragment.

11. The peptide of claim 9, wherein said N-terminal LLO fragment is a LLO-detox consisting of amino acids 20-442 of an LLO protein.

12. The peptide of claim 10, wherein said N-terminal LLO fragment is a LLO-detox consisting of amino acids 20-442 of an LLO protein.

* * * * *

SEQUENCE LISTING

<160> NUMBER OF SEQ ID NOS: 48

<210> SEQ ID NO 1
<211> LENGTH: 32
<212> TYPE: PRT
<213> ORGANISM: Listeria monocytogenes

```
<400> SEQUENCE: 1

Lys Glu Asn Ser Ile Ser Ser Met Ala Pro Pro Ala Ser Pro Pro Ala
1               5                   10                  15

Ser Pro Lys Thr Pro Ile Glu Lys Lys His Ala Asp Glu Ile Asp Lys
            20                  25                  30

<210> SEQ ID NO 2
<211> LENGTH: 14
<212> TYPE: PRT
<213> ORGANISM: Listeria monocytogenes

<400> SEQUENCE: 2

Lys Thr Glu Glu Gln Pro Ser Glu Val Asn Thr Gly Pro Arg
1               5                   10

<210> SEQ ID NO 3
<211> LENGTH: 28
<212> TYPE: PRT
<213> ORGANISM: Listeria monocytogenes

<400> SEQUENCE: 3

Lys Ala Ser Val Thr Asp Thr Ser Glu Gly Asp Leu Asp Ser Ser Met
1               5                   10                  15

Gln Ser Ala Asp Glu Ser Thr Pro Gln Pro Leu Lys
            20                  25

<210> SEQ ID NO 4
<211> LENGTH: 20
<212> TYPE: PRT
<213> ORGANISM: Listeria monocytogenes

<400> SEQUENCE: 4

Lys Asn Glu Glu Val Asn Ala Ser Asp Phe Pro Pro Pro Pro Thr Asp
1               5                   10                  15

Glu Glu Leu Arg
            20

<210> SEQ ID NO 5
<211> LENGTH: 33
<212> TYPE: PRT
<213> ORGANISM: Listeria monocytogenes

<400> SEQUENCE: 5

Arg Gly Gly Ile Pro Thr Ser Glu Glu Phe Ser Ser Leu Asn Ser Gly
1               5                   10                  15

Asp Phe Thr Asp Asp Glu Asn Ser Glu Thr Thr Glu Glu Glu Ile Asp
            20                  25                  30

Arg

<210> SEQ ID NO 6
<211> LENGTH: 17
<212> TYPE: PRT
<213> ORGANISM: Streptococcus pyogenes

<400> SEQUENCE: 6

Lys Gln Asn Thr Ala Ser Thr Glu Thr Thr Thr Thr Asn Glu Gln Pro
1               5                   10                  15

Lys

<210> SEQ ID NO 7
```

<211> LENGTH: 17
<212> TYPE: PRT
<213> ORGANISM: Streptococcus equisimilis

<400> SEQUENCE: 7

Lys Gln Asn Thr Ala Asn Thr Glu Thr Thr Thr Thr Asn Glu Gln Pro
1               5                   10                  15

Lys

<210> SEQ ID NO 8
<211> LENGTH: 22
<212> TYPE: DNA
<213> ORGANISM: Artificial Sequence
<220> FEATURE:
<223> OTHER INFORMATION: primer

<400> SEQUENCE: 8
ggctcgagca tggagataca cc                                              22

<210> SEQ ID NO 9
<211> LENGTH: 28
<212> TYPE: DNA
<213> ORGANISM: Artificial Sequence
<220> FEATURE:
<223> OTHER INFORMATION: primer

<400> SEQUENCE: 9
ggggactagt ttatggtttc tgagaaca                                        28

<210> SEQ ID NO 10
<211> LENGTH: 31
<212> TYPE: DNA
<213> ORGANISM: Artificial Sequence
<220> FEATURE:
<223> OTHER INFORMATION: primer

<400> SEQUENCE: 10
gggggctagc cctcctttga ttagtatatt c                                    31

<210> SEQ ID NO 11
<211> LENGTH: 28
<212> TYPE: DNA
<213> ORGANISM: Artificial Sequence
<220> FEATURE:
<223> OTHER INFORMATION: primer

<400> SEQUENCE: 11
ctccctcgag atcataattt acttcatc                                        28

<210> SEQ ID NO 12
<211> LENGTH: 55
<212> TYPE: DNA
<213> ORGANISM: Artificial Sequence
<220> FEATURE:
<223> OTHER INFORMATION: primer

<400> SEQUENCE: 12
gactacaagg acgatgaccg acaagtgata acccgggatc taaataaatc cgttt          55

<210> SEQ ID NO 13
<211> LENGTH: 27
<212> TYPE: DNA
<213> ORGANISM: Artificial Sequence
<220> FEATURE:
<223> OTHER INFORMATION: primer

<400> SEQUENCE: 13
cccgtcgacc agctcttctt ggtgaag    27

<210> SEQ ID NO 14
<211> LENGTH: 31
<212> TYPE: DNA
<213> ORGANISM: Artificial Sequence
<220> FEATURE:
<223> OTHER INFORMATION: primer

<400> SEQUENCE: 14
ggggtctaga cctcctttga ttagtatatt c    31

<210> SEQ ID NO 15
<211> LENGTH: 45
<212> TYPE: DNA
<213> ORGANISM: Artificial Sequence
<220> FEATURE:
<223> OTHER INFORMATION: primer

<400> SEQUENCE: 15
atcttcgcta tctgtcgccg cggcgcgtgc ttcagtttgt tgcgc    45

<210> SEQ ID NO 16
<211> LENGTH: 45
<212> TYPE: DNA
<213> ORGANISM: Artificial Sequence
<220> FEATURE:
<223> OTHER INFORMATION: primer

<400> SEQUENCE: 16
gcgcaacaaa ctgaagcagc ggccgcggcg acagatagcg aagat    45

<210> SEQ ID NO 17
<211> LENGTH: 42
<212> TYPE: DNA
<213> ORGANISM: Artificial Sequence
<220> FEATURE:
<223> OTHER INFORMATION: primer

<400> SEQUENCE: 17
tgtaggtgta tctccatgct cgagagctag gcgatcaatt tc    42

<210> SEQ ID NO 18
<211> LENGTH: 42
<212> TYPE: DNA
<213> ORGANISM: Artificial Sequence
<220> FEATURE:
<223> OTHER INFORMATION: primer

<400> SEQUENCE: 18
ggaattgatc gcctagctct cgagcatgga gatacaccta ca    42

<210> SEQ ID NO 19
<211> LENGTH: 42
<212> TYPE: DNA
<213> ORGANISM: Artificial Sequence
<220> FEATURE:
<223> OTHER INFORMATION: primer

<400> SEQUENCE: 19
aaacggattt atttagatcc cgggttatgg tttctgagaa ca    42

<210> SEQ ID NO 20
<211> LENGTH: 42

```
<212> TYPE: DNA
<213> ORGANISM: Artificial Sequence
<220> FEATURE:
<223> OTHER INFORMATION: primer

<400> SEQUENCE: 20
tgttctcaga aaccataacc cgggatctaa ataaatccgt tt                          42

<210> SEQ ID NO 21
<211> LENGTH: 28
<212> TYPE: DNA
<213> ORGANISM: Artificial Sequence
<220> FEATURE:
<223> OTHER INFORMATION: primer

<400> SEQUENCE: 21
gggggtcgac cagctcttct tggtgaag                                         28

<210> SEQ ID NO 22
<211> LENGTH: 9
<212> TYPE: PRT
<213> ORGANISM: Human papillomavirus type 16

<400> SEQUENCE: 22

Arg Ala His Tyr Asn Ile Val Thr Phe
1               5

<210> SEQ ID NO 23
<211> LENGTH: 390
<212> TYPE: PRT
<213> ORGANISM: Listeria monocytogenes

<400> SEQUENCE: 23

Met Arg Ala Met Met Val Val Phe Ile Thr Ala Asn Cys Ile Thr Ile
1               5                   10                  15

Asn Pro Asp Ile Ile Phe Ala Ala Thr Asp Ser Glu Asp Ser Ser Leu
            20                  25                  30

Asn Thr Asp Glu Trp Glu Glu Glu Lys Thr Glu Glu Gln Pro Ser Glu
        35                  40                  45

Val Asn Thr Gly Pro Arg Tyr Glu Thr Ala Arg Glu Val Ser Ser Arg
    50                  55                  60

Asp Ile Lys Glu Leu Glu Lys Ser Asn Lys Val Arg Asn Thr Asn Lys
65                  70                  75                  80

Ala Asp Leu Ile Ala Met Leu Lys Glu Lys Ala Glu Lys Gly Pro Asn
                85                  90                  95

Ile Asn Asn Asn Asn Ser Glu Gln Thr Glu Asn Ala Ala Ile Asn Glu
            100                 105                 110

Glu Ala Ser Gly Ala Asp Arg Pro Ala Ile Gln Val Glu Arg Arg His
        115                 120                 125

Pro Gly Leu Pro Ser Asp Ser Ala Ala Glu Ile Lys Lys Arg Arg Lys
    130                 135                 140

Ala Ile Ala Ser Ser Asp Ser Glu Leu Glu Ser Leu Thr Tyr Pro Asp
145                 150                 155                 160

Lys Pro Thr Lys Val Asn Lys Lys Val Ala Lys Glu Ser Val Ala
                165                 170                 175

Asp Ala Ser Glu Ser Asp Leu Asp Ser Ser Met Gln Ser Ala Asp Glu
            180                 185                 190

Ser Ser Pro Gln Pro Leu Lys Ala Asn Gln Gln Pro Phe Phe Pro Lys
        195                 200                 205
```

```
Val Phe Lys Lys Ile Lys Asp Ala Gly Lys Trp Val Arg Asp Lys Ile
210                 215                 220

Asp Glu Asn Pro Glu Val Lys Lys Ala Ile Val Asp Lys Ser Ala Gly
225                 230                 235                 240

Leu Ile Asp Gln Leu Leu Thr Lys Lys Lys Ser Glu Glu Val Asn Ala
            245                 250                 255

Ser Asp Phe Pro Pro Pro Thr Asp Glu Glu Leu Arg Leu Ala Leu
            260                 265                 270

Pro Glu Thr Pro Met Leu Leu Gly Phe Asn Ala Pro Ala Thr Ser Glu
                275                 280                 285

Pro Ser Ser Phe Glu Phe Pro Pro Pro Thr Asp Glu Glu Leu Arg
290                 295                 300

Leu Ala Leu Pro Glu Thr Pro Met Leu Leu Gly Phe Asn Ala Pro Ala
305                 310                 315                 320

Thr Ser Glu Pro Ser Ser Phe Glu Phe Pro Pro Pro Thr Glu Asp
                325                 330                 335

Glu Leu Glu Ile Ile Arg Glu Thr Ala Ser Ser Leu Asp Ser Ser Phe
                340                 345                 350

Thr Arg Gly Asp Leu Ala Ser Leu Arg Asn Ala Ile Asn Arg His Ser
                355                 360                 365

Gln Asn Phe Ser Asp Phe Pro Pro Ile Pro Thr Glu Glu Glu Leu Asn
            370                 375                 380

Gly Arg Gly Gly Arg Pro
385                 390

<210> SEQ ID NO 24
<211> LENGTH: 1170
<212> TYPE: DNA
<213> ORGANISM: Listeria monocytogenes

<400> SEQUENCE: 24
atgcgtgcga tgatggtggt tttcattact gccaattgca ttacgattaa ccccgacata     60
atatttgcag cgacagatag cgaagattct agtctaaaca cagatgaatg ggaagaagaa    120
aaaacagaag agcaaccaag cgaggtaaat acgggaccaa gatacgaaac tgcacgtgaa    180
gtaagttcac gtgatattaa agaactagaa aaatcgaata agtgagaaa tacgaacaaa    240 gcagacctaa tagcaatgtt gaaagaaaaa gcagaaaaag gtccaaatat caataataac    300
aacagtgaac aaactgagaa tgcggctata aatgaagagg cttcaggagc cgaccgacca    360
gctatacaag tggagcgtcg tcatccagga ttgccatcgg atagcgcagc ggaaattaaa    420
aaaagaagga aagccatagc atcatcggat agtgagcttg aaagccttac ttatccggat    480
aaaccaacaa aagtaaataa gaaaaaagtg gcgaaagagt cagttgcgga tgcttctgaa    540
agtgacttag attctagcat gcagtcagca gatgagtctt caccacaacc tttaaaagca    600
aaccaacaac cattttttccc taaagtattt aaaaaaataa aagatgcggg gaaatgggta    660
cgtgataaaa tcgacgaaaa tcctgaagta agaaagcga ttgttgataa agtgcaggg    720 ttaattgacc aattattaac caaaagaaa agtgaagagg taatgcttc ggacttcccg    780 ccaccaccta cggatgaaga gttaagactt gctttgccag agacaccaat gcttcttggt    840
tttaatgctc ctgctacatc agaaccgagc tcattcgaat tccaccacc acctacggat    900 gaagagttaa gacttgcttt gccagagacg ccaatgcttc ttggttttaa tgctcctgct    960
acatcggaac cgagctcgtt cgaatttcca ccgcctccaa cagaagatga actagaaatc   1020
atccgggaaa cagcatcctc gctagattct agttttacaa gaggggattt agctagtttg   1080
```

```
agaaatgcta ttaatcgcca tagtcaaaat ttctctgatt tcccaccaat cccaacagaa      1140
gaagagttga acgggagagg cggtagacca                                      1170

<210> SEQ ID NO 25
<211> LENGTH: 441
<212> TYPE: PRT
<213> ORGANISM: Listeria monocytogenes

<400> SEQUENCE: 25
```

Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
            20                  25                  30

Glu Asn Ser Ile Ser Ser Val Ala Pro Pro Ala Ser Pro Pro Ala Ser
        35                  40                  45

Pro Lys Thr Pro Ile Glu Lys Lys His Ala Asp Glu Ile Asp Lys Tyr
    50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Ser Ile Asn Gln Asn Asn
            100                 105                 110

Ala Asp Ile Gln Val Val Asn Ala Ile Ser Ser Leu Thr Tyr Pro Gly
        115                 120                 125

Ala Leu Val Lys Ala Asn Ser Glu Leu Val Glu Asn Gln Pro Asp Val
    130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
                165                 170                 175

Asn Val Asn Asn Ala Val Asn Thr Leu Val Glu Arg Trp Asn Glu Lys
            180                 185                 190

Tyr Ala Gln Ala Tyr Ser Asn Val Ser Ala Lys Ile Asp Tyr Asp Asp
        195                 200                 205

Glu Met Ala Tyr Ser Glu Ser Gln Leu Ile Ala Lys Phe Gly Thr Ala
    210                 215                 220

Phe Lys Ala Val Asn Asn Ser Leu Asn Val Asn Phe Gly Ala Ile Ser
225                 230                 235                 240

Glu Gly Lys Met Gln Glu Glu Val Ile Ser Phe Lys Gln Ile Tyr Tyr
                245                 250                 255

Asn Val Asn Val Asn Glu Pro Thr Arg Pro Ser Arg Phe Phe Gly Lys
            260                 265                 270

Ala Val Thr Lys Glu Gln Leu Gln Ala Leu Gly Val Asn Ala Glu Asn
        275                 280                 285

Pro Pro Ala Tyr Ile Ser Ser Val Ala Tyr Gly Arg Gln Val Tyr Leu
    290                 295                 300

Lys Leu Ser Thr Asn Ser His Ser Thr Lys Val Lys Ala Ala Phe Asp
305                 310                 315                 320

Ala Ala Val Ser Gly Lys Ser Val Ser Gly Asp Val Glu Leu Thr Asn
                325                 330                 335

Ile Ile Lys Asn Ser Ser Phe Lys Ala Val Ile Tyr Gly Gly Ser Ala
            340                 345                 350

-continued

```
Lys Asp Glu Val Gln Ile Ile Asp Gly Asn Leu Gly Asp Leu Arg Asp
                355                 360                 365
Ile Leu Lys Lys Gly Ala Thr Phe Asn Arg Glu Thr Pro Gly Val Pro
        370                 375                 380
Ile Ala Tyr Thr Thr Asn Phe Leu Lys Asp Asn Glu Leu Ala Val Ile
385                 390                 395                 400
Lys Asn Asn Ser Glu Tyr Ile Glu Thr Thr Ser Lys Ala Tyr Thr Asp
                405                 410                 415
Gly Lys Ile Asn Ile Asp His Ser Gly Gly Tyr Val Ala Gln Phe Asn
            420                 425                 430
Ile Ser Trp Asp Glu Val Asn Tyr Asp
            435                 440

<210> SEQ ID NO 26
<211> LENGTH: 47
<212> TYPE: DNA
<213> ORGANISM: Artificial Sequence
<220> FEATURE:
<223> OTHER INFORMATION: primer

<400> SEQUENCE: 26
cacgcggatg aaatcgataa gctcgagccc cccggaatcg cgggcac              47

<210> SEQ ID NO 27
<211> LENGTH: 38
<212> TYPE: DNA
<213> ORGANISM: Artificial Sequence
<220> FEATURE:
<223> OTHER INFORMATION: primer

<400> SEQUENCE: 27
ccggactagt gacctcttgg ttattcgggg gacacacc                        38

<210> SEQ ID NO 28
<211> LENGTH: 34
<212> TYPE: DNA
<213> ORGANISM: Artificial Sequence
<220> FEATURE:
<223> OTHER INFORMATION: primer

<400> SEQUENCE: 28
ccgggtcgac tgcccctaca actacctgtc tacg                            34

<210> SEQ ID NO 29
<211> LENGTH: 58
<212> TYPE: DNA
<213> ORGANISM: Artificial Sequence
<220> FEATURE:
<223> OTHER INFORMATION: primer

<400> SEQUENCE: 29
ccggactagt ttacttgtca tcgtcgtcct tgtagtcccc actgtggagc agggcctg  58

<210> SEQ ID NO 30
<211> LENGTH: 34
<212> TYPE: DNA
<213> ORGANISM: Artificial Sequence
<220> FEATURE:
<223> OTHER INFORMATION: primer

<400> SEQUENCE: 30
ccgggtcgac tgctttgtac acactgtacc ttgg                            34
```

```
<210> SEQ ID NO 31
<211> LENGTH: 58
<212> TYPE: DNA
<213> ORGANISM: Artificial Sequence
<220> FEATURE:
<223> OTHER INFORMATION: primer

<400> SEQUENCE: 31
ccggactagt ttacttgtca tcgtcgtcct tgtagtccgg gctggctctc tgctctgc      58

<210> SEQ ID NO 32
<211> LENGTH: 35
<212> TYPE: DNA
<213> ORGANISM: Artificial Sequence
<220> FEATURE:
<223> OTHER INFORMATION: primer

<400> SEQUENCE: 32
ccggctcgag tatacgatgc gtaggctgct gcagg                                35

<210> SEQ ID NO 33
<211> LENGTH: 34
<212> TYPE: DNA
<213> ORGANISM: Artificial Sequence
<220> FEATURE:
<223> OTHER INFORMATION: primer

<400> SEQUENCE: 33
ccggactagt agccagtgga gatctggggg gccc                                 34

<210> SEQ ID NO 34
<211> LENGTH: 32
<212> TYPE: DNA
<213> ORGANISM: Artificial Sequence
<220> FEATURE:
<223> OTHER INFORMATION: primer

<400> SEQUENCE: 34
ccggctcgag ggtgacctgg tagacgctga ag                                   32

<210> SEQ ID NO 35
<211> LENGTH: 32
<212> TYPE: DNA
<213> ORGANISM: Artificial Sequence
<220> FEATURE:
<223> OTHER INFORMATION: primer

<400> SEQUENCE: 35
ccggactagt tacaggtaca tccaggccta gg                                   32

<210> SEQ ID NO 36
<211> LENGTH: 9
<212> TYPE: PRT
<213> ORGANISM: Homo sapiens

<400> SEQUENCE: 36

Pro Asp Ser Leu Arg Asp Leu Val Phe
1               5

<210> SEQ ID NO 37
<211> LENGTH: 33
<212> TYPE: DNA
<213> ORGANISM: Artificial Sequence
<220> FEATURE:
<223> OTHER INFORMATION: primer

<400> SEQUENCE: 37
```

```
ccgggctagc atggtcatca tggagctggc cgg                              33
```

<210> SEQ ID NO 38
<211> LENGTH: 58
<212> TYPE: DNA
<213> ORGANISM: Artificial Sequence
<220> FEATURE:
<223> OTHER INFORMATION: primer

<400> SEQUENCE: 38

```
ccgggatatc ttacttgtca tcgtcgtcct tgtagtctca tacaggtaca tccaggcc    58
```

<210> SEQ ID NO 39
<211> LENGTH: 33
<212> TYPE: DNA
<213> ORGANISM: Artificial Sequence
<220> FEATURE:
<223> OTHER INFORMATION: primer

<400> SEQUENCE: 39

```
ccgggtcgac atggtcatca tggagctggc cgg                              33
```

<210> SEQ ID NO 40
<211> LENGTH: 61
<212> TYPE: DNA
<213> ORGANISM: Artificial Sequence
<220> FEATURE:
<223> OTHER INFORMATION: primer

<400> SEQUENCE: 40

```
ccgggatatc ttacttgtca tcgtcgtcct tgtagtctca gacctcttgg ttattcgggg  60
g                                                                 61
```

<210> SEQ ID NO 41
<211> LENGTH: 416
<212> TYPE: PRT
<213> ORGANISM: Listeria monocytogenes

<400> SEQUENCE: 41

```
Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
            20                  25                  30

Glu Asn Ser Ile Ser Ser Val Ala Pro Pro Ala Ser Pro Pro Ala Ser
        35                  40                  45

Pro Lys Thr Pro Ile Glu Lys Lys His Ala Asp Glu Ile Asp Lys Tyr
    50                  55                  60

Ile Gln Gly Leu Asp Tyr Asn Lys Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Ser Ile Asn Gln Asn Asn
            100                 105                 110

Ala Asp Ile Gln Val Val Asn Ala Ile Ser Ser Leu Thr Tyr Pro Gly
        115                 120                 125

Ala Leu Val Lys Ala Asn Ser Glu Leu Val Glu Asn Gln Pro Asp Val
    130                 135                 140

Leu Pro Val Lys Arg Asp Ser Leu Thr Leu Ser Ile Asp Leu Pro Gly
145                 150                 155                 160
```

```
Met Thr Asn Gln Asp Asn Lys Ile Val Val Lys Asn Ala Thr Lys Ser
                165                 170                 175

Asn Val Asn Asn Ala Val Asn Thr Leu Val Glu Arg Trp Asn Glu Lys
            180                 185                 190

Tyr Ala Gln Ala Tyr Ser Asn Val Ser Ala Lys Ile Asp Tyr Asp Asp
        195                 200                 205

Glu Met Ala Tyr Ser Glu Ser Gln Leu Ile Ala Lys Phe Gly Thr Ala
    210                 215                 220

Phe Lys Ala Val Asn Asn Ser Leu Asn Val Asn Phe Gly Ala Ile Ser
225                 230                 235                 240

Glu Gly Lys Met Gln Glu Val Ile Ser Phe Lys Gln Ile Tyr Tyr
                245                 250                 255

Asn Val Asn Val Asn Glu Pro Thr Arg Pro Ser Arg Phe Phe Gly Lys
            260                 265                 270

Ala Val Thr Lys Glu Gln Leu Gln Ala Leu Gly Val Asn Ala Glu Asn
        275                 280                 285

Pro Pro Ala Tyr Ile Ser Ser Val Ala Tyr Gly Arg Gln Val Tyr Leu
    290                 295                 300

Lys Leu Ser Thr Asn Ser His Ser Thr Lys Val Lys Ala Ala Phe Asp
305                 310                 315                 320

Ala Ala Val Ser Gly Lys Ser Val Ser Gly Asp Val Glu Leu Thr Asn
                325                 330                 335

Ile Ile Lys Asn Ser Ser Phe Lys Ala Val Ile Tyr Gly Gly Ser Ala
            340                 345                 350

Lys Asp Glu Val Gln Ile Ile Asp Gly Asn Leu Gly Asp Leu Arg Asp
        355                 360                 365

Ile Leu Lys Lys Gly Ala Thr Phe Asn Arg Glu Thr Pro Gly Val Pro
    370                 375                 380

Ile Ala Tyr Thr Thr Asn Phe Leu Lys Asp Asn Glu Leu Ala Val Ile
385                 390                 395                 400

Lys Asn Asn Ser Glu Tyr Ile Glu Thr Thr Ser Lys Ala Tyr Thr Asp
                405                 410                 415

<210> SEQ ID NO 42
<211> LENGTH: 529
<212> TYPE: PRT
<213> ORGANISM: Listeria monocytogenes

<400> SEQUENCE: 42

Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
            20                  25                  30

Glu Asn Ser Ile Ser Ser Met Ala Pro Pro Ala Ser Pro Pro Ala Ser
        35                  40                  45

Pro Lys Thr Pro Ile Glu Lys Lys His Ala Asp Glu Ile Asp Lys Tyr
    50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Ser Ile Asn Gln Asn Asn
            100                 105                 110

Ala Asp Ile Gln Val Val Asn Ala Ile Ser Ser Leu Thr Tyr Pro Gly
        115                 120                 125
```

```
Ala Leu Val Lys Ala Asn Ser Glu Leu Val Glu Asn Gln Pro Asp Val
            130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
                165                 170                 175

Asn Val Asn Asn Ala Val Asn Thr Leu Val Glu Arg Trp Asn Glu Lys
            180                 185                 190

Tyr Ala Gln Ala Tyr Pro Asn Val Ser Ala Lys Ile Asp Tyr Asp Asp
        195                 200                 205

Glu Met Ala Tyr Ser Glu Ser Gln Leu Ile Ala Lys Phe Gly Thr Ala
210                 215                 220

Phe Lys Ala Val Asn Asn Ser Leu Asn Val Asn Phe Gly Ala Ile Ser
225                 230                 235                 240

Glu Gly Lys Met Gln Glu Val Ile Ser Phe Lys Gln Ile Tyr Tyr
                245                 250                 255

Asn Val Asn Val Asn Glu Pro Thr Arg Pro Ser Arg Phe Phe Gly Lys
            260                 265                 270

Ala Val Thr Lys Glu Gln Leu Gln Ala Leu Gly Val Asn Ala Glu Asn
        275                 280                 285

Pro Pro Ala Tyr Ile Ser Ser Val Ala Tyr Gly Arg Gln Val Tyr Leu
290                 295                 300

Lys Leu Ser Thr Asn Ser His Ser Thr Lys Val Lys Ala Ala Phe Asp
305                 310                 315                 320

Ala Ala Val Ser Gly Lys Ser Val Ser Gly Asp Val Glu Leu Thr Asn
                325                 330                 335

Ile Ile Lys Asn Ser Ser Phe Lys Ala Val Ile Tyr Gly Gly Ser Ala
            340                 345                 350

Lys Asp Glu Val Gln Ile Ile Asp Gly Asn Leu Gly Asp Leu Arg Asp
        355                 360                 365

Ile Leu Lys Lys Gly Ala Thr Phe Asn Arg Glu Thr Pro Gly Val Pro
370                 375                 380

Ile Ala Tyr Thr Thr Asn Phe Leu Lys Asp Asn Glu Leu Ala Val Ile
385                 390                 395                 400

Lys Asn Asn Ser Glu Tyr Ile Glu Thr Thr Ser Lys Ala Tyr Thr Asp
                405                 410                 415

Gly Lys Ile Asn Ile Asp His Ser Gly Gly Tyr Val Ala Gln Phe Asn
            420                 425                 430

Ile Ser Trp Asp Glu Val Asn Tyr Asp Pro Glu Gly Asn Glu Ile Val
        435                 440                 445

Gln His Lys Asn Trp Ser Glu Asn Asn Lys Ser Lys Leu Ala His Phe
450                 455                 460

Thr Ser Ser Ile Tyr Leu Pro Gly Asn Ala Arg Asn Ile Asn Val Tyr
465                 470                 475                 480

Ala Lys Glu Cys Thr Gly Leu Ala Trp Glu Trp Arg Thr Val Ile
                485                 490                 495

Asp Asp Arg Asn Leu Pro Leu Val Lys Asn Arg Asn Ile Ser Ile Trp
            500                 505                 510

Gly Thr Thr Leu Tyr Pro Lys Tyr Ser Asn Lys Val Asp Asn Pro Ile
        515                 520                 525

Glu
```

```
<210> SEQ ID NO 43
<211> LENGTH: 25
<212> TYPE: DNA
<213> ORGANISM: Artificial Sequence
<220> FEATURE:
<223> OTHER INFORMATION: primer

<400> SEQUENCE: 43
gcggatccca tgagataca cctac                                            25

<210> SEQ ID NO 44
<211> LENGTH: 22
<212> TYPE: DNA
<213> ORGANISM: Artificial Sequence
<220> FEATURE:
<223> OTHER INFORMATION: primer

<400> SEQUENCE: 44
gctctagatt atggtttctg ag                                              22

<210> SEQ ID NO 45
<211> LENGTH: 20
<212> TYPE: DNA
<213> ORGANISM: Artificial Sequence
<220> FEATURE:
<223> OTHER INFORMATION: oligonucleotide

<400> SEQUENCE: 45
tccatgacgt tcctgacgtt                                                 20

<210> SEQ ID NO 46
<211> LENGTH: 20
<212> TYPE: DNA
<213> ORGANISM: Artificial Sequence
<220> FEATURE:
<223> OTHER INFORMATION: oligonucleotide

<400> SEQUENCE: 46
tccaggactt ctctcaggtt                                                 20

<210> SEQ ID NO 47
<211> LENGTH: 810
<212> TYPE: DNA
<213> ORGANISM: Artificial Sequence
<220> FEATURE:
<223> OTHER INFORMATION: scfv construct

<400> SEQUENCE: 47
gcccagccgc catgccaggt gaagctgcag gagtcaggag gaggcttggt ccagcctggg     60
ggttctctga gtctctcctg tgcagcttct ggattcacct tcactgatta ctacatgagc    120
tgggtccgcc agcctccagg gaaggcactt gagtggttgg ctttgattag aaacaaagct    180
aatggttaca cagagtacag tgcatctgtg aagggtcggt tcaccatctc cagagataat    240
tcccaaagca tcctctatct tcaaatgaat gccctgagag ctgaggacag tgccacttat    300
tactgtgcaa gagatcccaa ttactacgat ggtagctacg aagggtactt tgactactgg    360
ggccaaggga ccacggtcac cgtctcctca ggcggaggcg gttcaggcgg aggtggctct    420
ggcggtggcg gatcggacat tgagctcacc cagtctccat cctcactgtc tgcatctctg    480
ggaggcaaag tcaccatcac ttgcaaggca agccaagaca ttaacaagta tatagcttgg    540
taccaacaca agcctggaaa aggtcctagg ctgctcatac attacacatc tacattacag    600
ccaggcatcc catcaaggtt cagtggaagt gggtctggga gagattattc cttcagcatc    660
```

```
agcaacctgg agcctgaaga tattgcaact tattattgtc tacagtatga ataatctgtac    720 acgttcggct cggggaccaa gctggaaata aaacgggcgg ccgcagaaca aaaactcatc    780
tcagaagagg atctgaatta ataagaattc                                     810
```

<210> SEQ ID NO 48
<211> LENGTH: 285
<212> TYPE: PRT
<213> ORGANISM: Artificial Sequence
<220> FEATURE:
<223> OTHER INFORMATION: scfv construct

<400> SEQUENCE: 48

```
Met Lys Tyr Leu Leu Pro Thr Ala Ala Ala Gly Leu Leu Leu Leu Ala
1               5                   10                  15

Ala Gln Pro Ala Gln Pro Pro Cys Gln Val Lys Leu Gln Glu Ser Gly
            20                  25                  30

Gly Gly Leu Val Gln Pro Gly Gly Ser Leu Ser Leu Ser Cys Ala Ala
        35                  40                  45

Ser Gly Phe Thr Phe Thr Asp Tyr Tyr Met Ser Trp Val Arg Gln Pro
    50                  55                  60

Pro Gly Lys Ala Leu Glu Trp Leu Ala Leu Ile Arg Asn Lys Ala Asn
65                  70                  75                  80

Gly Tyr Thr Glu Tyr Ser Ala Ser Val Lys Gly Arg Phe Thr Ile Ser
                85                  90                  95

Arg Asp Asn Ser Gln Ser Ile Leu Tyr Leu Gln Met Asn Ala Leu Arg
            100                 105                 110

Ala Glu Asp Ser Ala Thr Tyr Tyr Cys Ala Arg Asp Pro Asn Tyr Tyr
        115                 120                 125

Asp Gly Ser Tyr Glu Gly Tyr Phe Asp Tyr Trp Gly Gln Gly Thr Thr
    130                 135                 140

Val Thr Val Ser Ser Gly Gly Gly Ser Gly Gly Gly Ser Gly
145                 150                 155                 160

Gly Gly Gly Ser Asp Ile Glu Leu Thr Gln Ser Pro Ser Ser Leu Ser
                165                 170                 175

Ala Ser Leu Gly Gly Lys Val Thr Ile Thr Cys Lys Ala Ser Gln Asp
            180                 185                 190

Ile Asn Lys Tyr Ile Ala Trp Tyr Gln His Lys Pro Gly Lys Gly Pro
        195                 200                 205

Arg Leu Leu Ile His Tyr Thr Ser Thr Leu Gln Pro Gly Ile Pro Ser
    210                 215                 220

Arg Phe Ser Gly Ser Gly Ser Gly Arg Asp Tyr Ser Phe Ser Ile Ser
225                 230                 235                 240

Asn Leu Glu Pro Glu Asp Ile Ala Thr Tyr Tyr Cys Leu Gln Tyr Asp
                245                 250                 255

Asn Leu Tyr Thr Phe Gly Ser Gly Thr Lys Leu Glu Ile Lys Arg Ala
            260                 265                 270

Ala Ala Glu Gln Lys Leu Ile Ser Glu Glu Asp Leu Asn
        275                 280                 285
```